United States Patent [19]

Petersen

[11] Patent Number: 4,678,497
[45] Date of Patent: Jul. 7, 1987

[54] TRIAZINE-SUBSTITUTED HERBICIDAL AZOBENZENESULFONAMIDES

[75] Inventor: Wallace C. Petersen, Hockessin, Del.

[73] Assignee: E. I. Du Pont de Nemours and Company, Wilmington, Del.

[21] Appl. No.: 818,133

[22] Filed: Jan. 13, 1986

Related U.S. Application Data

[62] Division of Ser. No. 650,188, Sep. 13, 1984, Pat. No. 4,585,470.

[51] Int. Cl.⁴ .................. A01N 9/22; C07C 107/04; C07C 113/04; C07C 115/00
[52] U.S. Cl. .......................... 71/86; 71/87; 71/92; 71/93; 534/551; 534/552; 534/553; 534/556; 534/557; 534/558; 534/560; 534/565; 534/591; 534/632; 534/646; 534/741; 534/749; 534/774; 534/797; 534/798
[58] Field of Search ............ 534/551, 560, 632, 636, 534/646, 774, 797, 556, 558, 552, 553, 550, 557, 741, 749, 798; 71/87, 92, 93, 86

[56] References Cited

U.S. PATENT DOCUMENTS 4,435,205 4/1984 Reap ........................ 71/92

FOREIGN PATENT DOCUMENTS 0083975 7/1983 European Pat. Off. ........ 71/92

Primary Examiner—Floyd D. Higel

[57] ABSTRACT

Triazine-substituted azobenzenesulfonamides useful as preemergent and postemergent herbicides, selected from compounds of Formulae I or II

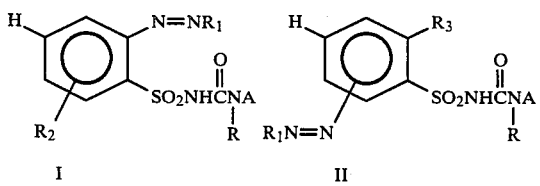

or agriculturally suitable salts thereof, wherein R, $R_1$, $R_2$, $R_3$ and A are as defined herein.

12 Claims, No Drawings

TRIAZINE-SUBSTITUTED HERBICIDAL AZOBENZENESULFONAMIDES

This is a division of application Ser. No. 650,188, filed on Sept. 13, 1984, now U.S. Pat. No. 4,585,470.

BACKGROUND OF THE INVENTION

Benzenesulfonamides having a nitrogen-containing substituents on the benzene ring are known as being herbicidal. For example, U.S. Pat. No. 4,369,058 discloses herbicidal benzenesulfonamides of the general formula

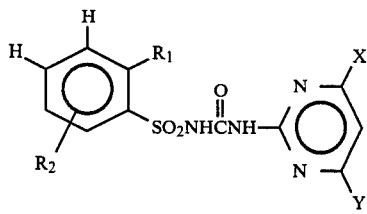

where
$R_1$ is H, Cl, Br, F, $C_1$-$C_4$ alkyl, $OCH_3$ or $NO_2$; and
$R_2$ is NCO, $NHCO_2R_3$, $NHCOSR_3$, $NHCOR_3$, $NHCONR_4R_5$ or $NR_6R_7$.

European Patent Application (EP-A) No. 102,924 discloses herbicidal azidobenzenesulfonamides of the formula

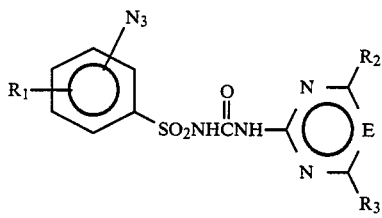

where
$R_1$ is H, halo, $NO_2$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxycarbonyl, $C_1$-$C_4$ alkylthio, $C_1$-$C_4$ alkylsulfinyl, $C_1$-$C_4$ alkylsulfonyl or $C_2$-$C_5$ alkoxyalkoxy.

The present invention provides a novel class of benzenesulfonamides.

SUMMARY OF THE INVENTION

This invention pertains to novel compounds of Formulae I and II, agriculturally suitable compositions containing them and their method of use as general and/or selective, preemergent and postemergent herbicides.

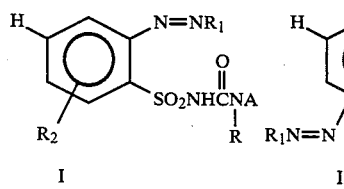 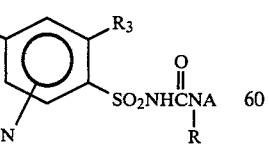

wherein
R is H or $CH_3$;
$R_1$ is $NR_4R_5$, $N(CH_3)OR_6$, NHCN, NRA, $P(W)R_4(W_1R_5)$, $P(W)(W_1R_4)(W_2R_5)$, $P^+(C_6H_5)_3$, $P^+R_6R_7R_8$, $SR_9$, $SO_2R_9$, $C(R_{10})(R_{11})NO_2$, $CH(CN)_2$ or Q;
Q is

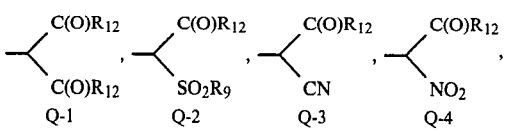

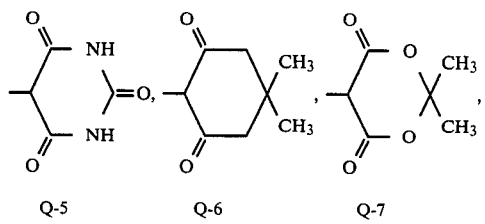

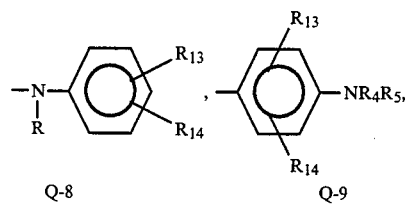

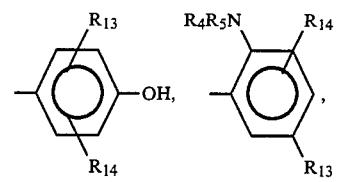

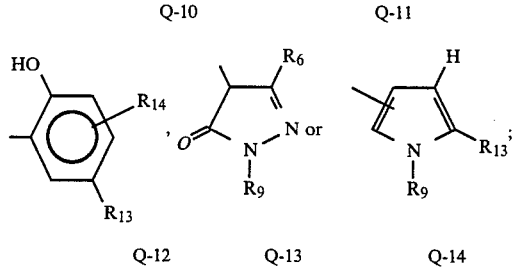

$R_2$ is H, F, Cl, Br, $OCH_3$, $OC_2H_5$, $OCF_2H$, $SCH_3$, $N(CH_3)_2$, $NO_2$, $CH_3$ or $CF_3$;
$R_3$ is H, F, Cl, Br, $C_1$-$C_4$ alkyl, $CO_2R_{15}$, $NO_2$, $CF_3$, $C_1$-$C_4$ alkoxy, $C_1$-$C_4$ alkylthio, $SO_2NR_{16}R_{17}$, $C_1$-$C_4$ alkylsulfonyl, $C_1$-$C_4$ haloalkoxy, $C_1$-$C_4$ alkylsulfonyloxy, $C_2$-$C_5$ alkoxyalkyl or $C_3$-$C_4$ alkenyloxy;
$R_4$ and $R_5$ are independently $C_1$-$C_4$ alkyl, $C_2$-$C_4$ alkyl substituted by 1 atom of Br or 1-3 atoms of F or Cl, $C_3$-$C_5$ alkenyl, $C_3$-$C_5$ cycloalkyl, OH, $OCH_3$, $CH_2OH$, $CH_2OR_6$, or $CH_2CH_2OR_6$; or
$R_4$ and $R_5$ may be taken together as $-(CH_2)_4-$, $-(CH_2)_5-$ or $-(CH_2)_2O(CH_2)_2-$;
$R_6$ is $C_1$-$C_6$ alkyl;
$R_7$ and $R_8$ are independently $C_1$-$C_4$ alkyl;
$R_9$ is $C_1$-$C_4$ alkyl, phenyl or phenyl substituted with 1-3 atoms of F, Cl or 1 Br;
$R_{10}$ and $R_{11}$ are independently H, $C_1$-$C_4$ alkyl, phenyl or phenyl substituted with 1 atom of Br or 1-3 atoms of F or Cl;
$R_{12}$ is $C_1$-$C_4$ alkyl, $C_1$-$C_4$ alkoxy or $NHR_9$;
$R_{13}$ and $R_{14}$ are independently H, $C_1$-$C_3$ alkyl, $OR_6$, $SR_6$, $NHC(O)R_6$, F, Cl, Br or $CO_2R_6$;

$R_{15}$ is $C_1-C_4$ alkyl, $C_3-C_4$ alkenyl, $CH_2CH_2Cl$ or $CH_2CH_2OCH_3$;

$R_{16}$ and $R_{17}$ are independently $C_1-C_2$ alkyl;

W is O or S;

$W_1$ and $W_2$ are independently O, S or NH;

A is

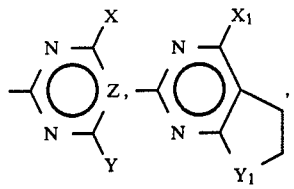

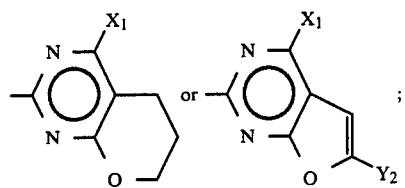

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$ or $CF_3$;

Y is H, $C_1-C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$,

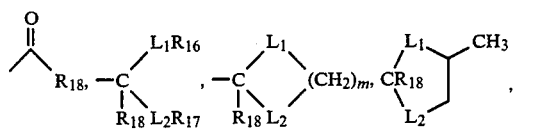

$OCF_2H$, $SCF_2H$ or cyclopropyl;

m is 2 or 3;

$L_1$ and $L_2$ are independently O or S;

$R_{18}$ is H or $CH_3$;

Z is CH or N;

$Y_1$ is O or $CH_2$;

$X_1$ is $CH_3$, $OCH_3$, $OC_2H_5$ or $OCF_2H$; and $Y_2$ is H or $CH_3$;

provided that (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(b) when either X or Y is $OCF_2H$, then Z is CH; and (c) when Q is Q-11 or Q-12, then $R_{13}$ is other than H; and their agriculturally suitable salts.

Preferred for reason of increased ease of synthesis and/or greater herbicidal efficacy are:

(1) Compounds of Formulae I or II where R is H and A is A-1;

(2) Compounds of Preferred 1 where X is $CH_3$, $OCH_3$ or Cl and Y is $CH_3$, $OCH_3$, $OC_2H_5$ or $CH_2OCH_3$; and (3) Compounds of Preferred 2 where $R_2$ is H, Cl, $CH_3$ or $OCH_3$ and $R_3$ is Cl, $C_1-C_3$ alkyl, $C_1-C_3$ alkoxy, $NO_2$, $CO_2(C_1-C_3$ alkyl), $SO_2N(CH_3)_2$, $OSO_2CH_3$, $OSO_2C_2H_5$, $SO_2CH_3$, $SO_2C_2H_5$ or allyloxy.

Specifically preferred for reason of greatest ease of synthesis and/or greatest herbicidal efficacy are:

2-[4-(dimethylamino)phenylazo]-N-[(4-methoxy-6-methylpyrimidin-2-yl)aminocarbonyl]benzenesulfonamide;

[[2-[[(4-methoxy-6-methylpyrimidin-2-yl)aminocarbonyl]aminosulfonyl]phenyl]azo]phosphoric acid, dimethylester; and 2-(dimethyl-1-triazeno)-N-[(4-methoxy-6-methylpyrimidin-2-yl)aminocarbonyl]benzenesulfonamide.

DETAILED DESCRIPTION OF THE INVENTION

Synthesis

Compounds of Formulae I and II can be prepared from the corresponding amino compounds of Formula III by diazotization and coupling with the appropriate reagent as illustrated in Equation 1.

Equation 1

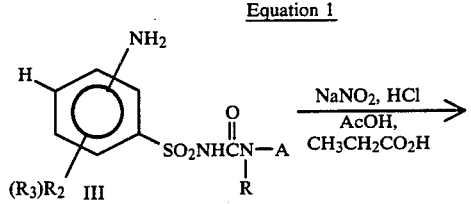

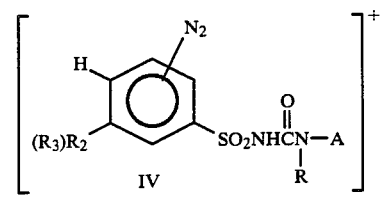

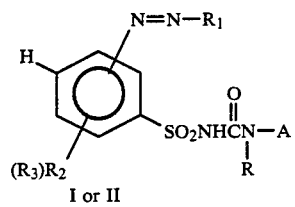

I or II

Diazotization can be carried out in a mixture of acetic and propionic acid to allow lower temperatures and aid in solution of the amine. Sodium nitrite and sufficient hydrochloric acid and water to promote rapid diazotization are added and the mixture held at $-10°$ to 25° C. for 30 minutes to 10 hours.

Alternatively, the esters of nitrous acid, such as n-butylnitrite and amylnitrite may be used to effect diazotization in organic solvents such as alcohols, acetic acid, dioxane and other media.

These and other methods of diazotization are extensively reviewed by H. Zollinger, "Azo and Diazo Chemistry, Aliphatic and Aromatic Compounds", Interscience Publishers, Inc., New York, N.Y. 1961, pp. 13-23 and S. Patai, Editor, "The Chemistry of Diazonium and Diazo Groups", Part II, John Wiley and Sons, New York, N.Y. 1978, pp. 645-659.

Compounds of Formulae I and II can also be prepared by reaction of the appropriate azobenzenesulfonamide (V) with the phenylcarbamate of the heterocyclic amine (VI) in the presence of one equivalent of 1,8-diazabicyclo[5.4.0]undec-7-ene (DBU) as shown in Equation 2.

Equation 2

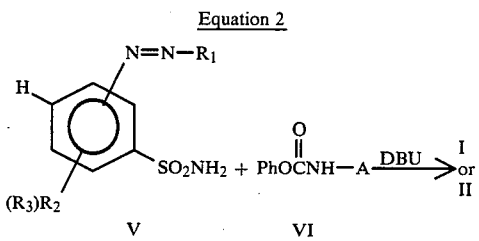

The reaction of Equation 2 is preferably carried out by methods analogous to those described in European Patent Application (EP-A) No. 85,028. The phenylcarbamates of Formula VI can be prepared by the reaction of an appropriate heterocyclic amine of Formula $ANH_2$ with diphenylcarbonate or phenylchloroformate in the presence of a suitable base by methods known to those skilled in the art.

Azobenzenesulfonamides of Formula V can be prepared from the corresponding aminosulfonamides of Formula VII as shown below in Equation 3.

Equation 3

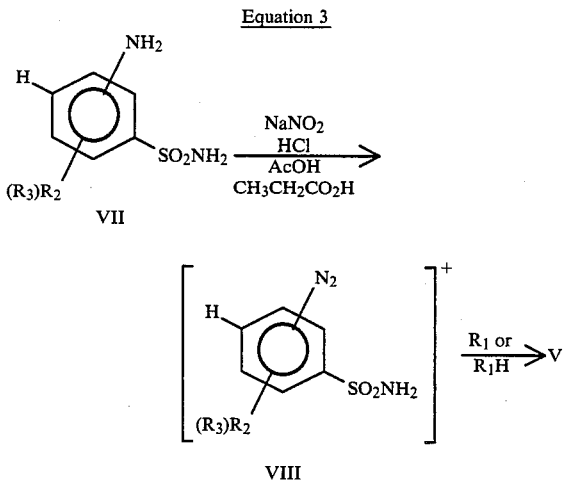

Diazotization can be carried out as described for Equation 1 above.

The coupling of the diazonium salt intermediates IV or VIII with a primary or secondary amine to produce a triazene where $R_1$ is $NR_4R_5$, $N(CH_3)OR_6$, NHCN, NRA,

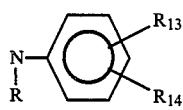

is discussed in the two previous references, Zollinger, p. 177 and Patai, p. 247. The coupling to active methylene compounds where $R_1$ is $C(R_{10})(R_{11})NO_2$, $CH(CN)_2$ or Q where Q is Q-1, Q-2, Q-3, Q-4, Q-5, Q-6 and Q-7 is discussed in Zollinger, p. 199 and Patai, 268. Coupling with sulfur compounds where $R_1$ is $SR_9$, $SO_2R_9$, and $SO_2OR_9$ is discussed in Zollinger, p. 150 and Patai, p. 260. Coupling with phosphorous compounds where $R_1$ is $P(W)R_4(W_1R_5)$, $P(W)(W_1R_4)(W_2R_5)$, $P^+(Ph)_3$, $P^+R_6R_7R_8$ is discussed in Zollinger, p. 152 and by F. Suckfull and H. Haubrich, Angew Chem. 70(8) 238 (1958). Coupling with active aromatic ring systems where $R_1$ is Q-9, Q-10, Q-11, Q-12, Q-13 and Q-14 is well known in the art of dye preparation, as shown for example in H. A. Lubs, Editor, "The Chemistry of Synthetic Dyes and Pigments" Reinhold Publishing Corp., New York, 1955.

Methods suitable for the preparation of amino compounds of Formulae III and VII can be found in U.S. Pat. Nos. 4,225,337 and 4,369,058. Minor modifications of these methods, where appropriate, would be obvious to one skilled in the art.

The synthesis of heterocyclic amine derivatives has been reviewed in "The Chemistry of Heterocyclic Compounds," a series published by Interscience Publ., New York and London. 2-Aminopyrimidines are described by D. J. Brown in "The Pyrimidines", Vol. XVI of the above series. 2-Amino-1,3,5-triazine can be synthesized according to the methods described by E. M. Smolin and L. Rapaport in "s-Triazines and Derivatives," Vol. XIII of the same series. The synthesis of bicyclic pyrimidineamines is described in U.S. Pat. No. 4,339,267. The preparation of pyrimidines and triazines with acetal and ketal substituents is described in European Patent Application (EP-A) No. 84,224 and cyclopropyl substituted systems are taught in EP-A No. 108,708.

Agriculturally suitable salts of compounds of Formulae I or II are also useful herbicides and can be prepared in a number of ways known to the art. For example, metal salts can be made by contacting compounds of Formulae I or II with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I or II can also be prepared by exchange of one cation for another. Cationic exchange can be effected by direct contact of an aqueous solution of a salt of a compound of Formulae I or II (e.g., alkali or quaternary amine salt) with a solution containing the cation to be exchanged. This method is most effective when the desired salt containing the exchanged cation is insoluble in water and can be separated by filtration.

Exchange can also be effected by passing an aqueous solution of a salt of a compound of Formulae I or II (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts useful in this invention can be obtained by reacting a compound of Formulae I or II with a suitable acid, e.g., p-toluenesulfonic acid, trichloroacetic acid or the like.

The synthesis of compounds described in this invention are further illustrated by the following Examples 1 through 3.

EXAMPLE 1

2-(Dimethyl-1-triazeno)-N-[(4-methoxy-6-methylpyrimidin-2-yl)aminocarbonyl]benzenesulfonamide 2-Amino-N-[(4-methoxy-6-methylpyrimidin-2-yl)aminocarbonyl]benzenesulfonamide (3.0 g) in acetic acid (30 mL), propionic acid (20 mL), water (10 mL) and concentrated HCl (2.0 mL) was cooled to 0° C. To this mixture was added sodium nitrite (0.75 g) with stirring. The mixture was held at −10° to 0° C. for 45 minutes. The mixture was then added to an ice and water slurry containing dimethylamine (150 mL, 25% dimethylamine in water). The homogeneous solution was acidified with acetic acid and the heavy white precipitate filtered, washed with water and dried in vacuo, to afford 2.94 g of the title compound as a white solid, m.p. 158°–160° C.

IR: 1705 cm⁻¹, 1620 cm⁻¹.

NMR (CDCl₃): δ 2.4 (s, 3), 3.3 (d, 6), 3.9 (s, 3), 6.3 (s, 1), 7.2–7.7 (m, 3) and 8.3 (d, 1).

EXAMPLE 2

[[2-[[(4-Methoxy-6-methylpyrimidin-2-yl)aminocarbonyl]aminosulfonyl]phenyl]azo]phosphoric acid, dimethyl ester 2-Amino-N-[(4-methoxy-6-methylpyrimidin-2-yl)-aminocarbonyl]benzenesulfonamide (2.0 g) in acetic acid (20 mL) and propionic acid (10 mL) was treated with concentrated hydrochloric acid (1.0 mL) at 0° C. A thick precipitate formed immediately. Sodium nitrite was added (0.41 g) and the slurry rapidly thinned and was stirred at −10° to 0° C. for 1 hour. To the homogeneous solution was added dimethylphosphite (1.0 mL) and enough sodium hydroxide to raise the pH to 7.0. After stirring for 30 minutes, the mixture was diluted with water and extracted with ethyl acetate, water washed, dried and evaporated to a red oil. Chromatography gave a pure fraction of 0.28 g of the title compound, m.p. 155°–156° C.

IR: 3300 cm⁻¹, 1710 cm⁻¹; 1700 cm⁻¹.

NMR (CDCl₃): δ 2.4 (s, 3), 3.9 (s, 3), 3.95 (d, 6), 6.25 (s, 1), 7.2 (m, 1), 7.5 (m, 1), 7.8 (m, 1) and 8.45 (m, 1).

EXAMPLE 3

2-[(4-Dimethylamino)phenylazo]-N-[(4-methoxy-6-methylpyrimidin-2-yl)aminocarbonyl]benzenesulfonamide 2-Amino-N-[(4-methoxy-6-methylpyrimidin-2-yl)-aminocarbonyl]benzenesulfonamide (1.0 g) in acetic acid (25 mL) was treated with n-butyl nitrite (0.31 g) at 25° C. for 3 hours. The solution became homogeneous on addition of the n-butyl nitrite. N,N-Dimethylaniline (0.5 g) was then added and the mixture stirred at 25° C. for 2 hours. The fine orange crystals were filtered and water washed and dried to afford 0.47 g of the title compound, m.p. 210°–211° C. A second crop was isolated from the filtrate, 0.2 g, m.p. 198°–204° C.

IR: 1710 cm⁻¹.

NMR (TFA): δ 2.6 (s, 3), 3.6 (s, 6), 4.2 (s, 3), 6.6 (s, 1) and 7.2–8.2 (m, 8).

Using the procedures of Examples 1–3, and the synthetic routes disclosed herein, the compounds of Tables I–XXXII can be prepared.

GENERAL FORMULAS FOR TABLES I-XXXII

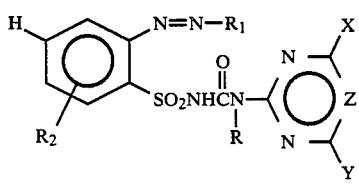

I

-continued
GENERAL FORMULAS FOR TABLES I-XXXII

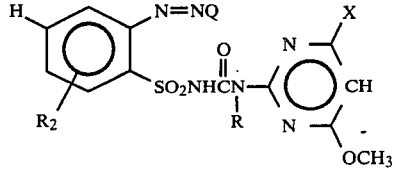

II

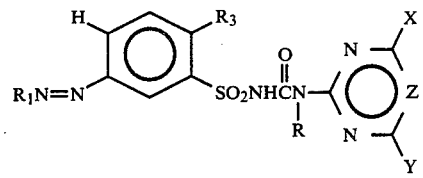

III

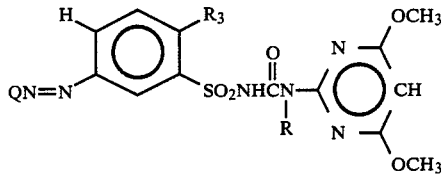

IV

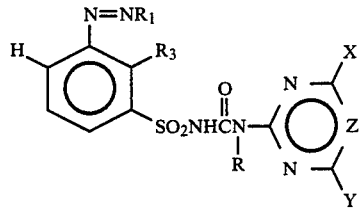

V

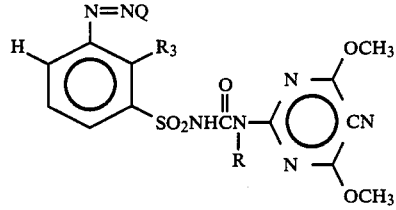

VI

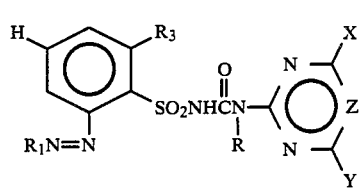

VII

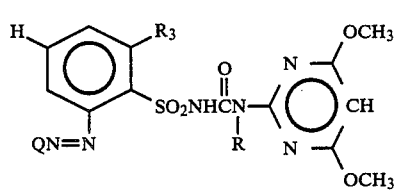

VIII

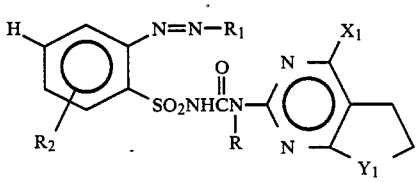

IX

-continued
GENERAL FORMULAS FOR TABLES I-XXXII
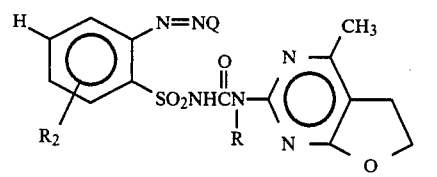 X
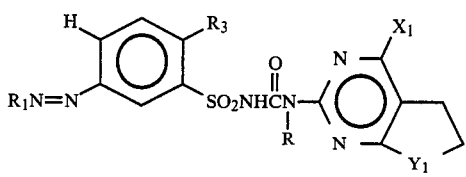 XI
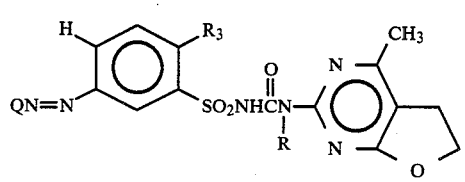 XII
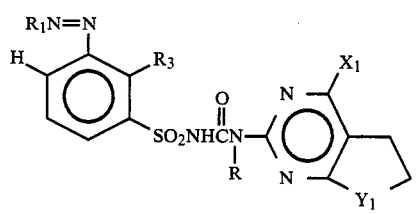 XIII
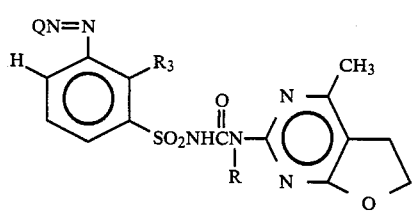 XIV
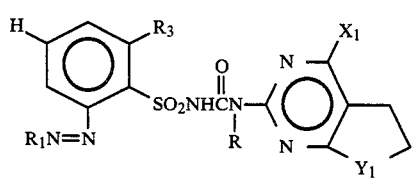 XV
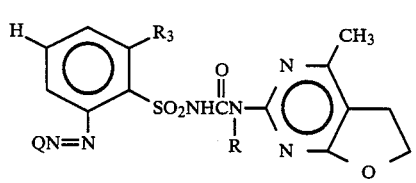 XVI
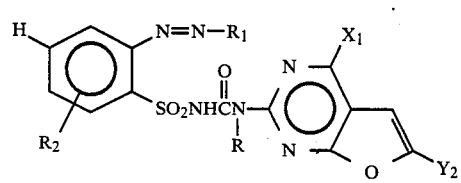 XVII
-continued
GENERAL FORMULAS FOR TABLES I-XXXII
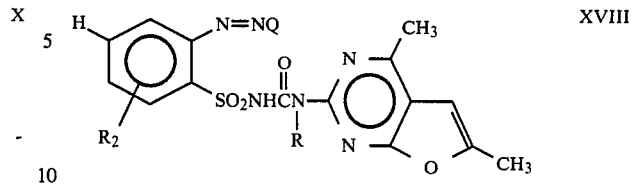 XVIII
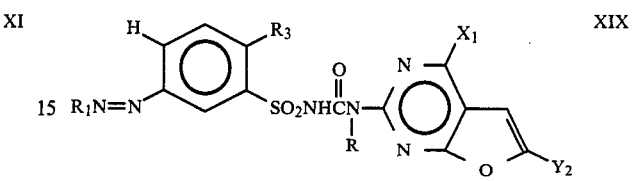 XIX
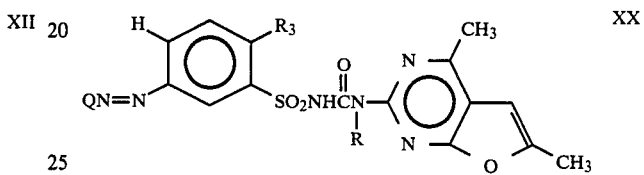 XX
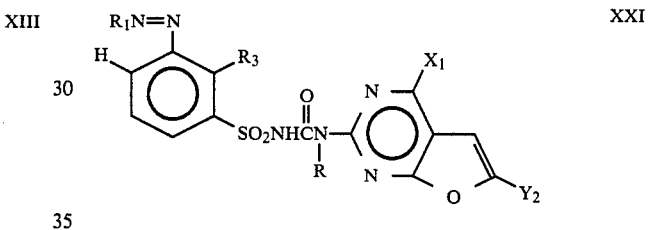 XXI
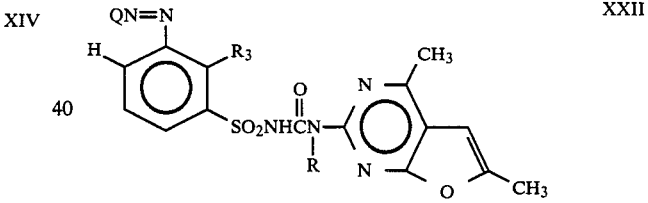 XXII
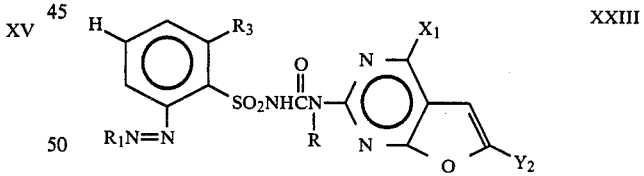 XXIII
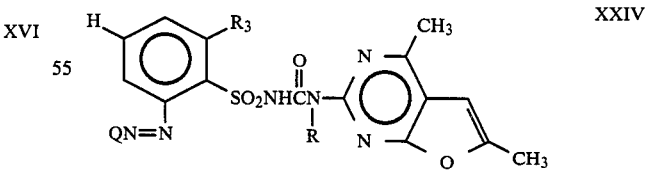 XXIV
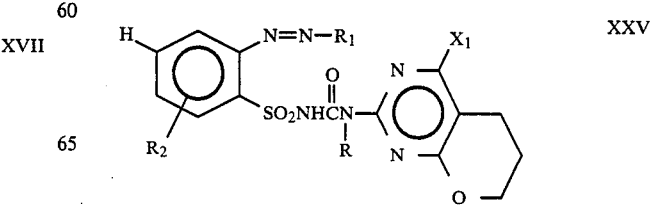 XXV -continued
GENERAL FORMULAS FOR TABLES I-XXXII

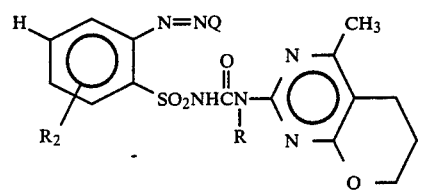   XXVI

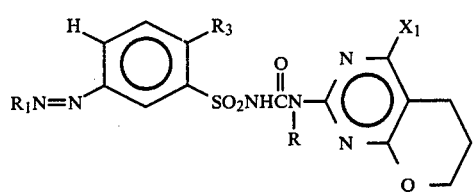   XXVII

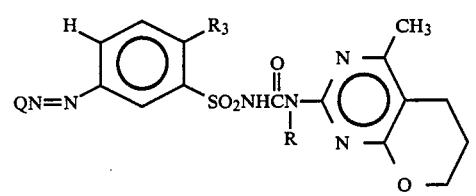   XXVIII

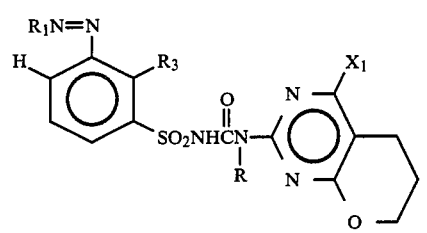   XXIX

-continued
GENERAL FORMULAS FOR TABLES I-XXXII

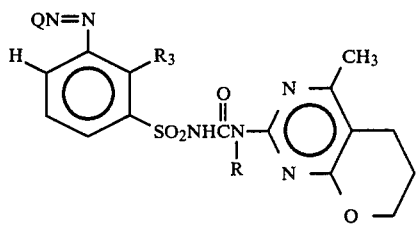   XXX

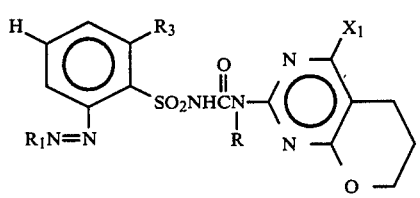   XXXI

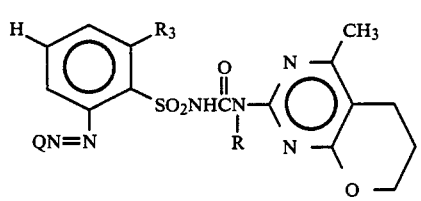   XXXII

TABLE I

General Formula I

| R | R₁ | R₂ | X | Y | Z | m.p. (°C.) |
|---|---|---|---|---|---|---|
| H | N(CH₃)₂ | H | CH₃ | CH₃ | CH | |
| H | N(CH₃)₂ | H | CH₃ | OCH₃ | CH | 158–160 |
| H | N(CH₃)₂ | H | OCH₃ | OCH₃ | CH | |
| H | N(CH₃)₂ | H | CH₃ | CH₃ | N | |
| H | N(CH₃)₂ | H | CH₃ | OCH₃ | N | |
| H | N(CH₃)₂ | H | OCH₃ | OCH₃ | N | |
| CH₃ | N(CH₃)₂ | H | OCH₃ | OCH₃ | CH | |
| H | N(CH₃)₂ | 6-F | OCH₃ | OCH₃ | CH | |
| H | N(CH₃)₂ | 6-Cl | OCH₃ | OCH₃ | CH | |
| H | N(CH₃)₂ | 6-Br | OCH₃ | OCH₃ | CH | |
| H | N(CH₃)₂ | 5-OCH₃ | OCH₃ | OCH₃ | CH | |
| H | N(CH₃)₂ | 5-F | OCH₃ | OCH₃ | CH | |
| H | N(CH₃)₂ | 3-OC₂H₅ | OCH₃ | OCH₃ | CH | |
| H | N(CH₃)₂ | 6-OCF₂H | OCH₃ | OCH₃ | CH | |
| H | N(CH₃)₂ | 5-SCH₃ | OCH₃ | OCH₃ | CH | |
| H | N(CH₃)₂ | 5-N(CH₃)₂ | OCH₃ | OCH₃ | CH | |
| H | N(CH₃)₂ | 5-NO₂ | OCH₃ | OCH₃ | CH | |
| H | N(CH₃)₂ | 6-CH₃ | OCH₃ | OCH₃ | CH | |
| H | N(CH₃)₂ | 6-CF₃ | OCH₃ | OCH₃ | CH | |
| H | N(C₂H₅)₂ | H | OCH₃ | OCH₃ | CH | |
| H | N(CH₃)C₄H₉ | H | OCH₃ | OCH₃ | CH | |
| H | N(CH₃)CH₂CF₃ | H | OCH₃ | OCH₃ | CH | |
| H | N—(CH₂CH₂Cl)₂ | H | OCH₃ | OCH₃ | CH | |
| H | N—(CH₃)CH₂CH₂Br | H | OCH₃ | OCH₃ | CH | |
| H | N(CH₃)CH₂CH=CH₂ | H | OCH₃ | OCH₃ | CH | |
| H | N(CH₃)CHCH=CHCH₃ (with CH₃ branch) | H | OCH₃ | OCH₃ | CH | |
| H | N(OH)CH₃ | H | OCH₃ | OCH₃ | CH | |
| H | N(OCH₃)CH₃ | H | OCH₃ | OCH₃ | CH | |
| H | N(CH₃)CH₂OH | H | OCH₃ | OCH₃ | CH | |
| H | N(CH₃)CH₂OCH₃ | H | OCH₃ | OCH₃ | CH | |
| H | N(CH₃)(cyclopropyl) | H | OCH₃ | OCH₃ | CH | |
| H | N(CH₃)(cyclopentyl) | H | OCH₃ | OCH₃ | CH | |

TABLE I-continued

General Formula I

| R | R₁ | R₂ | X | Y | Z | m.p. (°C.) |
|---|---|---|---|---|---|---|
| H | N—(CH₂)₄— (cyclic) | H | OCH₃ | OCH₃ | CH | |
| H | N—(CH₂)₅— (cyclic) | H | OCH₃ | OCH₃ | CH | |
| H | —N—CH₂CH₂OCH₂CH₂— (cyclic) | H | OCH₃ | OCH₃ | CH | |
| H | N(CH₃)CH₂CH₂OCH₃ | H | OCH₃ | OCH₃ | CH | |
| H | N(CH₂CH₂OCH₂CH₃)₂ | H | OCH₃ | OCH₃ | CH | |
| H | N(CH₃)OC₄H₉ | H | OCH₃ | OCH₃ | CH | |
| H | NHCN | H | OCH₃ | OCH₃ | CH | |
| H | N(CH₃)-(4,6-dimethyl-pyrimidin-2-yl) | H | OCH₃ | OCH₃ | CH | |
| H | P(O)(OCH₃)₂ | H | CH₃ | OCH₃ | CH | 155–156 |
| H | P(O)(CH₃)OCH₃ | H | OCH₃ | OCH₃ | CH | |
| H | P(O)(CH₂CF₃)OCH₃ | H | OCH₃ | OCH₃ | CH | |
| H | P(O)(OCH₃)CH₂CH=CH₂ | H | OCH₃ | OCH₃ | CH | |
| H | P(S)(CH₃)OCH₃ | H | OCH₃ | OCH₃ | CH | |
| H | P(O)(CH₃)SCH₃ | H | OCH₃ | OCH₃ | CH | |
| H | P(O)(CH₃)NHCH₃ | H | OCH₃ | OCH₃ | CH | |
| H | P(O)—(CH₂)₃—O— (cyclic) | H | OCH₃ | OCH₃ | CH | |
| H | P(O)(OCH₃)CH₂CH₂OCH₃ | H | OCH₃ | OCH₃ | CH | |
| H | P(O)(OCH₃)cyclopropyl | H | OCH₃ | OCH₃ | CH | |
| H | P⁺(C₆H₅)₃ | H | OCH₃ | OCH₃ | CH | |
| H | P⁺(n-C₄H₉)₃ | H | OCH₃ | OCH₃ | CH | |
| H | P⁺(CH₃)(C₂H₅)₂ | H | OCH₃ | OCH₃ | CH | |
| H | SCH₃ | H | OCH₃ | OCH₃ | CH | |
| H | S—n-C₄H₉ | H | OCH₃ | OCH₃ | CH | |
| H | SC₆H₅ | H | OCH₃ | OCH₃ | CH | |
| H | S—(3,4-C₆H₃Cl₂) | H | OCH₃ | OCH₃ | CH | |
| H | S—(4-C₆H₄Cl) | H | OCH₃ | OCH₃ | CH | |
| H | S—(2-C₆H₄Br) | H | OCH₃ | OCH₃ | CH | |
| H | SO₂CH₃ | H | OCH₃ | OCH₃ | CH | |
| H | SO₂—n-C₄H₉ | H | OCH₃ | OCH₃ | CH | |
| H | SO₂C₆H₅ | H | OCH₃ | OCH₃ | CH | |
| H | SO₂(3,4-C₆H₃Cl₂) | H | OCH₃ | OCH₃ | CH | |
| H | SO₂(4-C₆H₄Cl) | H | OCH₃ | OCH₃ | CH | |
| H | SO₂(2-C₆H₄Br) | H | OCH₃ | OCH₃ | CH | |
| H | CH₂NO₂ | H | OCH₃ | OCH₃ | CH | |
| H | CH(CH₃)NO₂ | H | OCH₃ | OCH₃ | CH | |
| H | C(CH₃)₂NO₂ | H | OCH₃ | OCH₃ | CH | |
| H | C(CH₃)(C₆H₅)NO₂ | H | OCH₃ | OCH₃ | CH | |
| H | CH(C₄H₉)NO₂ | H | OCH₃ | OCH₃ | CH | |
| H | CH(4-C₆H₄Cl)NO₂ | H | OCH₃ | OCH₃ | CH | |
| H | CH(CN)₂ | H | OCH₃ | OCH₃ | CH | |
| H | N(CH₃)₂ | H | OC₂H₅ | CH₃ | N | |
| H | N(CH₃)₂ | H | Cl | OCH₃ | CH | |
| H | N(CH₃)₂ | H | F | OCH₃ | CH | |
| H | N(CH₃)₂ | H | Br | OCH₃ | CH | |
| H | N(CH₃)₂ | H | OCF₂H | CH₃ | CH | |
| H | N(CH₃)₂ | H | CF₂H | CH₃ | CH | |
| H | N(CH₃)₂ | H | OCH₂CH₂F | CH₃ | CH | |
| H | N(CH₃)₂ | H | OCH₂CHF₂ | CH₃ | CH | |
| H | N(CH₃)₂ | H | OCH₂CF₃ | CH₃ | CH | |
| H | N(CH₃)₂ | H | CF₃ | OCH₃ | CH | |
| H | N(CH₃)₂ | H | OCH₃ | H | CH | |
| H | N(CH₃)₂ | H | OCH₃ | CH₂OCH₃ | CH | |
| H | N(CH₃)₂ | H | OCH₃ | NHCH₃ | N | |
| H | N(CH₃)₂ | H | OCH₃ | N(OCH₃)CH₃ | N | |
| H | N(CH₃)₂ | H | OCH₃ | N(CH₃)₂ | N | |
| H | N(CH₃)₂ | H | OCH₃ | CH₂CH₃ | CH | |

TABLE I-continued

General Formula I

| R | $R_1$ | $R_2$ | X | Y | Z | m.p. (°C.) |
|---|---|---|---|---|---|---|
| H | $N(CH_3)_2$ | H | $CF_3$ | $CF_3$ | CH | |
| H | $N(CH_3)_2$ | H | $CH_3$ | $SCH_3$ | CH | |
| H | $N(CH_3)_2$ | H | $CH_3$ | $OCH_2C\equiv CH$ | CH | |
| H | $N(CH_3)_2$ | H | $CH_3$ | $OCH_2CH=CH_2$ | CH | |
| H | $N(CH_3)_2$ | H | $CH_3$ | $CH_2OCH_2CH_3$ | CH | |
| H | $N(CH_3)_2$ | H | $CH_3$ | $OCH_2CH_2OCH_3$ | CH | |
| H | $N(CH_3)_2$ | H | $CH_3$ | $CH_2SCH_3$ | CH | |
| H | $N(CH_3)_2$ | H | $CH_3$ | CHO | CH | |
| H | $N(CH_3)_2$ | H | $CH_3$ | $COCH_3$ | CH | |
| H | $N(CH_3)_2$ | H | $CH_3$ | $CH(OCH_3)_2$ | CH | |
| H | $N(CH_3)_2$ | H | $CH_3$ | $CH-OCH_2CH_2O-$ | CH | |
| H | $N(CH_3)_2$ | H | $CH_3$ | $OCF_2H$ | CH | |
| H | $N(CH_3)_2$ | H | $CH_3$ | $SCF_2H$ | CH | |
| H | $N(CH_3)_2$ | H | $CH_3$ | —cyclopropyl | CH | |

TABLE II

General Formula II

| Q | R | $R_2$ | $R_4$ | $R_5$ | $R_6$ | $R_9$ | $R_{12}$ | $R_{13}$ | $R_{14}$ | X | m.p. (°C.) |
|---|---|---|---|---|---|---|---|---|---|---|---|
| Q-1 | H | H | — | — | — | — | $NHC_6H_5$ | — | — | $OCH_3$ | |
| Q-1 | H | H | — | — | — | — | $CH_3$ | — | — | $OCH_3$ | |
| Q-1 | H | H | — | — | — | — | $OCH_3$ | — | — | $OCH_3$ | |
| Q-1 | H | H | — | — | — | — | $O-t-C_4H_9$ | — | — | $OCH_3$ | |
| Q-1 | H | H | — | — | — | — | $NHCH_3$ | — | — | $OCH_3$ | |
| Q-2 | H | H | — | — | — | $CH_3$ | $CH_3$ | — | — | $OCH_3$ | |
| Q-2 | H | H | — | — | — | $C_6H_5$ | $CH_3$ | — | — | $OCH_3$ | |
| Q-2 | H | H | — | — | — | $CH_3$ | $OCH_3$ | — | — | $OCH_3$ | |
| Q-2 | H | H | — | — | — | $CH_3$ | $NHCH_3$ | — | — | $OCH_3$ | |
| Q-2 | H | H | — | — | — | $CH_3$ | $NHC_6H_5$ | — | — | $OCH_3$ | |
| Q-3 | H | H | — | — | — | — | $CH_3$ | — | — | $OCH_3$ | |
| Q-3 | H | H | — | — | — | — | $OCH_3$ | — | — | $OCH_3$ | |
| Q-3 | H | H | — | — | — | — | $O-t-C_4H_9$ | — | — | $OCH_3$ | |
| Q-3 | H | H | — | — | — | — | $NHCH_3$ | — | — | $OCH_3$ | |
| Q-4 | H | H | — | — | — | — | $CH_3$ | — | — | $OCH_3$ | |
| Q-4 | H | H | — | — | — | — | $OCH_3$ | — | — | $OCH_3$ | |
| Q-4 | H | H | — | — | — | — | $O-t-C_4H_9$ | — | — | $OCH_3$ | |
| Q-4 | H | H | — | — | — | — | $NHCH_3$ | — | — | $OCH_3$ | |
| Q-5 | H | H | — | — | — | — | — | — | — | $OCH_3$ | |
| Q-6 | H | H | — | — | — | — | — | — | — | $OCH_3$ | |
| Q-7 | H | H | — | — | — | — | — | — | — | $OCH_3$ | |
| Q-8 | H | H | — | — | — | — | — | H | H | $OCH_3$ | |
| Q-8 | H | H | — | — | — | — | — | H | $4-CH_3$ | $OCH_3$ | |
| Q-8 | H | H | — | — | — | — | — | H | $4-OCH_3$ | $OCH_3$ | |
| Q-8 | H | H | — | — | — | — | — | H | $3-SCH_3$ | $OCH_3$ | |
| Q-8 | H | H | — | — | — | — | — | 3-Cl | 4-Cl | $OCH_3$ | |
| Q-8 | H | H | — | — | — | — | — | H | $4-CO_2CH_3$ | $OCH_3$ | |
| Q-8 | H | H | — | — | — | — | — | $2-OCH_3$ | $5-OCH_3$ | $OCH_3$ | |
| Q-8 | H | H | — | — | — | — | — | 2-F | $5-NHCOCH_3$ | $OCH_3$ | |
| Q-9 | H | H | $CH_3$ | $CH_3$ | — | — | — | H | H | $CH_3$ | 210–211 |
| Q-9 | H | H | $CH_3$ | $CH_3$ | — | — | — | $2-NHCOCH_3$ | H | $OCH_3$ | |
| Q-9 | H | H | $CH_3$ | $CH_3$ | — | — | — | 2-Cl | H | $OCH_3$ | |
| Q-9 | H | H | $CH_3$ | $CH_3$ | — | — | — | $2-OCH_3$ | H | $OCH_3$ | |
| Q-9 | H | H | $CH_3$ | $CH_3$ | — | — | — | $2-SCH_3$ | H | $OCH_3$ | |
| Q-9 | H | H | $C_2H_5$ | $C_2H_5$ | — | — | — | H | H | $OCH_3$ | |
| Q-9 | H | H | $CH_3$ | $CH_2CH=CH_2$ | — | — | — | H | H | $OCH_3$ | |
| Q-9 | H | H | $CH_2CH_2Cl$ | $CH_2CH_2Cl$ | — | — | — | H | H | $OCH_3$ | |
| Q-9 | H | H | $CH_2CH_2OH$ | $CH_2CH_2OH$ | — | — | — | H | H | $OCH_3$ | |
| Q-9 | H | H | $-CH_2CH_2OCH_2CH_2-$ | | — | — | — | H | H | $OCH_3$ | |
| Q-10 | H | H | — | — | — | — | — | H | H | $OCH_3$ | |
| Q-10 | H | H | — | — | — | — | — | $2-NHCOCH_3$ | H | $OCH_3$ | |
| Q-10 | H | H | — | — | — | — | — | 2-Cl | H | $OCH_3$ | |
| Q-10 | H | H | — | — | — | — | — | $2-OCH_3$ | H | $OCH_3$ | |
| Q-10 | H | H | — | — | — | — | — | $2-SCH_3$ | H | $OCH_3$ | |
| Q-10 | H | H | — | — | — | — | — | $3-CO_2CH_3$ | H | $OCH_3$ | |
| Q-10 | H | H | — | — | — | — | — | 3-Cl | 5-Cl | $OCH_3$ | |
| Q-11 | H | H | $CH_3$ | $CH_3$ | — | — | — | H | H | $OCH_3$ | |
| Q-11 | H | H | $CH_3$ | $CH_3$ | — | — | — | $4-NHCOCH_3$ | H | $OCH_3$ | |
| Q-11 | H | H | $CH_3$ | $CH_3$ | — | — | — | 4-Cl | H | $OCH_3$ | |
| Q-11 | H | H | $CH_3$ | $CH_3$ | — | — | — | $4-OCH_3$ | H | $OCH_3$ | |
| Q-11 | H | H | $CH_3$ | $CH_3$ | — | — | — | $4-SCH_3$ | H | $OCH_3$ | |
| Q-11 | H | H | $C_2H_5$ | $C_2H_5$ | — | — | — | H | H | $OCH_3$ | |
| Q-11 | H | H | $CH_3$ | $CH_2CH=CH_2$ | — | — | — | H | H | $OCH_3$ | |
| Q-11 | H | H | $CH_2CH_2Cl$ | $CH_2CH_2Cl$ | — | — | — | H | H | $OCH_3$ | |
| Q-11 | H | H | $CH_2CH_2OH$ | $CHCH_2OH$ | — | — | — | H | H | $OCH_3$ | |

TABLE II-continued

General Formula II

| Q | R | R$_2$ | R$_4$ | R$_5$ | R$_6$ | R$_9$ | R$_{12}$ | R$_{13}$ | R$_{14}$ | X | m.p. (°C.) |
|---|---|---|---|---|---|---|---|---|---|---|---|
| Q-11 | H | H | | —CH$_2$CH$_2$OCH$_2$CH$_2$— | — | — | — | H | H | OCH$_3$ | |
| Q-12 | H | H | — | — | — | — | — | H | H | OCH$_3$ | |
| Q-12 | H | H | — | — | — | — | — | 4-NHCOCH$_3$ | H | OCH$_3$ | |
| Q-12 | H | H | — | — | — | — | — | 4-Cl | H | OCH$_3$ | |
| Q-12 | H | H | — | — | — | — | — | 4-OCH$_3$ | H | OCH$_3$ | |
| Q-12 | H | H | — | — | — | — | — | 4-SCH$_3$ | H | OCH$_3$ | |
| Q-12 | H | H | — | — | — | — | — | 4-CO$_2$CH$_3$ | H | OCH$_3$ | |
| Q-12 | H | H | — | — | — | — | — | 3-Cl | 5-Cl | OCH$_3$ | |
| Q-13 | H | H | — | — | CH$_3$ | H | — | — | — | OCH$_3$ | |
| Q-13 | H | H | — | — | C$_4$H$_9$ | CH$_3$ | — | — | — | OCH$_3$ | |
| Q-13 | H | H | — | — | CH$_3$ | C$_6$H$_5$ | — | — | — | OCH$_3$ | |
| Q-13 | H | H | — | — | CH$_3$ | 4-C$_6$H$_4$Cl | — | — | — | OCH$_3$ | |
| Q-13 | H | H | — | — | CH$_3$ | 2,4-C$_6$H$_3$Cl$_2$ | — | — | — | OCH$_3$ | |
| Q-13 | H | H | — | — | CH$_3$ | CH$_3$ | — | — | — | OCH$_3$ | |
| Q-14 | H | H | — | — | — | CH$_3$ | — | H | — | OCH$_3$ | |
| Q-14 | H | H | — | — | — | C$_6$H$_5$ | — | H | — | OCH$_3$ | |
| Q-14 | H | H | — | — | — | 4-C$_6$H$_4$Cl | — | H | — | OCH$_3$ | |
| Q-14 | H | H | — | — | — | CH$_3$ | — | CH$_3$ | — | OCH$_3$ | |
| Q-14 | H | H | — | — | — | CH$_3$ | — | Cl | — | OCH$_3$ | |
| Q-14 | H | H | — | — | — | CH$_3$ | — | OCH$_3$ | — | OCH$_3$ | |

TABLE III

General Formula III

| R | R$_1$ | R$_3$ | X | Y | Z | m.p. (°C.) |
|---|---|---|---|---|---|---|
| CH$_3$ | N(CH$_3$)$_2$ | CO$_2$CH$_3$ | OCH$_3$ | OCH$_3$ | CH | |
| H | N(CH$_3$)$_2$ | CO$_2$CH$_3$ | CH$_3$ | CH$_3$ | CH | |
| H | N(CH$_3$)$_2$ | CO$_2$CH$_3$ | OCH$_3$ | CH$_3$ | CH | |
| H | N(CH$_3$)$_2$ | CO$_2$CH$_3$ | OCH$_3$ | OCH$_3$ | CH | |
| H | N(CH$_3$)$_2$ | CO$_2$CH$_3$ | CH$_3$ | CH$_3$ | N | |
| H | N(CH$_3$)$_2$ | CO$_2$CH$_3$ | OCH$_3$ | CH$_3$ | N | |
| H | N(CH$_3$)$_2$ | CO$_2$CH$_3$ | OCH$_3$ | OCH$_3$ | N | |
| H | N(CH$_3$)$_2$ | NO$_2$ | CH$_3$ | OCH$_3$ | CH | |
| H | N(CH$_3$)$_2$ | NO$_2$ | OCH$_3$ | OCH$_3$ | CH | |
| H | N(CH$_3$)$_2$ | NO$_2$ | OCH$_3$ | CH$_3$ | N | |
| H | N(CH$_3$)$_2$ | NO$_2$ | OCH$_3$ | OCH$_3$ | N | |
| H | N(CH$_3$)$_2$ | CF$_3$ | CH$_3$ | OCH$_3$ | CH | |
| H | N(CH$_3$)$_2$ | CF$_3$ | OCH$_3$ | OCH$_3$ | CH | |
| H | N(CH$_3$)$_2$ | CF$_3$ | CH$_3$ | OCH$_3$ | N | |
| H | N(CH$_3$)$_2$ | CF$_3$ | OCH$_3$ | OCH$_3$ | N | |
| H | N(CH$_3$)$_2$ | OCH$_3$ | CH$_3$ | OCH$_3$ | CH | |
| H | N(CH$_3$)$_2$ | OCH$_3$ | OCH$_3$ | OCH$_3$ | CH | |
| H | N(CH$_3$)$_2$ | OCH$_3$ | CH$_3$ | OCH$_3$ | N | |
| H | N(CH$_3$)$_2$ | OCH$_3$ | OCH$_3$ | OCH$_3$ | N | |
| H | N(CH$_3$)$_2$ | SCH$_3$ | CH$_3$ | OCH$_3$ | CH | |
| H | N(CH$_3$)$_2$ | SCH$_3$ | OCH$_3$ | OCH$_3$ | CH | |
| H | N(CH$_3$)$_2$ | SCH$_3$ | CH$_3$ | OCH$_3$ | N | |
| H | N(CH$_3$)$_2$ | SCH$_3$ | OCH$_3$ | OCH$_3$ | N | |
| H | N(CH$_3$)$_2$ | SO$_2$N(CH$_3$)$_2$ | CH$_3$ | OCH$_3$ | CH | |
| H | N(CH$_3$)$_2$ | SO$_2$N(CH$_3$)$_2$ | OCH$_3$ | OCH$_3$ | CH | |
| H | N(CH$_3$)$_2$ | SO$_2$N(CH$_3$)$_2$ | CH$_3$ | OCH$_3$ | N | |
| H | N(CH$_3$)$_2$ | SO$_2$N(CH$_3$)$_2$ | OCH$_3$ | OCH$_3$ | N | |
| H | N(CH$_3$)$_2$ | SO$_2$CH$_3$ | CH$_3$ | OCH$_3$ | CH | |
| H | N(CH$_3$)$_2$ | SO$_2$CH$_3$ | OCH$_3$ | OCH$_3$ | CH | |
| H | N(CH$_3$)$_2$ | SO$_2$CH$_3$ | CH$_3$ | OCH$_3$ | N | |
| H | N(CH$_3$)$_2$ | SO$_2$CH$_3$ | OCH$_3$ | OCH$_3$ | N | |
| H | N(CH$_3$)$_2$ | OCH$_2$CH$_2$Cl | OCH$_3$ | OCH$_3$ | CH | |
| H | N(CH$_3$)$_2$ | OCH$_2$CH$_2$Cl | CH$_3$ | OCH$_3$ | N | |
| H | N(CH$_3$)$_2$ | OSO$_2$CH$_3$ | CH$_3$ | OCH$_3$ | CH | |
| H | N(CH$_3$)$_2$ | OSO$_2$CH$_3$ | OCH$_3$ | OCH$_3$ | CH | |
| H | N(CH$_3$)$_2$ | OSO$_2$CH$_3$ | OCH$_3$ | OCH$_3$ | N | |
| H | N(CH$_3$)$_2$ | —CH$_2$OCH$_3$ | CH$_3$ | OCH$_3$ | CH | |
| H | N(CH$_3$)$_2$ | —CH$_2$OCH$_3$ | OCH$_3$ | OCH$_3$ | CH | |
| H | N(CH$_3$)$_2$ | —CH$_2$OCH$_3$ | CH$_3$ | OCH$_3$ | N | |
| H | N(CH$_3$)$_2$ | —CH$_2$OCH$_3$ | OCH$_3$ | OCH$_3$ | N | |
| H | N(CH$_3$)$_2$ | OCH$_2$CH=CH$_2$ | CH$_3$ | OCH$_3$ | CH | |
| H | N(CH$_3$)$_2$ | OCH$_2$CH=CH$_2$ | OCH$_3$ | OCH$_3$ | CH | |
| H | N(CH$_3$)$_2$ | OCH$_2$CH=CH$_2$ | CH$_3$ | OCH$_3$ | N | |
| H | N(CH$_3$)$_2$ | OCH$_2$CH=CH$_2$ | OCH$_3$ | OCH$_3$ | N | |
| H | N(CH$_3$)$_2$ | CH$_3$ | CH$_3$ | OCH$_3$ | CH | |
| H | N(CH$_3$)$_2$ | CH$_3$ | OCH$_3$ | OCH$_3$ | CH | |
| H | N(CH$_3$)$_2$ | CH$_3$ | CH$_3$ | OCH$_3$ | N | |
| H | N(CH$_3$)$_2$ | CH$_3$ | OCH$_3$ | OCH$_3$ | N | |
| H | N(CH$_3$)$_2$ | Cl | CH$_3$ | OCH$_3$ | CH | |
| H | N(CH$_3$)$_2$ | Cl | OCH$_3$ | OCH$_3$ | CH | |
| H | N(CH$_3$)$_2$ | Cl | CH$_3$ | OCH$_3$ | N | |
| H | N(CH$_3$)$_2$ | Cl | OCH$_3$ | OCH$_3$ | N | |

TABLE III-continued

General Formula III

| R | R₁ | R₃ | X | Y | Z | m.p. (°C.) |
|---|---|---|---|---|---|---|
| H | N(CH₃)₂ | Br | CH₃ | OCH₃ | CH | |
| H | N(CH₃)₂ | Br | OCH₃ | OCH₃ | CH | |
| H | N(CH₃)₂ | Br | CH₃ | OCH₃ | N | |
| H | N(CH₃)₂ | Br | OCH₃ | OCH₃ | N | |
| H | N(CH₃)₂ | F | CH₃ | OCH₃ | CH | |
| H | N(CH₃)₂ | F | OCH₃ | OCH₃ | CH | |
| H | N(CH₃)₂ | F | CH₃ | OCH₃ | N | |
| H | N(CH₃)₂ | F | OCH₃ | OCH₃ | N | |
| H | N(CH₃)₂ | H | OCH₃ | OCH₃ | CH | |
| H | N(CH₃)₂ | H | CH₃ | OCH₃ | N | |
| H | N(CH₃)₂ | n-C₄H₉ | OCH₃ | OCH₃ | CH | |
| H | N(CH₃)₂ | CO₂CH₂CH₃ | OCH₃ | OCH₃ | CH | |
| H | N(CH₃)₂ | —CO₂—i-C₃H₇ | OCH₃ | OCH₃ | CH | |
| H | N(CH₃)₂ | —CO₂—CH₂CH=CH₂ | OCH₃ | OCH₃ | CH | |
| H | N(CH₃)₂ | —CO₂CH₂CH₂Cl | OCH₃ | OCH₃ | CH | |
| H | N(CH₃)₂ | —CO₂CH₂CH₂OCH₃ | OCH₃ | OCH₃ | CH | |
| H | N(CH₃)₂ | —OC₄H₉ | OCH₃ | OCH₃ | CH | |
| H | N(CH₃)₂ | —S—C₄H₉ | OCH₃ | OCH₃ | CH | |
| H | N(CH₃)₂ | SO₂N(C₂H₅)₂ | OCH₃ | OCH₃ | CH | |
| H | N(CH₃)₂ | SO₂CH₂CH₃ | OCH₃ | OCH₃ | CH | |
| H | N(CH₃)₂ | SO₂C₄H₉ | OCH₃ | OCH₃ | CH | |
| H | N(CH₃)₂ | OCH₂CH₂CH₂CH₂Br | OCH₃ | OCH₃ | CH | |
| H | N(CH₃)₂ | OSO₂C₄H₉ | OCH₃ | OCH₃ | CH | |
| H | N(C₂H₅)₂ | CO₂CH₃ | OCH₃ | OCH₃ | CH | |
| H | N(CH₃)C₄H₉ | CO₂CH₃ | OCH₃ | OCH₃ | CH | |
| H | N(CH₃)CH₂CF₃ | CO₂CH₃ | OCH₃ | OCH₃ | CH | |
| H | N—(CH₂CH₂Cl)₂ | CO₂CH₃ | OCH₃ | OCH₃ | CH | |
| H | N—(CH₃)CH₂CH₂Br | CO₂CH₃ | OCH₃ | OCH₃ | CH | |
| H | N(CH₃)CH₂CH=CH₂ | CO₂CH₃ | OCH₃ | OCH₃ | CH | |
| H | N(CH₃)CHCH=CHCH₃ (with CH₃ branch) | CO₂CH₃ | OCH₃ | OCH₃ | CH | |
| H | N(OH)CH₃ | CO₂CH₃ | OCH₃ | OCH₃ | CH | |
| H | N(OCH₃)CH₃ | CO₂CH₃ | OCH₃ | OCH₃ | CH | |
| H | N(CH₃)CH₂OH | CO₂CH₃ | OCH₃ | OCH₃ | CH | |
| H | N(CH₃)CH₂OCH₃ | CO₂CH₃ | OCH₃ | OCH₃ | CH | |
| H | N(CH₃)(cyclopropyl) | CO₂CH₃ | OCH₃ | OCH₃ | CH | |
| H | N(CH₃)(cyclopentyl) | CO₂CH₃ | OCH₃ | OCH₃ | CH | |
| H | N—(CH₂)₄— (cyclic) | CO₂CH₃ | OCH₃ | OCH₃ | CH | |
| H | N—(CH₂)₅— (cyclic) | CO₂CH₃ | OCH₃ | OCH₃ | CH | |
| H | —N—CH₂CH₂OCH₂CH₂— (cyclic) | CO₂CH₃ | OCH₃ | OCH₃ | CH | |
| H | N(CH₃)CH₂CH₂OCH₃ | CO₂CH₃ | OCH₃ | OCH₃ | CH | |
| H | N(CH₂CH₂OCH₂CH₃)₂ | CO₂CH₃ | OCH₃ | OCH₃ | CH | |
| H | N(CH₃)OC₄H₉ | CO₂CH₃ | OCH₃ | OCH₃ | CH | |
| H | NHCN | CO₂CH₃ | OCH₃ | OCH₃ | CH | |
| H | N(CH₃)-(4,6-dimethylpyrimidin-2-yl) | CO₂CH₃ | OCH₃ | OCH₃ | CH | |
| H | P(O)(OCH₃)₂ | CO₂CH₃ | CH₃ | OCH₃ | CH | |
| H | P(O)(CH₃)OCH₃ | CO₂CH₃ | OCH₃ | OCH₃ | CH | |
| H | P(O)(CH₂CF₃)OCH₃ | CO₂CH₃ | OCH₃ | OCH₃ | CH | |
| H | P(O)(OCH₃)CH₂CH=CH₂ | CO₂CH₃ | OCH₃ | OCH₃ | CH | |
| H | P(S)(CH₃)OCH₃ | CO₂CH₃ | OCH₃ | OCH₃ | CH | |
| H | P(O)(CH₃)SCH₃ | CO₂CH₃ | OCH₃ | OCH₃ | CH | |
| H | P(O)(CH₃)NHCH₃ | CO₂CH₃ | OCH₃ | OCH₃ | CH | |
| H | P(O)—(CH₂)₃O— (cyclic) | CO₂CH₃ | OCH₃ | OCH₃ | CH | |

TABLE III-continued

General Formula III

| R | $R_1$ | $R_3$ | X | Y | Z | m.p. (°C.) |
|---|---|---|---|---|---|---|
| H | $P(O)(OCH_3)CH_2CH_2OCH_3$ | $CO_2CH_3$ | $OCH_3$ | $OCH_3$ | CH | |
| H | $P(O)(OCH_3)$cyclopropyl | $CO_2CH_3$ | $OCH_3$ | $OCH_3$ | CH | |
| H | $P^+(C_6H_5)_3$ | $CO_2CH_3$ | $OCH_3$ | $OCH_3$ | CH | |
| H | $P^+(\underline{n}\text{-}C_4H_9)_3$ | $CO_2CH_3$ | $OCH_3$ | $OCH_3$ | CH | |
| H | $P^+(CH_3)(C_2H_5)_2$ | $CO_2CH_3$ | $OCH_3$ | $OCH_3$ | CH | |
| H | $SCH_3$ | $CO_2CH_3$ | $OCH_3$ | $OCH_3$ | CH | |
| H | $S\text{—}\underline{n}\text{-}C_4H_9$ | $CO_2CH_3$ | $OCH_3$ | $OCH_3$ | CH | |
| H | $SC_6H_5$ | $CO_2CH_3$ | $OCH_3$ | $OCH_3$ | CH | |
| H | $S\text{—}(3,4\text{-}C_6H_3Cl_2)$ | $CO_2CH_3$ | $OCH_3$ | $OCH_3$ | CH | |
| H | $S\text{—}(4\text{-}C_6H_4Cl)$ | $CO_2CH_3$ | $OCH_3$ | $OCH_3$ | CH | |
| H | $S\text{—}(2\text{-}C_6H_4Br)$ | $CO_2CH_3$ | $OCH_3$ | $OCH_3$ | CH | |
| H | $SO_2CH_3$ | $CO_2CH_3$ | $OCH_3$ | $OCH_3$ | CH | |
| H | $SO_2\text{—}\underline{n}\text{-}C_4H_9$ | $CO_2CH_3$ | $OCH_3$ | $OCH_3$ | CH | |
| H | $SO_2C_6H_5$ | $CO_2CH_3$ | $OCH_3$ | $OCH_3$ | CH | |
| H | $SO_2(3,4\text{-}C_6H_3Cl_2)$ | $CO_2CH_3$ | $OCH_3$ | $OCH_3$ | CH | |
| H | $SO_2(4\text{-}C_6H_4Cl)$ | $CO_2CH_3$ | $OCH_3$ | $OCH_3$ | CH | |
| H | $SO_2(2\text{-}C_6H_4Br)$ | $CO_2CH_3$ | $OCH_3$ | $OCH_3$ | CH | |
| H | $CH_2NO_2$ | $CO_2CH_3$ | $OCH_3$ | $OCH_3$ | CH | |
| H | $CH(CH_3)NO_2$ | $CO_2CH_3$ | $OCH_3$ | $OCH_3$ | CH | |
| H | $C(CH_3)_2NO_2$ | $CO_2CH_3$ | $OCH_3$ | $OCH_3$ | CH | |
| H | $C(CH_3)(C_6H_5)NO_2$ | $CO_2CH_3$ | $OCH_3$ | $OCH_3$ | CH | |
| H | $CH(C_4H_9)NO_2$ | $CO_2CH_3$ | $OCH_3$ | $OCH_3$ | CH | |
| H | $CH(4\text{-}C_6H_4Cl)NO_2$ | $CO_2CH_3$ | $OCH_3$ | $OCH_3$ | CH | |
| H | $CH(CN)_2$ | $CO_2CH_3$ | $OCH_3$ | $OCH_3$ | CH | |
| H | $N(CH_3)_2$ | $CO_2CH_3$ | $OC_2H_5$ | $CH_3$ | N | |
| H | $N(CH_3)_2$ | $CO_2CH_3$ | Cl | $OCH_3$ | CH | |
| H | $N(CH_3)_2$ | $CO_2CH_3$ | F | $OCH_3$ | CH | |
| H | $N(CH_3)_2$ | $CO_2CH_3$ | Br | $OCH_3$ | CH | |
| H | $N(CH_3)_2$ | $CO_2CH_3$ | $OCF_2H$ | $CH_3$ | CH | |
| H | $N(CH_3)_2$ | $CO_2CH_3$ | $CF_2H$ | $CH_3$ | CH | |
| H | $N(CH_3)_2$ | $CO_2CH_3$ | $OCH_2CH_2F$ | $CH_3$ | CH | |
| H | $N(CH_3)_2$ | $CO_2CH_3$ | $OCH_2CHF_2$ | $CH_3$ | CH | |
| H | $N(CH_3)_2$ | $CO_2CH_3$ | $OCH_2CF_3$ | $CH_3$ | CH | |
| H | $N(CH_3)_2$ | $CO_2CH_3$ | $CF_3$ | $OCH_3$ | CH | |
| H | $N(CH_3)_2$ | $CO_2CH_3$ | $OCH_3$ | H | CH | |
| H | $N(CH_3)_2$ | $CO_2CH_3$ | $OCH_3$ | $CH_2OCH_3$ | CH | |
| H | $N(CH_3)_2$ | $CO_2CH_3$ | $OCH_3$ | $NHCH_3$ | N | |
| H | $N(CH_3)_2$ | $CO_2CH_3$ | $OCH_3$ | $N(CH_3)OCH_3$ | N | |
| H | $N(CH_3)_2$ | $CO_2CH_3$ | $OCH_3$ | $N(CH_3)_2$ | N | |
| H | $N(CH_3)_2$ | $CO_2CH_3$ | $OCH_3$ | $CH_2CH_3$ | CH | |
| H | $N(CH_3)_2$ | $CO_2CH_3$ | $CF_3$ | $CF_3$ | CH | |
| H | $N(CH_3)_2$ | $CO_2CH_3$ | $CH_3$ | $SCH_3$ | CH | |
| H | $N(CH_3)_2$ | $CO_2CH_3$ | $CH_3$ | $OCH_2C\equiv CH$ | CH | |
| H | $N(CH_3)_2$ | $CO_2CH_3$ | $CH_3$ | $OCH_2CH=CH_2$ | CH | |
| H | $N(CH_3)_2$ | $CO_2CH_3$ | $CH_3$ | $CH_2OCH_2CH_3$ | CH | |
| H | $N(CH_3)_2$ | $CO_2CH_3$ | $OCH_3$ | $OCH_2CH_2OCH_3$ | CH | |
| H | $N(CH_3)_2$ | $CO_2CH_3$ | $OCH_3$ | $CH_2SCH_3$ | CH | |
| H | $N(CH_3)_2$ | $CO_2CH_3$ | CHO | CH | | |
| H | $N(CH_3)_2$ | $CO_2CH_3$ | $CH_3$ | $COCH_3$ | CH | |
| H | $N(CH_3)_2$ | $CO_2CH_3$ | $CH_3$ | $CH(OCH_3)_2$ | CH | |
| H | $N(CH_3)_2$ | $CO_2CH_3$ | $CH_3$ | $CH\text{—}OCH_2CH_2O\text{—}$ | CH | |
| H | $N(CH_3)_2$ | $CO_2CH_3$ | $CH_3$ | $OCF_2H$ | CH | |
| H | $N(CH_3)_2$ | $CO_2CH_3$ | $CH_3$ | $SCF_2H$ | CH | |
| H | $N(CH_3)_2$ | $CO_2CH_3$ | $CH_3$ | —cyclopropyl | CH | |

TABLE IV

General Formula IV

| Q | R | $R_2$ | $R_4$ | $R_5$ | $R_6$ | $R_9$ | $R_{12}$ | $R_{13}$ | $R_{14}$ | m.p. (° C.) |
|---|---|---|---|---|---|---|---|---|---|---|
| Q-1 | H | $CO_2CH_3$ | — | — | — | — | $NHC_6H_5$ | — | — | |
| Q-1 | H | $CO_2CH_3$ | — | — | — | — | $CH_3$ | — | — | |
| Q-1 | H | $CO_2CH_3$ | — | — | — | — | $OCH_3$ | — | — | |
| Q-1 | H | $CO_2CH_3$ | — | — | — | — | $O\text{—}\underline{t}\text{-}C_4H_9$ | — | — | |
| Q-1 | H | $CO_2CH_3$ | — | — | — | — | $NHCH_3$ | — | — | |
| Q-2 | H | $CO_2CH_3$ | — | — | — | $CH_3$ | $CH_3$ | — | — | |
| Q-2 | H | $CO_2CH_3$ | — | — | — | $C_6H_5$ | $CH_3$ | — | — | |
| Q-2 | H | $CO_2CH_3$ | — | — | — | $CH_3$ | $OCH_3$ | — | — | |
| Q-2 | H | $CO_2CH_3$ | — | — | — | $CH_3$ | $NHCH_3$ | — | — | |
| Q-2 | H | $CO_2CH_3$ | — | — | — | $CH_3$ | $NHC_6H_5$ | — | — | |
| Q-3 | H | $CO_2CH_3$ | — | — | — | — | $CH_3$ | — | — | |
| Q-3 | H | $CO_2CH_3$ | — | — | — | — | $OCH_3$ | — | — | |
| Q-3 | H | $CO_2CH_3$ | — | — | — | — | $O\text{—}\underline{t}\text{-}C_4H_9$ | — | — | |
| Q-3 | H | $CO_2CH_3$ | — | — | — | — | $NHCH_3$ | — | — | |
| Q-4 | H | $CO_2CH_3$ | — | — | — | — | $CH_3$ | — | — | |

TABLE IV-continued

General Formula IV

| Q | R | $R_2$ | $R_4$ | $R_5$ | $R_6$ | $R_9$ | $R_{12}$ | $R_{13}$ | $R_{14}$ | m.p. (°C.) |
|---|---|---|---|---|---|---|---|---|---|---|
| Q-4 | H | $CO_2CH_3$ | — | — | — | — | $OCH_3$ | — | — | |
| Q-4 | H | $CO_2CH_3$ | — | — | — | — | $O-\underline{t}-C_4H_9$ | — | — | |
| Q-4 | H | $CO_2CH_3$ | — | — | — | — | $NHCH_3$ | — | — | |
| Q-5 | H | $CO_2CH_3$ | — | — | — | — | — | — | — | |
| Q-6 | H | $CO_2CH_3$ | — | — | — | — | — | — | — | |
| Q-7 | H | $CO_2CH_3$ | — | — | — | — | — | — | — | |
| Q-8 | H | $CO_2CH_3$ | — | — | — | — | — | H | H | |
| Q-8 | H | $CO_2CH_3$ | — | — | — | — | — | H | $4-CH_3$ | |
| Q-8 | H | $CO_2CH_3$ | — | — | — | — | — | H | $4-OCH_3$ | |
| Q-8 | H | $CO_2CH_3$ | — | — | — | — | — | H | $3-SCH_3$ | |
| Q-8 | H | $CO_2CH_3$ | — | — | — | — | — | 3-Cl | 4-Cl | |
| Q-8 | H | $CO_2CH_3$ | — | — | — | — | — | H | $4-CO_2CH_3$ | |
| Q-8 | H | $CO_2CH_3$ | — | — | — | — | — | $2-OCH_3$ | $5-OCH_3$ | |
| Q-8 | H | $CO_2CH_3$ | — | — | — | — | — | 2-F | $5-NHCOCH_3$ | |
| Q-9 | H | $CO_2CH_3$ | $CH_3$ | $CH_3$ | — | — | — | H | H | 221–231 |
| Q-9 | H | $CO_2CH_3$ | $CH_3$ | $CH_3$ | — | — | — | $2-NHCOCH_3$ | H | |
| Q-9 | H | $CO_2CH_3$ | $CH_3$ | $CH_3$ | — | — | — | 2-Cl | H | |
| Q-9 | H | $CO_2CH_3$ | $CH_3$ | $CH_3$ | — | — | — | $2-OCH_3$ | H | |
| Q-9 | H | $CO_2CH_3$ | $CH_3$ | $CH_3$ | — | — | — | $2-SCH_3$ | H | |
| Q-9 | H | $CO_2CH_3$ | $C_2H_5$ | $C_2H_5$ | — | — | — | H | H | |
| Q-9 | H | $CO_2CH_3$ | $CH_3$ | $CH_2CH=CH_2$ | — | — | — | H | H | |
| Q-9 | H | $CO_2CH_3$ | $CH_2CH_2Cl$ | $CH_2CH_2Cl$ | — | — | — | H | H | |
| Q-9 | H | $CO_2CH_3$ | $CH_2CH_2OH$ | $CH_2CH_2OH$ | — | — | — | H | H | |
| Q-9 | H | $CO_2CH_3$ | $-CH_2CH_2OCH_2CH_2-$ | | — | — | — | H | H | |
| Q-10 | H | $CO_2CH_3$ | — | — | — | — | — | H | H | |
| Q-10 | H | $CO_2CH_3$ | — | — | — | — | — | $2-NHCOCH_3$ | H | |
| Q-10 | H | $CO_2CH_3$ | — | — | — | — | — | 2-Cl | H | |
| Q-10 | H | $CO_2CH_3$ | — | — | — | — | — | $2-OCH_3$ | H | |
| Q-10 | H | $CO_2CH_3$ | — | — | — | — | — | $2-SCH_3$ | H | |
| Q-10 | H | $CO_2CH_3$ | — | — | — | — | — | $3-CO_2CH_3$ | H | |
| Q-10 | H | $CO_2CH_3$ | — | — | — | — | — | 3-Cl | 5-Cl | |
| Q-11 | H | $CO_2CH_3$ | $CH_3$ | $CH_3$ | — | — | — | H | H | |
| Q-11 | H | $CO_2CH_3$ | $CH_3$ | $CH_3$ | — | — | — | $4-NHCOCH_3$ | H | |
| Q-11 | H | $CO_2CH_3$ | $CH_3$ | $CH_3$ | — | — | — | 4-Cl | H | |
| Q-11 | H | $CO_2CH_3$ | $CH_3$ | $CH_3$ | — | — | — | $4-OCH_3$ | H | |
| Q-11 | H | $CO_2CH_3$ | $CH_3$ | $CH_3$ | — | — | — | $4-SCH_3$ | H | |
| Q-11 | H | $CO_2CH_3$ | $C_2H_5$ | $C_2H_5$ | — | — | — | H | H | |
| Q-11 | H | $CO_2CH_3$ | $CH_3$ | $CH_2CH=CH_2$ | — | — | — | H | H | |
| Q-11 | H | $CO_2CH_3$ | $CH_2CH_2Cl$ | $CH_2CH_2Cl$ | — | — | — | H | H | |
| Q-11 | H | $CO_2CH_3$ | $CH_2CH_2OH$ | $CH_2CH_2OH$ | — | — | — | H | H | |
| Q-11 | H | $CO_2CH_3$ | $-CH_2CH_2OCH_2CH_2-$ | | — | — | — | H | H | |
| Q-12 | H | $CO_2CH_3$ | — | — | — | — | — | H | H | |
| Q-12 | H | $CO_2CH_3$ | — | — | — | — | — | $4-NHCOCH_3$ | H | |
| Q-12 | H | $CO_2CH_3$ | — | — | — | — | — | 4-Cl | H | |
| Q-12 | H | $CO_2CH_3$ | — | — | — | — | — | $4-OCH_3$ | H | |
| Q-12 | H | $CO_2CH_3$ | — | — | — | — | — | $4-SCH_3$ | H | |
| Q-12 | H | $CO_2CH_3$ | — | — | — | — | — | $4-CO_2CH_3$ | H | |
| Q-12 | H | $CO_2CH_3$ | — | — | — | — | — | 3-Cl | 5-Cl | |
| Q-13 | H | $CO_2CH_3$ | — | — | $CH_3$ | H | — | — | — | |
| Q-13 | H | $CO_2CH_3$ | — | — | $C_4H_9$ | $CH_3$ | — | — | — | |
| Q-13 | H | $CO_2CH_3$ | — | — | $CH_3$ | $C_6H_5$ | — | — | — | |
| Q-13 | H | $CO_2CH_3$ | — | — | $CH_3$ | $4-C_6H_4Cl$ | — | — | — | |
| Q-13 | H | $CO_2CH_3$ | — | — | $CH_3$ | $2,4-C_6H_3Cl_2$ | — | — | — | |
| Q-13 | H | $CO_2CH_3$ | — | — | $CH_3$ | $CH_3$ | — | — | — | |
| Q-14 | H | $CO_2CH_3$ | — | — | — | $CH_3$ | — | H | — | |
| Q-14 | H | $CO_2CH_3$ | — | — | — | $C_6H_5$ | — | H | — | |
| Q-14 | H | $CO_2CH_3$ | — | — | — | $4-C_6H_4Cl$ | — | H | — | |
| Q-14 | H | $CO_2CH_3$ | — | — | — | $CH_3$ | — | $CH_3$ | — | |
| Q-14 | H | $CO_2CH_3$ | — | — | — | $CH_3$ | — | Cl | — | |
| Q-14 | H | $CO_2CH_3$ | — | — | — | $CH_3$ | — | $OCH_3$ | — | |

TABLE V

General Formula V

| R | $R_1$ | $R_3$ | X | Y | Z | m.p. (°C.) |
|---|---|---|---|---|---|---|
| $CH_3$ | $N(CH_3)_2$ | $CO_2CH_3$ | $OCH_3$ | $OCH_3$ | CH | |
| H | $N(CH_3)_2$ | $CO_2CH_3$ | $CH_3$ | $CH_3$ | CH | |
| H | $N(CH_3)_2$ | $CO_2CH_3$ | $OCH_3$ | $CH_3$ | CH | |
| H | $N(CH_3)_2$ | $CO_2CH_3$ | $OCH_3$ | $OCH_3$ | CH | |
| H | $N(CH_3)_2$ | $CO_2CH_3$ | $CH_3$ | $CH_3$ | N | |
| H | $N(CH_3)_2$ | $CO_2CH_3$ | $OCH_3$ | $CH_3$ | N | |
| H | $N(CH_3)_2$ | $CO_2CH_3$ | $OCH_3$ | $OCH_3$ | N | |
| H | $N(CH_3)_2$ | $NO_2$ | $CH_3$ | $OCH_3$ | CH | |
| H | $N(CH_3)_2$ | $NO_2$ | $OCH_3$ | $OCH_3$ | CH | |
| H | $N(CH_3)_2$ | $NO_2$ | $OCH_3$ | $CH_3$ | N | |
| H | $N(CH_3)_2$ | $NO_2$ | $OCH_3$ | $OCH_3$ | N | |
| H | $N(CH_3)_2$ | $CF_3$ | $CH_3$ | $OCH_3$ | CH | |
| H | $N(CH_3)_2$ | $CF_3$ | $OCH_3$ | $OCH_3$ | CH | |

TABLE V-continued

General Formula V

| R | R₁ | R₃ | X | Y | Z | m.p. (°C.) |
|---|---|---|---|---|---|---|
| H | N(CH₃)₂ | CF₃ | CH₃ | OCH₃ | N | |
| H | N(CH₃)₂ | CF₃ | OCH₃ | OCH₃ | N | |
| H | N(CH₃)₂ | OCH₃ | CH₃ | OCH₃ | CH | |
| H | N(CH₃)₂ | OCH₃ | OCH₃ | OCH₃ | CH | |
| H | N(CH₃)₂ | OCH₃ | CH₃ | OCH₃ | N | |
| H | N(CH₃)₂ | OCH₃ | OCH₃ | OCH₃ | N | |
| H | N(CH₃)₂ | SCH₃ | CH₃ | OCH₃ | CH | |
| H | N(CH₃)₂ | SCH₃ | OCH₃ | OCH₃ | CH | |
| H | N(CH₃)₂ | SCH₃ | CH₃ | OCH₃ | N | |
| H | N(CH₃)₂ | SCH₃ | OCH₃ | OCH₃ | N | |
| H | N(CH₃)₂ | SO₂N(CH₃)₂ | CH₃ | OCH₃ | CH | |
| H | N(CH₃)₂ | SO₂N(CH₃)₂ | OCH₃ | OCH₃ | CH | |
| H | N(CH₃)₂ | SO₂N(CH₃)₂ | CH₃ | OCH₃ | N | |
| H | N(CH₃)₂ | SO₂N(CH₃)₂ | OCH₃ | OCH₃ | N | |
| H | N(CH₃)₂ | SO₂CH₃ | CH₃ | OCH₃ | CH | |
| H | N(CH₃)₂ | SO₂CH₃ | OCH₃ | OCH₃ | CH | |
| H | N(CH₃)₂ | SO₂CH₃ | CH₃ | OCH₃ | N | |
| H | N(CH₃)₂ | SO₂CH₃ | OCH₃ | OCH₃ | N | |
| H | N(CH₃)₂ | OCH₂CH₂Cl | OCH₃ | OCH₃ | CH | |
| H | N(CH₃)₂ | OCH₂CH₂Cl | CH₃ | OCH₃ | N | |
| H | N(CH₃)₂ | OSO₂CH₃ | CH₃ | OCH₃ | CH | |
| H | N(CH₃)₂ | OSO₂CH₃ | OCH₃ | OCH₃ | CH | |
| H | N(CH₃)₂ | OSO₂CH₃ | CH₃ | OCH₃ | N | |
| H | N(CH₃)₂ | OSO₂CH₃ | OCH₃ | OCH₃ | N | |
| H | N(CH₃)₂ | —CH₂OCH₃ | CH₃ | OCH₃ | CH | |
| H | N(CH₃)₂ | —CH₂OCH₃ | OCH₃ | OCH₃ | CH | |
| H | N(CH₃)₂ | —CH₂OCH₃ | CH₃ | OCH₃ | N | |
| H | N(CH₃)₂ | —CH₂OCH₃ | OCH₃ | OCH₃ | N | |
| H | N(CH₃)₂ | OCH₂CH=CH₂ | CH₃ | OCH₃ | CH | |
| H | N(CH₃)₂ | OCH₂CH=CH₂ | OCH₃ | OCH₃ | CH | |
| H | N(CH₃)₂ | OCH₂CH=CH₂ | CH₃ | OCH₃ | N | |
| H | N(CH₃)₂ | OCH₂CH=CH₂ | OCH₃ | OCH₃ | N | |
| H | N(CH₃)₂ | CH₃ | CH₃ | OCH₃ | CH | |
| H | N(CH₃)₂ | CH₃ | OCH₃ | OCH₃ | CH | |
| H | N(CH₃)₂ | CH₃ | CH₃ | OCH₃ | N | |
| H | N(CH₃)₂ | CH₃ | OCH₃ | OCH₃ | N | |
| H | N(CH₃)₂ | Cl | CH₃ | OCH₃ | CH | |
| H | N(CH₃)₂ | Cl | OCH₃ | OCH₃ | CH | |
| H | N(CH₃)₂ | Cl | CH₃ | OCH₃ | N | |
| H | N(CH₃)₂ | Cl | OCH₃ | OCH₃ | N | |
| H | N(CH₃)₂ | Br | CH₃ | OCH₃ | CH | |
| H | N(CH₃)₂ | Br | OCH₃ | OCH₃ | CH | |
| H | N(CH₃)₂ | Br | CH₃ | OCH₃ | N | |
| H | N(CH₃)₂ | Br | OCH₃ | OCH₃ | N | |
| H | N(CH₃)₂ | F | CH₃ | OCH₃ | CH | |
| H | N(CH₃)₂ | F | OCH₃ | OCH₃ | CH | |
| H | N(CH₃)₂ | F | CH₃ | OCH₃ | N | |
| H | N(CH₃)₂ | F | OCH₃ | OCH₃ | N | |
| H | N(CH₃)₂ | H | OCH₃ | OCH₃ | CH | |
| H | N(CH₃)₂ | H | CH₃ | OCH₃ | N | |
| H | N(CH₃)₂ | n-C₄H₉ | OCH₃ | OCH₃ | CH | |
| H | N(CH₃)₂ | CO₂CH₂CH₃ | OCH₃ | OCH₃ | CH | |
| H | N(CH₃)₂ | —CO₂—i-C₃H₇ | OCH₃ | OCH₃ | CH | |
| H | N(CH₃)₂ | —CO₂—CH₂CH=CH₂ | OCH₃ | OCH₃ | CH | |
| H | N(CH₃)₂ | —CO₂CH₂CH₂Cl | OCH₃ | OCH₃ | CH | |
| H | N(CH₃)₂ | —CO₂CH₂CH₂OCH₃ | OCH₃ | OCH₃ | CH | |
| H | N(CH₃)₂ | —OC₄H₉ | OCH₃ | OCH₃ | CH | |
| H | N(CH₃)₂ | —S—C₄H₉ | OCH₃ | OCH₃ | CH | |
| H | N(CH₃)₂ | SO₂N(C₂H₅)₂ | OCH₃ | OCH₃ | CH | |
| H | N(CH₃)₂ | SO₂CH₂CH₃ | OCH₃ | OCH₃ | CH | |
| H | N(CH₃)₂ | SO₂C₄H₉ | OCH₃ | OCH₃ | CH | |
| H | N(CH₃)₂ | OCH₂CH₂CH₂CH₂Br | OCH₃ | OCH₃ | CH | |
| H | N(CH₃)₂ | OSO₂C₄H₉ | OCH₃ | OCH₃ | CH | |
| H | N(C₂H₅)₂ | CO₂CH₃ | OCH₃ | OCH₃ | CH | |
| H | N(CH₃)C₄H₉ | CO₂CH₃ | OCH₃ | OCH₃ | CH | |
| H | N(CH₃)CH₂CF₃ | CO₂CH₃ | OCH₃ | OCH₃ | CH | |
| H | N—(CH₂CH₂Cl)₂ | CO₂CH₃ | OCH₃ | OCH₃ | CH | |
| H | N—(CH₃)CH₂CH₂Br | CO₂CH₃ | OCH₃ | OCH₃ | CH | |
| H | N(CH₃)CH₂CH=CH₂ | CO₂CH₃ | OCH₃ | OCH₃ | CH | |
| H | N(CH₃)CHCH=CHCH₃ (with CH₃ substituent) | CO₂CH₃ | OCH₃ | OCH₃ | CH | |
| H | N(OH)CH₃ | CO₂CH₃ | OCH₃ | OCH₃ | CH | |
| H | N(OCH₃)CH₃ | CO₂CH₃ | OCH₃ | OCH₃ | CH | |
| H | N(CH₃)CH₂OH | CO₂CH₃ | OCH₃ | OCH₃ | CH | |
| H | N(CH₃)CH₂OCH₃ | CO₂CH₃ | OCH₃ | OCH₃ | CH | |
| H | N(CH₃)(cyclopropyl) | CO₂CH₃ | OCH₃ | OCH₃ | CH | |
| H | N(CH₃)(cyclopentyl) | CO₂CH₃ | OCH₃ | OCH₃ | CH | |

TABLE V-continued

General Formula V

| R | R₁ | R₃ | X | Y | Z | m.p. (°C.) |
|---|---|---|---|---|---|---|
| H | N—(CH₂)₄— (cyclic) | CO₂CH₃ | OCH₃ | OCH₃ | CH | |
| H | N—(CH₂)₅— (cyclic) | CO₂CH₃ | OCH₃ | OCH₃ | CH | |
| H | N—CH₂CH₂OCH₂CH₂— (cyclic) | CO₂CH₃ | OCH₃ | OCH₃ | CH | |
| H | N(CH₃)CH₂CH₂OCH₃ | CO₂CH₃ | OCH₃ | OCH₃ | CH | |
| H | N(CH₂CH₂OCH₂CH₃)₂ | CO₂CH₃ | OCH₃ | OCH₃ | CH | |
| H | N(CH₃)OC₄H₉ | CO₂CH₃ | OCH₃ | OCH₃ | CH | |
| H | NHCN | CO₂CH₃ | OCH₃ | OCH₃ | CH | |
| H | N(CH₃)—(4,6-dimethylpyrimidin-2-yl) | CO₂CH₃ | OCH₃ | OCH₃ | CH | |
| H | P(O)(OCH₃)₂ | CO₂CH₃ | CH₃ | OCH₃ | CH | |
| H | P(O)(CH₃)OCH₃ | CO₂CH₃ | OCH₃ | OCH₃ | CH | |
| H | P(O)(CH₂CF₃)OCH₃ | CO₂CH₃ | OCH₃ | OCH₃ | CH | |
| H | P(O)(OCH₃)CH₂CH=CH₂ | CO₂CH₃ | OCH₃ | OCH₃ | CH | |
| H | P(S)(CH₃)OCH₃ | CO₂CH₃ | OCH₃ | OCH₃ | CH | |
| H | P(O)(CH₃)SCH₃ | CO₂CH₃ | OCH₃ | OCH₃ | CH | |
| H | P(O)(CH₃)NHCH₃ | CO₂CH₃ | OCH₃ | OCH₃ | CH | |
| H | P(O)—(CH₂)₃O— (cyclic) | CO₂CH₃ | OCH₃ | OCH₃ | CH | |
| H | P(O)(OCH₃)CH₂CH₂OCH₃ | CO₂CH₃ | OCH₃ | OCH₃ | CH | |
| H | P(O)(OCH₃)cyclopropyl | CO₂CH₃ | OCH₃ | OCH₃ | CH | |
| H | P⁺(C₆H₅)₃ | CO₂CH₃ | OCH₃ | OCH₃ | CH | |
| H | P⁺(n-C₄H₉)₃ | CO₂CH₃ | OCH₃ | OCH₃ | CH | |
| H | P⁺(CH₃)(C₂H₅)₂ | CO₂CH₃ | OCH₃ | OCH₃ | CH | |
| H | SCH₃ | CO₂CH₃ | OCH₃ | OCH₃ | CH | |
| H | S—n-C₄H₉ | CO₂CH₃ | OCH₃ | OCH₃ | CH | |
| H | SC₆H₅ | CO₂CH₃ | OCH₃ | OCH₃ | CH | |
| H | S—(3,4-C₆H₃Cl₂) | CO₂CH₃ | OCH₃ | OCH₃ | CH | |
| H | S—(4-C₆H₄Cl) | CO₂CH₃ | OCH₃ | OCH₃ | CH | |
| H | S—(2-C₆H₄Br) | CO₂CH₃ | OCH₃ | OCH₃ | CH | |
| H | SO₂CH₃ | CO₂CH₃ | OCH₃ | OCH₃ | CH | |
| H | SO₂—n-C₄H₉ | CO₂CH₃ | OCH₃ | OCH₃ | CH | |
| H | SO₂C₆H₅ | CO₂CH₃ | OCH₃ | OCH₃ | CH | |
| H | SO₂(3,4-C₆H₃Cl₂) | CO₂CH₃ | OCH₃ | OCH₃ | CH | |
| H | SO₂(4-C₆H₄Cl) | CO₂CH₃ | OCH₃ | OCH₃ | CH | |
| H | SO₂(2-C₆H₄Br) | CO₂CH₃ | OCH₃ | OCH₃ | CH | |
| H | CH₂NO₂ | CO₂CH₃ | OCH₃ | OCH₃ | CH | |
| H | CH(CH₃)NO₂ | CO₂CH₃ | OCH₃ | OCH₃ | CH | |
| H | C(CH₃)₂NO₂ | CO₂CH₃ | OCH₃ | OCH₃ | CH | |
| H | C(CH₃)(C₆H₅)NO₂ | CO₂CH₃ | OCH₃ | OCH₃ | CH | |
| H | CH(C₄H₉)NO₂ | CO₂CH₃ | OCH₃ | OCH₃ | CH | |
| H | CH(4-C₆H₄Cl)NO₂ | CO₂CH₃ | OCH₃ | OCH₃ | CH | |
| H | CH(CN)₂ | CO₂CH₃ | OCH₃ | OCH₃ | CH | |
| H | N(CH₃)₂ | CO₂CH₃ | OC₂H₅ | CH₃ | N | |
| H | N(CH₃)₂ | CO₂CH₃ | Cl | OCH₃ | CH | |
| H | N(CH₃)₂ | CO₂CH₃ | F | OCH₃ | CH | |
| H | N(CH₃)₂ | CO₂CH₃ | Br | OCH₃ | CH | |
| H | N(CH₃)₂ | CO₂CH₃ | OCF₂H | CH₃ | CH | |
| H | N(CH₃)₂ | CO₂CH₃ | CF₂H | CH₃ | CH | |
| H | N(CH₃)₂ | CO₂CH₃ | OCH₂CH₂F | CH₃ | CH | |
| H | N(CH₃)₂ | CO₂CH₃ | OCH₂CHF₂ | CH₃ | CH | |
| H | N(CH₃)₂ | CO₂CH₃ | OCH₂CF₃ | CH₃ | CH | |
| H | N(CH₃)₂ | CO₂CH₃ | CF₃ | OCH₃ | CH | |
| H | N(CH₃)₂ | CO₂CH₃ | OCH₃ | H | CH | |
| H | N(CH₃)₂ | CO₂CH₃ | OCH₃ | CH₂OCH₃ | CH | |
| H | N(CH₃)₂ | CO₂CH₃ | OCH₃ | NHCH₃ | N | |
| H | N(CH₃)₂ | CO₂CH₃ | OCH₃ | N(CH₃)OCH₃ | N | |
| H | N(CH₃)₂ | CO₂CH₃ | OCH₃ | N(CH₃)₂ | N | |
| H | N(CH₃)₂ | CO₂CH₃ | OCH₃ | CH₂CH₃ | CH | |

TABLE V-continued

General Formula V

| R | $R_1$ | $R_3$ | X | Y | Z | m.p. (°C.) |
|---|---|---|---|---|---|---|
| H | $N(CH_3)_2$ | $CO_2CH_3$ | $CF_3$ | $CF_3$ | CH | |
| H | $N(CH_3)_2$ | $CO_2CH_3$ | $CH_3$ | $SCH_3$ | CH | |
| H | $N(CH_3)_2$ | $CO_2CH_3$ | $CH_3$ | $OCH_2C\equiv CH$ | CH | |
| H | $N(CH_3)_2$ | $CO_2CH_3$ | $CH_3$ | $OCH_2CH=CH_2$ | CH | |
| H | $N(CH_3)_2$ | $CO_2CH_3$ | $CH_3$ | $CH_2OCH_2CH_3$ | CH | |
| H | $N(CH_3)_2$ | $CO_2CH_3$ | $OCH_3$ | $OCH_2CH_2OCH_3$ | CH | |
| H | $N(CH_3)_2$ | $CO_2CH_3$ | $OCH_3$ | $CH_2SCH_3$ | CH | |
| H | $N(CH_3)_2$ | $CO_2CH_3$ | $CH_3$ | CHO | CH | |
| H | $N(CH_3)_2$ | $CO_2CH_3$ | $CH_3$ | $COCH_3$ | CH | |
| H | $N(CH_3)_2$ | $CO_2CH_3$ | $CH_3$ | $CH(OCH_3)_2$ | CH | |
| H | $N(CH_3)_2$ | $CO_2CH_3$ | $CH_3$ | CH—$OCH_2CH_2O$— | CH | |
| H | $N(CH_3)_2$ | $CO_2CH_3$ | $CH_3$ | $OCF_2H$ | CH | |
| H | $N(CH_3)_2$ | $CO_2CH_3$ | $CH_3$ | $SCF_2H$ | CH | |
| H | $N(CH_3)_2$ | $CO_2CH_3$ | $CH_3$ | —cyclopropyl | CH | |

TABLE VI

General Formula VI

| Q | R | $R_2$ | $R_4$ | $R_5$ | $R_6$ | $R_9$ | $R_{12}$ | $R_{13}$ | $R_{14}$ | m.p. (°C.) |
|---|---|---|---|---|---|---|---|---|---|---|
| Q-1 | H | $CO_2CH_3$ | — | — | — | — | $NHC_6H_5$ | — | — | |
| Q-1 | H | $CO_2CH_3$ | — | — | — | — | $CH_3$ | — | — | |
| Q-1 | H | $CO_2CH_3$ | — | — | — | — | $OCH_3$ | — | — | |
| Q-1 | H | $CO_2CH_3$ | — | — | — | — | O—t-$C_4H_9$ | — | — | |
| Q-1 | H | $CO_2CH_3$ | — | — | — | — | $NHCH_3$ | — | — | |
| Q-2 | H | $CO_2CH_3$ | — | — | — | $CH_3$ | $CH_3$ | — | — | |
| Q-2 | H | $CO_2CH_3$ | — | — | — | $C_6H_5$ | $CH_3$ | — | — | |
| Q-2 | H | $CO_2CH_3$ | — | — | — | $CH_3$ | $OCH_3$ | — | — | |
| Q-2 | H | $CO_2CH_3$ | — | — | — | $CH_3$ | $NHCH_3$ | — | — | |
| Q-2 | H | $CO_2CH_3$ | — | — | — | $CH_3$ | $NHC_6H_5$ | — | — | |
| Q-3 | H | $CO_2CH_3$ | — | — | — | — | $CH_3$ | — | — | |
| Q-3 | H | $CO_2CH_3$ | — | — | — | — | $OCH_3$ | — | — | |
| Q-3 | H | $CO_2CH_3$ | — | — | — | — | O—t-$C_4H_9$ | — | — | |
| Q-3 | H | $CO_2CH_3$ | — | — | — | — | $NHCH_3$ | — | — | |
| Q-4 | H | $CO_2CH_3$ | — | — | — | — | $CH_3$ | — | — | |
| Q-4 | H | $CO_2CH_3$ | — | — | — | — | $OCH_3$ | — | — | |
| Q-4 | H | $CO_2CH_3$ | — | — | — | — | O—t-$C_4H_9$ | — | — | |
| Q-4 | H | $CO_2CH_3$ | — | — | — | — | $NHCH_3$ | — | — | |
| Q-5 | H | $CO_2CH_3$ | — | — | — | — | — | — | — | |
| Q-6 | H | $CO_2CH_3$ | — | — | — | — | — | — | — | |
| Q-7 | H | $CO_2CH_3$ | — | — | — | — | — | — | — | |
| Q-8 | H | $CO_2CH_3$ | — | — | — | — | — | H | H | |
| Q-8 | H | $CO_2CH_3$ | — | — | — | — | — | H | 4-$CH_3$ | |
| Q-8 | H | $CO_2CH_3$ | — | — | — | — | — | H | 4-$OCH_3$ | |
| Q-8 | H | $CO_2CH_3$ | — | — | — | — | — | H | 3-$SCH_3$ | |
| Q-8 | H | $CO_2CH_3$ | — | — | — | — | — | 3-Cl | 4-Cl | |
| Q-8 | H | $CO_2CH_3$ | — | — | — | — | — | H | 4-$CO_2CH_3$ | |
| Q-8 | H | $CO_2CH_3$ | — | — | — | — | — | 2-$OCH_3$ | 5-$OCH_3$ | |
| Q-8 | H | $CO_2CH_3$ | — | — | — | — | — | 2-F | 5-$NHCOCH_3$ | |
| Q-9 | H | $CO_2CH_3$ | $CH_3$ | $CH_3$ | — | — | — | H | H | 221–231 |
| Q-9 | H | $CO_2CH_3$ | $CH_3$ | $CH_3$ | — | — | — | 2-$NHCOCH_3$ | H | |
| Q-9 | H | $CO_2CH_3$ | $CH_3$ | $CH_3$ | — | — | — | 2-Cl | H | |
| Q-9 | H | $CO_2CH_3$ | $CH_3$ | $CH_3$ | — | — | — | 2-$OCH_3$ | H | |
| Q-9 | H | $CO_2CH_3$ | $CH_3$ | $CH_3$ | — | — | — | 2-$SCH_3$ | H | |
| Q-9 | H | $CO_2CH_3$ | $C_2H_5$ | $C_2H_5$ | — | — | — | H | H | |
| Q-9 | H | $CO_2CH_3$ | $CH_3$ | $CH_2CH=CH_2$ | — | — | — | H | H | |
| Q-9 | H | $CO_2CH_3$ | $CH_2CH_2Cl$ | $CH_2CH_2Cl$ | — | — | — | H | H | |
| Q-9 | H | $CO_2CH_3$ | $CH_2CH_2OH$ | $CH_2CH_2OH$ | — | — | — | H | H | |
| Q-9 | H | $CO_2CH_3$ | —$CH_2CH_2OCH_2CH_2$— | | — | — | — | H | H | |
| Q-10 | H | $CO_2CH_3$ | — | — | — | — | — | H | H | |
| Q-10 | H | $CO_2CH_3$ | — | — | — | — | — | 2-$NHCOCH_3$ | H | |
| Q-10 | H | $CO_2CH_3$ | — | — | — | — | — | 2-Cl | H | |
| Q-10 | H | $CO_2CH_3$ | — | — | — | — | — | 2-$OCH_3$ | H | |
| Q-10 | H | $CO_2CH_3$ | — | — | — | — | — | 2-$SCH_3$ | H | |
| Q-10 | H | $CO_2CH_3$ | — | — | — | — | — | 3-$CO_2CH_3$ | H | |
| Q-10 | H | $CO_2CH_3$ | — | — | — | — | — | 3-Cl | 5-Cl | |
| Q-11 | H | $CO_2CH_3$ | $CH_3$ | $CH_3$ | — | — | — | H | H | |
| Q-11 | H | $CO_2CH_3$ | $CH_3$ | $CH_3$ | — | — | — | 4-$NHCOCH_3$ | H | |
| Q-11 | H | $CO_2CH_3$ | $CH_3$ | $CH_3$ | — | — | — | 4-Cl | H | |
| Q-11 | H | $CO_2CH_3$ | $CH_3$ | $CH_3$ | — | — | — | 4-$OCH_3$ | H | |
| Q-11 | H | $CO_2CH_3$ | $CH_3$ | $CH_3$ | — | — | — | 4-$SCH_3$ | H | |
| Q-11 | H | $CO_2CH_3$ | $C_2H_5$ | $C_2H_5$ | — | — | — | H | H | |
| Q-11 | H | $CO_2CH_3$ | $CH_3$ | $CH_2CH=CH_2$ | — | — | — | H | H | |
| Q-11 | H | $CO_2CH_3$ | $CH_2CH_2Cl$ | $CH_2CH_2Cl$ | — | — | — | H | H | |
| Q-11 | H | $CO_2CH_3$ | $CH_2CH_2OH$ | $CH_2CH_2OH$ | — | — | — | H | H | |

TABLE VI-continued

General Formula VI

| Q | R | $R_2$ | $R_4$ | $R_5$ | $R_6$ | $R_9$ | $R_{12}$ | $R_{13}$ | $R_{14}$ | m.p. (°C.) |
|---|---|---|---|---|---|---|---|---|---|---|
| Q-11 | H | $CO_2CH_3$ | — | $-CH_2CH_2OCH_2CH_2-$ | — | — | — | H | H | |
| Q-12 | H | $CO_2CH_3$ | — | — | — | — | — | H | H | |
| Q-12 | H | $CO_2CH_3$ | — | — | — | — | — | 4-$NHCOCH_3$ | H | |
| Q-12 | H | $CO_2CH_3$ | — | — | — | — | — | 4-Cl | H | |
| Q-12 | H | $CO_2CH_3$ | — | — | — | — | — | 4-$OCH_3$ | H | |
| Q-12 | H | $CO_2CH_3$ | — | — | — | — | — | 4-$SCH_3$ | H | |
| Q-12 | H | $CO_2CH_3$ | — | — | — | — | — | 4-$CO_2CH_3$ | H | |
| Q-12 | H | $CO_2CH_3$ | — | — | — | — | — | 3-Cl | 5-Cl | |
| Q-13 | H | $CO_2CH_3$ | — | — | $CH_3$ | H | — | — | — | |
| Q-13 | H | $CO_2CH_3$ | — | — | $C_4H_9$ | $CH_3$ | — | — | — | |
| Q-13 | H | $CO_2CH_3$ | — | — | $CH_3$ | $C_6H_5$ | — | — | — | |
| Q-13 | H | $CO_2CH_3$ | — | — | $CH_3$ | 4-$C_6H_4Cl$ | — | — | — | |
| Q-13 | H | $CO_2CH_3$ | — | — | $CH_3$ | 2,4-$C_6H_3Cl_2$ | — | — | — | |
| Q-13 | H | $CO_2CH_3$ | — | — | $CH_3$ | $CH_3$ | — | — | — | |
| Q-14 | H | $CO_2CH_3$ | — | — | — | $CH_3$ | — | H | — | |
| Q-14 | H | $CO_2CH_3$ | — | — | — | $C_6H_5$ | — | H | — | |
| Q-14 | H | $CO_2CH_3$ | — | — | — | 4-$C_6H_4Cl$ | — | H | — | |
| Q-14 | H | $CO_2CH_3$ | — | — | — | $CH_3$ | — | $CH_3$ | — | |
| Q-14 | H | $CO_2CH_3$ | — | — | — | $CH_3$ | — | Cl | — | |
| Q-14 | H | $CO_2CH_3$ | — | — | — | $CH_3$ | — | $OCH_3$ | — | |

TABLE VII

General Formula VII

| R | $R_1$ | $R_3$ | X | Y | Z | m.p. (°C.) |
|---|---|---|---|---|---|---|
| $CH_3$ | $N(CH_3)_2$ | $CO_2CH_3$ | $OCH_3$ | $OCH_3$ | CH | |
| H | $N(CH_3)_2$ | $CO_2CH_3$ | $CH_3$ | $CH_3$ | CH | |
| H | $N(CH_3)_2$ | $CO_2CH_3$ | $OCH_3$ | $CH_3$ | CH | |
| H | $N(CH_3)_2$ | $CO_2CH_3$ | $OCH_3$ | $OCH_3$ | CH | |
| H | $N(CH_3)_2$ | $CO_2CH_3$ | $CH_3$ | $CH_3$ | N | |
| H | $N(CH_3)_2$ | $CO_2CH_3$ | $OCH_3$ | $CH_3$ | N | |
| H | $N(CH_3)_2$ | $CO_2CH_3$ | $OCH_3$ | $OCH_3$ | N | |
| H | $N(CH_3)_2$ | $NO_2$ | $CH_3$ | $OCH_3$ | CH | |
| H | $N(CH_3)_2$ | $NO_2$ | $OCH_3$ | $OCH_3$ | CH | |
| H | $N(CH_3)_2$ | $NO_2$ | $OCH_3$ | $CH_3$ | N | |
| H | $N(CH_3)_2$ | $NO_2$ | $OCH_3$ | $OCH_3$ | N | |
| H | $N(CH_3)_2$ | $CF_3$ | $CH_3$ | $OCH_3$ | CH | |
| H | $N(CH_3)_2$ | $CF_3$ | $OCH_3$ | $OCH_3$ | CH | |
| H | $N(CH_3)_2$ | $CF_3$ | $CH_3$ | $OCH_3$ | N | |
| H | $N(CH_3)_2$ | $CF_3$ | $OCH_3$ | $OCH_3$ | N | |
| H | $N(CH_3)_2$ | $OCH_3$ | $CH_3$ | $OCH_3$ | CH | |
| H | $N(CH_3)_2$ | $OCH_3$ | $OCH_3$ | $OCH_3$ | CH | |
| H | $N(CH_3)_2$ | $OCH_3$ | $CH_3$ | $OCH_3$ | N | |
| H | $N(CH_3)_2$ | $OCH_3$ | $OCH_3$ | $OCH_3$ | N | |
| H | $N(CH_3)_2$ | $SCH_3$ | $CH_3$ | $OCH_3$ | CH | |
| H | $N(CH_3)_2$ | $SCH_3$ | $OCH_3$ | $OCH_3$ | CH | |
| H | $N(CH_3)_2$ | $SCH_3$ | $CH_3$ | $OCH_3$ | N | |
| H | $N(CH_3)_2$ | $SCH_3$ | $OCH_3$ | $OCH_3$ | N | |
| H | $N(CH_3)_2$ | $SO_2N(CH_3)_2$ | $CH_3$ | $OCH_3$ | CH | |
| H | $N(CH_3)_2$ | $SO_2N(CH_3)_2$ | $OCH_3$ | $OCH_3$ | CH | |
| H | $N(CH_3)_2$ | $SO_2N(CH_3)_2$ | $CH_3$ | $OCH_3$ | N | |
| H | $N(CH_3)_2$ | $SO_2N(CH_3)_2$ | $OCH_3$ | $OCH_3$ | N | |
| H | $N(CH_3)_2$ | $SO_2CH_3$ | $CH_3$ | $OCH_3$ | CH | |
| H | $N(CH_3)_2$ | $SO_2CH_3$ | $OCH_3$ | $OCH_3$ | CH | |
| H | $N(CH_3)_2$ | $SO_2CH_3$ | $CH_3$ | $OCH_3$ | N | |
| H | $N(CH_3)_2$ | $SO_2CH_3$ | $OCH_3$ | $OCH_3$ | N | |
| H | $N(CH_3)_2$ | $OCH_2CH_2Cl$ | $OCH_3$ | $OCH_3$ | CH | |
| H | $N(CH_3)_2$ | $OCH_2CH_2Cl$ | $CH_3$ | $OCH_3$ | N | |
| H | $N(CH_3)_2$ | $OSO_2CH_3$ | $CH_3$ | $OCH_3$ | CH | |
| H | $N(CH_3)_2$ | $OSO_2CH_3$ | $OCH_3$ | $OCH_3$ | CH | |
| H | $N(CH_3)_2$ | $OSO_2CH_3$ | $CH_3$ | $OCH_3$ | N | |
| H | $N(CH_3)_2$ | $OSO_2CH_3$ | $OCH_3$ | $OCH_3$ | N | |
| H | $N(CH_3)_2$ | $-CH_2OCH_3$ | $CH_3$ | $OCH_3$ | CH | |
| H | $N(CH_3)_2$ | $-CH_2OCH_3$ | $OCH_3$ | $OCH_3$ | CH | |
| H | $N(CH_3)_2$ | $-CH_2OCH_3$ | $CH_3$ | $OCH_3$ | N | |
| H | $N(CH_3)_2$ | $-CH_2OCH_3$ | $OCH_3$ | $OCH_3$ | N | |
| H | $N(CH_3)_2$ | $OCH_2CH=CH_2$ | $CH_3$ | $OCH_3$ | CH | |
| H | $N(CH_3)_2$ | $OCH_2CH=CH_2$ | $OCH_3$ | $OCH_3$ | CH | |
| H | $N(CH_3)_2$ | $OCH_2CH=CH_2$ | $CH_3$ | $OCH_3$ | N | |
| H | $N(CH_3)_2$ | $OCH_2CH=CH_2$ | $OCH_3$ | $OCH_3$ | N | |
| H | $N(CH_3)_2$ | $CH_3$ | $CH_3$ | $OCH_3$ | CH | |
| H | $N(CH_3)_2$ | $CH_3$ | $OCH_3$ | $OCH_3$ | CH | |
| H | $N(CH_3)_2$ | $CH_3$ | $CH_3$ | $OCH_3$ | N | |
| H | $N(CH_3)_2$ | $CH_3$ | $OCH_3$ | $OCH_3$ | N | |
| H | $N(CH_3)_2$ | Cl | $CH_3$ | $OCH_3$ | CH | |
| H | $N(CH_3)_2$ | Cl | $OCH_3$ | $OCH_3$ | CH | |
| H | $N(CH_3)_2$ | Cl | $CH_3$ | $OCH_3$ | N | |
| H | $N(CH_3)_2$ | Cl | $OCH_3$ | $OCH_3$ | N | |

TABLE VII-continued

General Formula VII

| R | R₁ | R₃ | X | Y | Z | m.p. (°C.) |
|---|----|----|---|---|---|-----------|
| H | N(CH₃)₂ | Br | CH₃ | OCH₃ | CH | |
| H | N(CH₃)₂ | Br | OCH₃ | OCH₃ | CH | |
| H | N(CH₃)₂ | Br | CH₃ | OCH₃ | N | |
| H | N(CH₃)₂ | Br | OCH₃ | OCH₃ | N | |
| H | N(CH₃)₂ | F | CH₃ | OCH₃ | CH | |
| H | N(CH₃)₂ | F | OCH₃ | OCH₃ | CH | |
| H | N(CH₃)₂ | F | CH₃ | OCH₃ | N | |
| H | N(CH₃)₂ | F | OCH₃ | OCH₃ | N | |
| H | N(CH₃)₂ | H | OCH₃ | OCH₃ | CH | |
| H | N(CH₃)₂ | H | CH₃ | OCH₃ | N | |
| H | N(CH₃)₂ | n-C₄H₉ | OCH₃ | OCH₃ | CH | |
| H | N(CH₃)₂ | CO₂CH₂CH₃ | OCH₃ | OCH₃ | CH | |
| H | N(CH₃)₂ | —CO₂—i-C₃H₇ | OCH₃ | OCH₃ | CH | |
| H | N(CH₃)₂ | —CO₂—CH₂CH=CH₂ | OCH₃ | OCH₃ | CH | |
| H | N(CH₃)₂ | —CO₂CH₂CH₂Cl | OCH₃ | OCH₃ | CH | |
| H | N(CH₃)₂ | —CO₂CH₂CH₂OCH₃ | OCH₃ | OCH₃ | CH | |
| H | N(CH₃)₂ | —OC₄H₉ | OCH₃ | OCH₃ | CH | |
| H | N(CH₃)₂ | —S—C₄H₉ | OCH₃ | OCH₃ | CH | |
| H | N(CH₃)₂ | SO₂N(C₂H₅)₂ | OCH₃ | OCH₃ | CH | |
| H | N(CH₃)₂ | SO₂CH₂CH₃ | OCH₃ | OCH₃ | CH | |
| H | N(CH₃)₂ | SO₂C₄H₉ | OCH₃ | OCH₃ | CH | |
| H | N(CH₃)₂ | OCH₂CH₂CH₂CH₂Br | OCH₃ | OCH₃ | CH | |
| H | N(CH₃)₂ | OSO₂C₄H₉ | OCH₃ | OCH₃ | CH | |
| H | N(C₂H₅)₂ | CO₂CH₃ | OCH₃ | OCH₃ | CH | |
| H | N(CH₃)C₄H₉ | CO₂CH₃ | OCH₃ | OCH₃ | CH | |
| H | N(CH₃)CH₂CF₃ | CO₂CH₃ | OCH₃ | OCH₃ | CH | |
| H | N—(CH₂CH₂Cl)₂ | CO₂CH₃ | OCH₃ | OCH₃ | CH | |
| H | N—(CH₃)CH₂CH₂Br | CO₂CH₃ | OCH₃ | OCH₃ | CH | |
| H | N(CH₃)CH₂CH=CH₂ | CO₂CH₃ | OCH₃ | OCH₃ | CH | |
| H | N(CH₃)CHCH=CHCH₃ (CH₃) | CO₂CH₃ | OCH₃ | OCH₃ | CH | |
| H | N(OH)CH₃ | CO₂CH₃ | OCH₃ | OCH₃ | CH | |
| H | N(OCH₃)CH₃ | CO₂CH₃ | OCH₃ | OCH₃ | CH | |
| H | N(CH₃)CH₂OH | CO₂CH₃ | OCH₃ | OCH₃ | CH | |
| H | N(CH₃)CH₂OCH₃ | CO₂CH₃ | OCH₃ | OCH₃ | CH | |
| H | N(CH₃)(cyclopropyl) | CO₂CH₃ | OCH₃ | OCH₃ | CH | |
| H | N(CH₃)(cyclopentyl) | CO₂CH₃ | OCH₃ | OCH₃ | CH | |
| H | N—(CH₂)₄— (ring) | CO₂CH₃ | OCH₃ | OCH₃ | CH | |
| H | N—(CH₂)₅— (ring) | CO₂CH₃ | OCH₃ | OCH₃ | CH | |
| H | N—CH₂CH₂OCH₂CH₂— (ring) | CO₂CH₃ | OCH₃ | OCH₃ | CH | |
| H | N(CH₃)CH₂CH₂OCH₃ | CO₂CH₃ | OCH₃ | OCH₃ | CH | |
| H | N(CH₂CH₂OCH₂CH₃)₂ | CO₂CH₃ | OCH₃ | OCH₃ | CH | |
| H | N(CH₃)OC₄H₉ | CO₂CH₃ | OCH₃ | OCH₃ | CH | |
| H | NHCN | CO₂CH₃ | OCH₃ | OCH₃ | CH | |
| H | N(CH₃)—(4,6-dimethylpyrimidin-2-yl) | CO₂CH₃ | OCH₃ | OCH₃ | CH | |
| H | P(O)(OCH₃)₂ | CO₂CH₃ | CH₃ | OCH₃ | CH | |
| H | P(O)(CH₃)OCH₃ | CO₂CH₃ | OCH₃ | OCH₃ | CH | |
| H | P(O)(CH₂CF₃)OCH₃ | CO₂CH₃ | OCH₃ | OCH₃ | CH | |
| H | P(O)(OCH₃)CH₂CH=CH₂ | CO₂CH₃ | OCH₃ | OCH₃ | CH | |
| H | P(S)(CH₃)OCH₃ | CO₂CH₃ | OCH₃ | OCH₃ | CH | |
| H | P(O)(CH₃)SCH₃ | CO₂CH₃ | OCH₃ | OCH₃ | CH | |
| H | P(O)(CH₃)NHCH₃ | CO₂CH₃ | OCH₃ | OCH₃ | CH | |
| H | P(O)—(CH₂)₃O— (ring) | CO₂CH₃ | OCH₃ | OCH₃ | CH | |

TABLE VII-continued

General Formula VII

| R | R₁ | R₃ | X | Y | Z | m.p. (°C.) |
|---|---|---|---|---|---|---|
| H | P(O)(OCH₃)CH₂CH₂OCH₃ | CO₂CH₃ | OCH₃ | OCH₃ | CH | |
| H | P(O)(OCH₃)cyclopropyl | CO₂CH₃ | OCH₃ | OCH₃ | CH | |
| H | P⁺(C₆H₅)₃ | CO₂CH₃ | OCH₃ | OCH₃ | CH | |
| H | P⁺(n-C₄H₉)₃ | CO₂CH₃ | OCH₃ | OCH₃ | CH | |
| H | P⁺(CH₃)(C₂H₅)₂ | CO₂CH₃ | OCH₃ | OCH₃ | CH | |
| H | SCH₃ | CO₂CH₃ | OCH₃ | OCH₃ | CH | |
| H | S—n-C₄H₉ | CO₂CH₃ | OCH₃ | OCH₃ | CH | |
| H | SC₆H₅ | CO₂CH₃ | OCH₃ | OCH₃ | CH | |
| H | S—(3,4-C₆H₃Cl₂) | CO₂CH₃ | OCH₃ | OCH₃ | CH | |
| H | S—(4-C₆H₄Cl) | CO₂CH₃ | OCH₃ | OCH₃ | CH | |
| H | S—(2-C₆H₄Br) | CO₂CH₃ | OCH₃ | OCH₃ | CH | |
| H | SO₂CH₃ | CO₂CH₃ | OCH₃ | OCH₃ | CH | |
| H | SO₂—n-C₄H₉ | CO₂CH₃ | OCH₃ | OCH₃ | CH | |
| H | SO₂C₆H₅ | CO₂CH₃ | OCH₃ | OCH₃ | CH | |
| H | SO₂(3,4-C₆H₃Cl₂) | CO₂CH₃ | OCH₃ | OCH₃ | CH | |
| H | SO₂(4-C₆H₄Cl) | CO₂CH₃ | OCH₃ | OCH₃ | CH | |
| H | SO₂(2-C₆H₄Br) | CO₂CH₃ | OCH₃ | OCH₃ | CH | |
| H | CH₂NO₂ | CO₂CH₃ | OCH₃ | OCH₃ | CH | |
| H | CH(CH₃)NO₂ | CO₂CH₃ | OCH₃ | OCH₃ | CH | |
| H | C(CH₃)₂NO₂ | CO₂CH₃ | OCH₃ | OCH₃ | CH | |
| H | C(CH₃)(C₆H₅)NO₂ | CO₂CH₃ | OCH₃ | OCH₃ | CH | |
| H | CH(C₄H₉)NO₂ | CO₂CH₃ | OCH₃ | OCH₃ | CH | |
| H | CH(4-C₆H₄Cl)NO₂ | CO₂CH₃ | OCH₃ | OCH₃ | CH | |
| H | CH(CN)₂ | CO₂CH₃ | OCH₃ | OCH₃ | CH | |
| H | N(CH₃)₂ | CO₂CH₃ | OC₂H₅ | CH₃ | N | |
| H | N(CH₃)₂ | CO₂CH₃ | Cl | OCH₃ | CH | |
| H | N(CH₃)₂ | CO₂CH₃ | F | OCH₃ | CH | |
| H | N(CH₃)₂ | CO₂CH₃ | Br | OCH₃ | CH | |
| H | N(CH₃)₂ | CO₂CH₃ | OCF₂H | CH₃ | CH | |
| H | N(CH₃)₂ | CO₂CH₃ | CF₂H | CH₃ | CH | |
| H | N(CH₃)₂ | CO₂CH₃ | OCH₂CH₂F | CH₃ | CH | |
| H | N(CH₃)₂ | CO₂CH₃ | OCH₂CHF₂ | CH₃ | CH | |
| H | N(CH₃)₂ | CO₂CH₃ | OCH₂CF₃ | CH₃ | CH | |
| H | N(CH₃)₂ | CO₂CH₃ | CF₃ | OCH₃ | CH | |
| H | N(CH₃)₂ | CO₂CH₃ | OCH₃ | H | CH | |
| H | N(CH₃)₂ | CO₂CH₃ | OCH₃ | CH₂OCH₃ | CH | |
| H | N(CH₃)₂ | CO₂CH₃ | OCH₃ | NHCH₃ | N | |
| H | N(CH₃)₂ | CO₂CH₃ | OCH₃ | N(CH₃)OCH₃ | N | |
| H | N(CH₃)₂ | CO₂CH₃ | OCH₃ | N(CH₃)₂ | N | |
| H | N(CH₃)₂ | CO₂CH₃ | OCH₃ | CH₂CH₃ | CH | |
| H | N(CH₃)₂ | CO₂CH₃ | CF₃ | CF₃ | CH | |
| H | N(CH₃)₂ | CO₂CH₃ | CH₃ | SCH₃ | CH | |
| H | N(CH₃)₂ | CO₂CH₃ | CH₃ | OCH=CH₂ | CH | |
| H | N(CH₃)₂ | CO₂CH₃ | CH₃ | OCH₂CH=CH₂ | CH | |
| H | N(CH₃)₂ | CO₂CH₃ | CH₃ | CH₂OCH₂CH₃ | CH | |
| H | N(CH₃)₂ | CO₂CH₃ | OCH₃ | OCH₂CH₂OCH₃ | CH | |
| H | N(CH₃)₂ | CO₂CH₃ | OCH₃ | CH₂SCH₃ | CH | |
| H | N(CH₃)₂ | CO₂CH₃ | CH₃ | CHO | CH | |
| H | N(CH₃)₂ | CO₂CH₃ | CH₃ | COCH₃ | CH | |
| H | N(CH₃)₂ | CO₂CH₃ | CH₃ | CH(OCH₃)₂ | CH | |
| H | N(CH₃)₂ | CO₂CH₃ | CH₃ | CH—OCH₂CH₂O— | CH | |
| H | N(CH₃)₂ | CO₂CH₃ | CH₃ | OCF₂H | CH | |
| H | N(CH₃)₂ | CO₂CH₃ | CH₃ | SCF₂H | CH | |
| H | N(CH₃)₂ | CO₂CH₃ | CH₃ | —cyclopropyl | CH | |

TABLE VIII

General Formula VIII

| Q | R | R₂ | R₄ | R₅ | R₆ | R₉ | R₁₂ | R₁₃ | R₁₄ | m.p. (°C.) |
|---|---|---|---|---|---|---|---|---|---|---|
| Q-1 | H | CO₂CH₃ | — | — | — | — | NHC₆H₅ | — | — | |
| Q-1 | H | CO₂CH₃ | — | — | — | — | CH₃ | — | — | |
| Q-1 | H | CO₂CH₃ | — | — | — | — | OCH₃ | — | — | |
| Q-1 | H | CO₂CH₃ | — | — | — | — | O—t-C₄H₉ | — | — | |
| Q-1 | H | CO₂CH₃ | — | — | — | — | NHCH₃ | — | — | |
| Q-2 | H | CO₂CH₃ | — | — | — | CH₃ | CH₃ | — | — | |
| Q-2 | H | CO₂CH₃ | — | — | — | C₆H₅ | CH₃ | — | — | |
| Q-2 | H | CO₂CH₃ | — | — | — | CH₃ | OCH₃ | — | — | |
| Q-2 | H | CO₂CH₃ | — | — | — | CH₃ | NHCH₃ | — | — | |
| Q-2 | H | CO₂CH₃ | — | — | — | CH₃ | NHC₆H₅ | — | — | |
| Q-3 | H | CO₂CH₃ | — | — | — | — | CH₃ | — | — | |
| Q-3 | H | CO₂CH₃ | — | — | — | — | OCH₃ | — | — | |
| Q-3 | H | CO₂CH₃ | — | — | — | — | O—t-C₄H₉ | — | — | |
| Q-3 | H | CO₂CH₃ | — | — | — | — | NHCH₃ | — | — | |

TABLE VIII-continued

General Formula VIII

| Q | R | R$_2$ | R$_4$ | R$_5$ | R$_6$ | R$_9$ | R$_{12}$ | R$_{13}$ | R$_{14}$ | m.p. (°C.) |
|---|---|---|---|---|---|---|---|---|---|---|
| Q-4 | H | CO$_2$CH$_3$ | — | — | — | — | CH$_3$ | — | — | |
| Q-4 | H | CO$_2$CH$_3$ | — | — | — | — | OCH$_3$ | — | — | |
| Q-4 | H | CO$_2$CH$_3$ | — | — | — | — | O—t-C$_4$H$_9$ | — | — | |
| Q-4 | H | CO$_2$CH$_3$ | — | — | — | — | NHCH$_3$ | — | — | |
| Q-5 | H | CO$_2$CH$_3$ | — | — | — | — | — | — | — | |
| Q-6 | H | CO$_2$CH$_3$ | — | — | — | — | — | — | — | |
| Q-7 | H | CO$_2$CH$_3$ | — | — | — | — | — | — | — | |
| Q-8 | H | CO$_2$CH$_3$ | — | — | — | — | — | H | H | |
| Q-8 | H | CO$_2$CH$_3$ | — | — | — | — | — | H | 4-CH$_3$ | |
| Q-8 | H | CO$_2$CH$_3$ | — | — | — | — | — | H | 4-OCH$_3$ | |
| Q-8 | H | CO$_2$CH$_3$ | — | — | — | — | — | H | 4-SCH$_3$ | |
| Q-8 | H | CO$_2$CH$_3$ | — | — | — | — | — | 3-Cl | 4-Cl | |
| Q-8 | H | CO$_2$CH$_3$ | — | — | — | — | — | H | 4-CO$_2$CH$_3$ | |
| Q-8 | H | CO$_2$CH$_3$ | — | — | — | — | — | 2-OCH$_3$ | 5-OCH$_3$ | |
| Q-8 | H | CO$_2$CH$_3$ | — | — | — | — | — | 2-F | 5-NHCOCH$_3$ | |
| Q-9 | H | CO$_2$CH$_3$ | CH$_3$ | CH$_3$ | — | — | — | H | H | 221–231 |
| Q-9 | H | CO$_2$CH$_3$ | CH$_3$ | CH$_3$ | — | — | — | 2-NHCOCH$_3$ | H | |
| Q-9 | H | CO$_2$CH$_3$ | CH$_3$ | CH$_3$ | — | — | — | 2-Cl | H | |
| Q-9 | H | CO$_2$CH$_3$ | CH$_3$ | CH$_3$ | — | — | — | 2-OCH$_3$ | H | |
| Q-9 | H | CO$_2$CH$_3$ | CH$_3$ | CH$_3$ | — | — | — | 2-SCH$_3$ | H | |
| Q-9 | H | CO$_2$CH$_3$ | C$_2$H$_5$ | C$_2$H$_5$ | — | — | — | H | H | |
| Q-9 | H | CO$_2$CH$_3$ | CH$_3$ | CH$_2$CH=CH$_2$ | — | — | — | H | H | |
| Q-9 | H | CO$_2$CH$_3$ | CH$_2$CH$_2$Cl | CH$_2$CH$_2$Cl | — | — | — | H | H | |
| Q-9 | H | CO$_2$CH$_3$ | CH$_2$CH$_2$OH | CH$_2$CH$_2$OH | — | — | — | H | H | |
| Q-9 | H | CO$_2$CH$_3$ | —CH$_2$CH$_2$OCH$_2$CH$_2$— | | — | — | — | H | H | |
| Q-10 | H | CO$_2$CH$_3$ | — | — | — | — | — | H | H | |
| Q-10 | H | CO$_2$CH$_3$ | — | — | — | — | — | 2-NHCOCH$_3$ | H | |
| Q-10 | H | CO$_2$CH$_3$ | — | — | — | — | — | 2-Cl | H | |
| Q-10 | H | CO$_2$CH$_3$ | — | — | — | — | — | 2-OCH$_3$ | H | |
| Q-10 | H | CO$_2$CH$_3$ | — | — | — | — | — | 2-SCH$_3$ | H | |
| Q-10 | H | CO$_2$CH$_3$ | — | — | — | — | — | 3-CO$_2$CH$_3$ | H | |
| Q-10 | H | CO$_2$CH$_3$ | — | — | — | — | — | 3-Cl | 5-Cl | |
| Q-11 | H | CO$_2$CH$_3$ | CH$_3$ | CH$_3$ | — | — | — | H | H | |
| Q-11 | H | CO$_2$CH$_3$ | CH$_3$ | CH$_3$ | — | — | — | 4-NHCOCH$_3$ | H | |
| Q-11 | H | CO$_2$CH$_3$ | CH$_3$ | CH$_3$ | — | — | — | 4-Cl | H | |
| Q-11 | H | CO$_2$CH$_3$ | CH$_3$ | CH$_3$ | — | — | — | 4-OCH$_3$ | H | |
| Q-11 | H | CO$_2$CH$_3$ | CH$_3$ | CH$_3$ | — | — | — | 4-SCH$_3$ | H | |
| Q-11 | H | CO$_2$CH$_3$ | C$_2$H$_5$ | C$_2$H$_5$ | — | — | — | H | H | |
| Q-11 | H | CO$_2$CH$_3$ | CH$_3$ | CH$_2$CH=CH$_2$ | — | — | — | H | H | |
| Q-11 | H | CO$_2$CH$_3$ | CH$_2$CH$_2$Cl | CH$_2$CH$_2$Cl | — | — | — | H | H | |
| Q-11 | H | CO$_2$CH$_3$ | CH$_2$CH$_2$OH | CH$_2$CH$_2$OH | — | — | — | H | H | |
| Q-11 | H | CO$_2$CH$_3$ | —CH$_2$CH$_2$OCH$_2$CH$_2$— | | — | — | — | H | H | |
| Q-12 | H | CO$_2$CH$_3$ | — | — | — | — | — | H | H | |
| Q-12 | H | CO$_2$CH$_3$ | — | — | — | — | — | 4-NHCOCH$_3$ | H | |
| Q-12 | H | CO$_2$CH$_3$ | — | — | — | — | — | 4-Cl | H | |
| Q-12 | H | CO$_2$CH$_3$ | — | — | — | — | — | 4-OCH$_3$ | H | |
| Q-12 | H | CO$_2$CH$_3$ | — | — | — | — | — | 4-SCH$_3$ | H | |
| Q-12 | H | CO$_2$CH$_3$ | — | — | — | — | — | 4-CO$_2$CH$_3$ | H | |
| Q-12 | H | CO$_2$CH$_3$ | — | — | — | — | — | 3-Cl | 5-Cl | |
| Q-13 | H | CO$_2$CH$_3$ | — | — | CH$_3$ | H | — | — | — | |
| Q-13 | H | CO$_2$CH$_3$ | — | — | C$_4$H$_9$ | CH$_3$ | — | — | — | |
| Q-13 | H | CO$_2$CH$_3$ | — | — | CH$_3$ | C$_6$H$_5$ | — | — | — | |
| Q-13 | H | CO$_2$CH$_3$ | — | — | CH$_3$ | 4-C$_6$H$_4$Cl | — | — | — | |
| Q-13 | H | CO$_2$CH$_3$ | — | — | CH$_3$ | 2,4-C$_6$H$_3$Cl$_2$ | — | — | — | |
| Q-13 | H | CO$_2$CH$_3$ | — | — | CH$_3$ | CH$_3$ | — | — | — | |
| Q-14 | H | CO$_2$CH$_3$ | — | — | — | CH$_3$ | — | H | — | |
| Q-14 | H | CO$_2$CH$_3$ | — | — | — | C$_6$H$_5$ | — | H | — | |
| Q-14 | H | CO$_2$CH$_3$ | — | — | — | 4-C$_6$H$_4$Cl | — | H | — | |
| Q-14 | H | CO$_2$CH$_3$ | — | — | — | CH$_3$ | — | CH$_3$ | — | |
| Q-14 | H | CO$_2$CH$_3$ | — | — | — | CH$_3$ | — | Cl | — | |
| Q-14 | H | CO$_2$CH$_3$ | — | — | — | CH$_3$ | — | OCH$_3$ | — | |

TABLE IX

General Formula IX

| R | R$_1$ | R$_2$ | X$_1$ | Y$_1$ | m.p. (°C.) |
|---|---|---|---|---|---|
| H | N(CH$_3$)$_2$ | H | CH$_3$ | O | |
| H | N(CH$_3$)$_2$ | H | CH$_3$ | CH$_2$ | |
| H | N(CH$_3$)$_2$ | H | OCH$_3$ | O | |
| H | N(CH$_3$)$_2$ | H | OCH$_3$ | CH$_2$ | |
| H | N(CH$_3$)$_2$ | H | OC$_2$H$_5$ | O | |
| H | N(CH$_3$)$_2$ | H | OC$_2$H$_5$ | CH$_2$ | |
| H | N(CH$_3$)$_2$ | H | OCF$_2$H | O | |
| H | N(CH$_3$)$_2$ | H | OCF$_2$H | CH$_2$ | |
| CH$_3$ | N(CH$_3$)$_2$ | H | OCH$_3$ | O | |
| H | N(CH$_3$)$_2$ | 6-Cl | CH$_3$ | O | |
| H | N(CH$_3$)$_2$ | 5-OCH$_3$ | CH$_3$ | O | |
| H | N(CH$_3$)$_2$ | 5-SCH$_3$ | CH$_3$ | O | |
| H | N(CH$_3$)$_2$ | 5-N(CH$_3$)$_2$ | CH$_3$ | O | |
| H | N(CH$_3$)$_2$ | 5-NO$_2$ | CH$_3$ | O | |
| H | N(CH$_3$)$_2$ | 6-CH$_3$ | CH$_3$ | O | |
| H | N(CH$_3$)$_2$ | 6-CF$_3$ | CH$_3$ | O | |
| H | N(CH$_3$)C$_4$H$_9$ | H | CH$_3$ | O | |
| H | N(CH$_3$)CH$_2$CH=CH$_2$ | H | CH$_3$ | O | |
| H | N(OH)CH$_3$ | H | CH$_3$ | O | |
| H | N(CH$_3$)CH$_2$OH | H | CH$_3$ | O | |

TABLE IX-continued

General Formula IX

| R | R₁ | R₂ | X₁ | Y₁ | m.p. (°C.) |
|---|---|---|---|---|---|
| H | NHCN | H | CH₃ | O | |
| H | P(O)(OCH₃)₂ | H | CH₃ | O | |
| H | P(O)(CH₃)OCH₃ | H | CH₃ | O | |
| H | P(S)(CH₃)OCH₃ | H | CH₃ | O | |
| H | P⁺(C₆H₅)₃ | H | CH₃ | O | |
| H | SCH₃ | H | CH₃ | O | |
| H | SO₂CH₃ | H | CH₃ | O | |
| H | CH₂NO₂ | H | CH₃ | O | |
| H | CH(CN)₂ | H | CH₃ | O | |

TABLE X

General Formula X

| Q | R | R₂ | R₄ | R₅ | R₆ | R₉ | R₁₂ | R₁₃ | R₁₄ | m.p. (°C.) |
|---|---|---|---|---|---|---|---|---|---|---|
| Q-1 | H | H | — | — | — | — | OCH₃ | — | — | |
| Q-1 | H | H | — | — | — | — | CH₃ | — | — | |
| Q-2 | H | H | — | — | — | CH₃ | OCH₃ | — | — | |
| Q-2 | H | H | — | — | — | CH₃ | CH₃ | — | — | |
| Q-3 | H | H | — | — | — | — | OCH₃ | — | — | |
| Q-3 | H | H | — | — | — | — | CH₃ | — | — | |
| Q-4 | H | H | — | — | — | — | OCH₃ | — | — | |
| Q-4 | H | H | — | — | — | — | CH₃ | — | — | |
| Q-5 | H | H | — | — | — | — | — | — | — | |
| Q-6 | H | H | — | — | — | — | — | — | — | |
| Q-7 | H | H | — | — | — | — | — | — | — | |
| Q-8 | H | H | — | — | — | — | — | H | H | |
| Q-9 | H | H | CH₃ | CH₃ | — | — | — | H | H | |
| Q-10 | H | H | — | — | — | — | — | H | H | |
| Q-11 | H | H | CH₃ | CH₃ | — | — | — | CH₃ | H | |
| Q-12 | H | H | — | — | — | — | — | CH₃ | H | |
| Q-13 | H | H | — | — | CH₃ | CH₃ | — | — | — | |
| Q-14 | H | H | — | — | CH₃ | CH₃ | — | — | — | |

TABLE XI

General Formula XI

| R | R₁ | R₂ | X₁ | Y₁ | m.p. (°C.) |
|---|---|---|---|---|---|
| H | N(CH₃)₂ | CO₂CH₃ | CH₃ | O | |
| H | N(CH₃)₂ | NO₂ | CH₃ | O | |
| H | N(CH₃)₂ | CF₃ | CH₃ | O | |
| H | N(CH₃)₂ | OCH₃ | CH₃ | O | |
| H | N(CH₃)₂ | SCH₃ | CH₃ | O | |
| H | N(CH₃)₂ | SO₂N(CH₃)₂ | CH₃ | O | |
| H | N(CH₃)₂ | SO₂CH₃ | CH₃ | O | |
| H | N(CH₃)₂ | OSO₂CH₃ | CH₃ | O | |
| H | N(CH₃)₂ | CH₂OCH₃ | CH₃ | O | |
| H | N(CH₃)₂ | OCH₂CH=CH₂ | CH₃ | O | |
| H | N(CH₃)₂ | CH₃ | CH₃ | O | |
| H | N(CH₃)₂ | Cl | CH₃ | O | |
| H | N(CH₃)C₄H₉ | CO₂CH₃ | CH₃ | O | |
| H | N(CH₃)CH₂CH=CH₂ | CO₂CH₃ | CH₃ | O | |
| H | N(OH)CH₃ | CO₂CH₃ | CH₃ | O | |
| H | N(CH₃)CH₂OH | CO₂CH₃ | CH₃ | O | |
| H | NHCN | CO₂CH₃ | CH₃ | O | |
| H | P(O)(OCH₃)₂ | CO₂CH₃ | CH₃ | O | |
| H | P(O)(CH₃)OCH₃ | CO₂CH₃ | CH₃ | O | |
| H | P(S)(CH₃)OCH₃ | CO₂CH₃ | CH₃ | O | |
| H | P⁺(C₆H₅)₃ | CO₂CH₃ | CH₃ | O | |
| H | SCH₃ | CO₂CH₃ | CH₃ | O | |
| H | SO₂CH₃ | CO₂CH₃ | CH₃ | O | |
| H | CH₂NO₂ | CO₂CH₃ | CH₃ | O | |
| H | CH(CN)₂ | CO₂CH₃ | CH₃ | O | |

TABLE XII

General Formula XII

| Q | R | R₃ | R₄ | R₅ | R₆ | R₉ | R₁₂ | R₁₃ | R₁₄ | m.p. (°C.) |
|---|---|---|---|---|---|---|---|---|---|---|
| Q-1 | H | CO₂CH₃ | — | — | — | — | OCH₃ | — | — | |
| Q-1 | H | CO₂CH₃ | — | — | — | — | CH₃ | — | — | |
| Q-2 | H | CO₂CH₃ | — | — | — | CH₃ | OCH₃ | — | — | |
| Q-2 | H | CO₂CH₃ | — | — | — | CH₃ | CH₃ | — | — | |
| Q-3 | H | CO₂CH₃ | — | — | — | — | OCH₃ | — | — | |
| Q-3 | H | CO₂CH₃ | — | — | — | — | CH₃ | — | — | |
| Q-4 | H | CO₂CH₃ | — | — | — | — | OCH₃ | — | — | |
| Q-4 | H | CO₂CH₃ | — | — | — | — | CH₃ | — | — | |
| Q-5 | H | CO₂CH₃ | — | — | — | — | — | — | — | |
| Q-6 | H | CO₂CH₃ | — | — | — | — | — | — | — | |
| Q-7 | H | CO₂CH₃ | — | — | — | — | — | — | — | |
| Q-8 | H | CO₂CH₃ | — | — | — | — | — | H | H | |
| Q-9 | H | CO₂CH₃ | CH₃ | CH₃ | — | — | — | H | H | |
| Q-10 | H | CO₂CH₃ | — | — | — | — | — | H | H | |
| Q-11 | H | CO₂CH₃ | CH₃ | CH₃ | — | — | — | CH₃ | H | |
| Q-12 | H | CO₂CH₃ | — | — | — | — | — | CH₃ | H | |
| Q-13 | H | CO₂CH₃ | — | — | CH₃ | CH₃ | — | — | — | |
| Q-14 | H | CO₂CH₃ | — | — | CH₃ | CH₃ | — | — | — | |

TABLE XIII

General Formula XIII

| R | R₁ | R₂ | X₁ | Y₁ | m.p. (°C.) |
|---|---|---|---|---|---|
| H | N(CH₃)₂ | CO₂CH₃ | CH₃ | O | |
| H | N(CH₃)₂ | NO₂ | CH₃ | O | |
| H | N(CH₃)₂ | CF₃ | CH₃ | O | |
| H | N(CH₃)₂ | OCH₃ | CH₃ | O | |
| H | N(CH₃)₂ | SCH₃ | CH₃ | O | |
| H | N(CH₃)₂ | SO₂N(CH₃)₂ | CH₃ | O | |
| H | N(CH₃)₂ | SO₂CH₃ | CH₃ | O | |
| H | N(CH₃)₂ | OSO₂CH₃ | CH₃ | O | |
| H | N(CH₃)₂ | CH₂OCH₃ | CH₃ | O | |
| H | N(CH₃)₂ | OCH₂CH=CH₂ | CH₃ | O | |
| H | N(CH₃)₂ | CH₃ | CH₃ | O | |
| H | N(CH₃)₂ | Cl | CH₃ | O | |
| H | N(CH₃)C₄H₉ | CO₂CH₃ | CH₃ | O | |
| H | N(CH₃)CH₂CH=CH₂ | CO₂CH₃ | CH₃ | O | |
| H | N(OH)CH₃ | CO₂CH₃ | CH₃ | O | |
| H | N(CH₃)CH₂OH | CO₂CH₃ | CH₃ | O | |
| H | NHCN | CO₂CH₃ | CH₃ | O | |
| H | P(O)(OCH₃)₂ | CO₂CH₃ | CH₃ | O | |
| H | P(O)(CH₃)OCH₃ | CO₂CH₃ | CH₃ | O | |
| H | P(S)(CH₃)OCH₃ | CO₂CH₃ | CH₃ | O | |
| H | P⁺(C₆H₅)₃ | CO₂CH₃ | CH₃ | O | |
| H | SCH₃ | CO₂CH₃ | CH₃ | O | |
| H | SO₂CH₃ | CO₂CH₃ | CH₃ | O | |
| H | CH₂NO₂ | CO₂CH₃ | CH₃ | O | |
| H | CH(CN)₂ | CO₂CH₃ | CH₃ | O | |

TABLE XIV

General Formula XIV

| Q | R | R₃ | R₄ | R₅ | R₆ | R₉ | R₁₂ | R₁₃ | R₁₄ | m.p. (°C.) |
|---|---|---|---|---|---|---|---|---|---|---|
| Q-1 | H | CO₂CH₃ | — | — | — | — | OCH₃ | — | — | |
| Q-1 | H | CO₂CH₃ | — | — | — | — | CH₃ | — | — | |
| Q-2 | H | CO₂CH₃ | — | — | — | CH₃ | OCH₃ | — | — | |
| Q-2 | H | CO₂CH₃ | — | — | — | CH₃ | CH₃ | — | — | |
| Q-3 | H | CO₂CH₃ | — | — | — | — | OCH₃ | — | — | |
| Q-3 | H | CO₂CH₃ | — | — | — | — | CH₃ | — | — | |
| Q-4 | H | CO₂CH₃ | — | — | — | — | OCH₃ | — | — | |
| Q-4 | H | CO₂CH₃ | — | — | — | — | CH₃ | — | — | |
| Q-5 | H | CO₂CH₃ | — | — | — | — | — | — | — | |
| Q-6 | H | CO₂CH₃ | — | — | — | — | — | — | — | |
| Q-7 | H | CO₂CH₃ | — | — | — | — | — | — | — | |
| Q-8 | H | CO₂CH₃ | — | — | — | — | — | H | H | |
| Q-9 | H | CO₂CH₃ | CH₃ | CH₃ | — | — | — | H | H | |
| Q-10 | H | CO₂CH₃ | — | — | — | — | — | H | H | |
| Q-11 | H | CO₂CH₃ | CH₃ | CH₃ | — | — | — | CH₃ | H | |
| Q-12 | H | CO₂CH₃ | — | — | — | — | — | CH₃ | H | |
| Q-13 | H | CO₂CH₃ | — | — | CH₃ | CH₃ | — | — | — | |
| Q-14 | H | CO₂CH₃ | — | — | CH₃ | CH₃ | — | — | — | |

TABLE XV

General Formula XV

| R | R₁ | R₂ | X₁ | Y₁ | m.p. (°C.) |
|---|---|---|---|---|---|
| H | N(CH₃)₂ | CO₂CH₃ | CH₃ | O | |
| H | N(CH₃)₂ | NO₂ | CH₃ | O | |
| H | N(CH₃)₂ | CF₃ | CH₃ | O | |
| H | N(CH₃)₂ | OCH₃ | CH₃ | O | |
| H | N(CH₃)₂ | SCH₃ | CH₃ | O | |
| H | N(CH₃)₂ | SO₂N(CH₃)₂ | CH₃ | O | |
| H | N(CH₃)₂ | SO₂CH₃ | CH₃ | O | |
| H | N(CH₃)₂ | OSO₂CH₃ | CH₃ | O | |
| H | N(CH₃)₂ | CH₂OCH₃ | CH₃ | O | |
| H | N(CH₃)₂ | OCH₂CH=CH₂ | CH₃ | O | |
| H | N(CH₃)₂ | CH₃ | CH₃ | O | |
| H | N(CH₃)₂ | Cl | CH₃ | O | |
| H | N(CH₃)C₄H₉ | CO₂CH₃ | CH₃ | O | |
| H | N(CH₃)CH₂CH=CH₂ | CO₂CH₃ | CH₃ | O | |
| H | N(OH)CH₃ | CO₂CH₃ | CH₃ | O | |
| H | N(CH₃)CH₂OH | CO₂CH₃ | CH₃ | O | |
| H | NHCN | CO₂CH₃ | CH₃ | O | |
| H | P(O)(OCH₃)₂ | CO₂CH₃ | CH₃ | O | |
| H | P(O)(CH₃)OCH₃ | CO₂CH₃ | CH₃ | O | |
| H | P(S)(CH₃)OCH₃ | CO₂CH₃ | CH₃ | O | |
| H | P⁺(C₆H₅)₃ | CO₂CH₃ | CH₃ | O | |
| H | SCH₃ | CO₂CH₃ | CH₃ | O | |
| H | SO₂CH₃ | CO₂CH₃ | CH₃ | O | |
| H | CH₂NO₂ | CO₂CH₃ | CH₃ | O | |
| H | CH(CN)₂ | CO₂CH₃ | CH₃ | O | |

TABLE XVI

General Formula XVI

| Q | R | R₃ | R₄ | R₅ | R₆ | R₉ | R₁₂ | R₁₃ | R₁₄ | m.p. (°C.) |
|---|---|---|---|---|---|---|---|---|---|---|
| Q-1 | H | CO₂CH₃ | — | — | — | — | OCH₃ | — | — | |
| Q-1 | H | CO₂CH₃ | — | — | — | — | CH₃ | — | — | |
| Q-2 | H | CO₂CH₃ | — | — | — | CH₃ | OCH₃ | — | — | |
| Q-2 | H | CO₂CH₃ | — | — | — | CH₃ | CH₃ | — | — | |
| Q-3 | H | CO₂CH₃ | — | — | — | — | OCH₃ | — | — | |
| Q-3 | H | CO₂CH₃ | — | — | — | — | CH₃ | — | — | |
| Q-4 | H | CO₂CH₃ | — | — | — | — | OCH₃ | — | — | |
| Q-4 | H | CO₂CH₃ | — | — | — | — | CH₃ | — | — | |
| Q-5 | H | CO₂CH₃ | — | — | — | — | — | — | — | |
| Q-6 | H | CO₂CH₃ | — | — | — | — | — | — | — | |
| Q-7 | H | CO₂CH₃ | — | — | — | — | — | — | — | |
| Q-8 | H | CO₂CH₃ | — | — | — | — | — | H | H | |
| Q-9 | H | CO₂CH₃ | CH₃ | CH₃ | — | — | — | H | H | |
| Q-10 | H | CO₂CH₃ | — | — | — | — | — | H | H | |
| Q-11 | H | CO₂CH₃ | CH₃ | CH₃ | — | — | — | CH₃ | H | |
| Q-12 | H | CO₂CH₃ | — | — | — | — | — | CH₃ | H | |
| Q-13 | H | CO₂CH₃ | — | — | CH₃ | CH₃ | — | — | — | |
| Q-14 | H | CO₂CH₃ | — | — | CH₃ | CH₃ | — | — | — | |

TABLE XVII

General Formula XVII

| R | R₁ | R₂ | X₁ | Y₂ | m.p. (°C.) |
|---|---|---|---|---|---|
| H | N(CH₃)₂ | H | CH₃ | H | |
| H | N(CH₃)₂ | H | CH₃ | CH₃ | |
| H | N(CH₃)₂ | H | OCH₃ | H | |
| H | N(CH₃)₂ | H | OCH₃ | CH₃ | |
| H | N(CH₃)₂ | H | OC₂H₅ | H | |
| H | N(CH₃)₂ | H | OC₂H₅ | CH₃ | |
| H | N(CH₃)₂ | H | OCF₂H | H | |
| H | N(CH₃)₂ | H | OCF₂H | CH₃ | |
| CH₃ | N(CH₃)₂ | H | CH₃ | CH₃ | |
| H | N(CH₃)₂ | 6-Cl | CH₃ | CH₃ | |
| H | N(CH₃)₂ | 5-OCH₃ | CH₃ | CH₃ | |
| H | N(CH₃)₂ | 5-SCH₃ | CH₃ | CH₃ | |
| H | N(CH₃)₂ | 5-N(CH₃)₂ | CH₃ | CH₃ | |
| H | N(CH₃)₂ | 5-NO₂ | CH₃ | CH₃ | |
| H | N(CH₃)₂ | 6-CH₃ | CH₃ | CH₃ | |
| H | N(CH₃)₂ | 6-CF₃ | CH₃ | CH₃ | |
| H | N(CH₃)C₄H₉ | H | CH₃ | CH₃ | |
| H | N(CH₃)CH₂CH=CH₂ | H | CH₃ | CH₃ | |
| H | N(OH)CH₃ | H | CH₃ | CH₃ | |
| H | N(CH₃)CH₂OH | H | CH₃ | CH₃ | |
| H | NHCN | H | CH₃ | CH₃ | |
| H | P(O)(OCH₃)₂ | H | CH₃ | CH₃ | |
| H | P(O)(CH₃)OCH₃ | H | CH₃ | CH₃ | |
| H | P(S)(CH₃)OCH₃ | H | CH₃ | CH₃ | |
| H | P⁺(C₆H₅)₃ | H | CH₃ | CH₃ | |
| H | SCH₃ | H | CH₃ | CH₃ | |
| H | SO₂CH₃ | H | CH₃ | CH₃ | |
| H | CH₂NO₂ | H | CH₃ | CH₃ | |
| H | CH(CN)₂ | H | CH₃ | CH₃ | |

TABLE XVIII

General Formula XVIII

| Q | R | R₂ | R₄ | R₅ | R₆ | R₉ | R₁₂ | R₁₃ | R₁₄ | m.p. (°C.) |
|---|---|---|---|---|---|---|---|---|---|---|
| Q-1 | H | H | — | — | — | — | OCH₃ | — | — | |
| Q-1 | H | H | — | — | — | — | CH₃ | — | — | |
| Q-2 | H | H | — | — | — | CH₃ | OCH₃ | — | — | |
| Q-2 | H | H | — | — | — | CH₃ | CH₃ | — | — | |
| Q-3 | H | H | — | — | — | — | OCH₃ | — | — | |
| Q-3 | H | H | — | — | — | — | CH₃ | — | — | |
| Q-4 | H | H | — | — | — | — | OCH₃ | — | — | |
| Q-4 | H | H | — | — | — | — | CH₃ | — | — | |
| Q-5 | H | H | — | — | — | — | — | — | — | |
| Q-6 | H | H | — | — | — | — | — | — | — | |
| Q-7 | H | H | — | — | — | — | — | — | — | |
| Q-8 | H | H | — | — | — | — | — | H | H | |
| Q-9 | H | H | CH₃ | CH₃ | — | — | — | H | H | |
| Q-10 | H | H | — | — | — | — | — | H | H | |
| Q-11 | H | H | CH₃ | CH₃ | — | — | — | CH₃ | H | |
| Q-12 | H | H | — | — | — | — | — | CH₃ | H | |
| Q-13 | H | H | — | — | CH₃ | CH₃ | — | — | — | |
| Q-14 | H | H | — | — | CH₃ | CH₃ | — | — | — | |

TABLE XIX

General Formula XIX

| R | R₁ | R₂ | X₁ | Y₂ | m.p. (°C.) |
|---|---|---|---|---|---|
| H | N(CH₃)₂ | CO₂CH₃ | CH₃ | CH₃ | |
| H | N(CH₃)₂ | NO₂ | CH₃ | CH₃ | |
| H | N(CH₃)₂ | CF₃ | CH₃ | CH₃ | |
| H | N(CH₃)₂ | OCH₃ | CH₃ | CH₃ | |
| H | N(CH₃)₂ | SCH₃ | CH₃ | CH₃ | |
| H | N(CH₃)₂ | SO₂N(CH₃)₂ | CH₃ | CH₃ | |
| H | N(CH₃)₂ | SO₂CH₃ | CH₃ | CH₃ | |
| H | N(CH₃)₂ | OSO₂CH₃ | CH₃ | CH₃ | |
| H | N(CH₃)₂ | CH₂OCH₃ | CH₃ | CH₃ | |
| H | N(CH₃)₂ | OCH₂CH=CH₂ | CH₃ | CH₃ | |
| H | N(CH₃)₂ | CH₃ | CH₃ | CH₃ | |
| H | N(CH₃)₂ | Cl | CH₃ | CH₃ | |
| H | N(CH₃)C₄H₉ | CO₂CH₃ | CH₃ | CH₃ | |
| H | N(CH₃)CH₂CH=CH₂ | CO₂CH₃ | CH₃ | CH₃ | |
| H | N(OH)CH₃ | CO₂CH₃ | CH₃ | CH₃ | |
| H | N(CH₃)CH₂OH | CO₂CH₃ | CH₃ | CH₃ | |
| H | NHCN | CO₂CH₃ | CH₃ | CH₃ | |
| H | P(O)(OCH₃)₂ | CO₂CH₃ | CH₃ | CH₃ | |
| H | P(O)(CH₃)OCH₃ | CO₂CH₃ | CH₃ | CH₃ | |
| H | P(S)(CH₃)OCH₃ | CO₂CH₃ | CH₃ | CH₃ | |
| H | P⁺(C₆H₅)₃ | CO₂CH₃ | CH₃ | CH₃ | |
| H | SCH₃ | CO₂CH₃ | CH₃ | CH₃ | |
| H | SO₂CH₃ | CO₂CH₃ | CH₃ | CH₃ | |
| H | CH₂NO₂ | CO₂CH₃ | CH₃ | CH₃ | |
| H | CH(CN)₂ | CO₂CH₃ | CH₃ | CH₃ | |

TABLE XX

General Formula XX

| Q | R | R₃ | R₄ | R₅ | R₆ | R₉ | R₁₂ | R₁₃ | R₁₄ | m.p. (°C.) |
|---|---|---|---|---|---|---|---|---|---|---|
| Q-1 | H | CO₂CH₃ | — | — | — | — | OCH₃ | — | — | |
| Q-1 | H | CO₂CH₃ | — | — | — | — | CH₃ | — | — | |
| Q-2 | H | CO₂CH₃ | — | — | — | CH₃ | OCH₃ | — | — | |

TABLE XX-continued

General Formula XX

| Q | R | R$_3$ | R$_4$ | R$_5$ | R$_6$ | R$_9$ | R$_{12}$ | R$_{13}$ | R$_{14}$ | m.p. (°C.) |
|---|---|---|---|---|---|---|---|---|---|---|
| Q-2  | H | CO$_2$CH$_3$ | — | — | — | CH$_3$ | CH$_3$ | — | — | |
| Q-3  | H | CO$_2$CH$_3$ | — | — | — | — | OCH$_3$ | — | — | |
| Q-3  | H | CO$_2$CH$_3$ | — | — | — | — | CH$_3$ | — | — | |
| Q-4  | H | CO$_2$CH$_3$ | — | — | — | — | OCH$_3$ | — | — | |
| Q-4  | H | CO$_2$CH$_3$ | — | — | — | — | CH$_3$ | — | — | |
| Q-5  | H | CO$_2$CH$_3$ | — | — | — | — | — | — | — | |
| Q-6  | H | CO$_2$CH$_3$ | — | — | — | — | — | — | — | |
| Q-7  | H | CO$_2$CH$_3$ | — | — | — | — | — | — | — | |
| Q-8  | H | CO$_2$CH$_3$ | — | — | — | — | — | H | H | |
| Q-9  | H | CO$_2$CH$_3$ | CH$_3$ | CH$_3$ | — | — | — | H | H | |
| Q-10 | H | CO$_2$CH$_3$ | — | — | — | — | — | H | H | |
| Q-11 | H | CO$_2$CH$_3$ | CH$_3$ | CH$_3$ | — | — | — | CH$_3$ | H | |
| Q-12 | H | CO$_2$CH$_3$ | — | — | — | — | — | CH$_3$ | H | |
| Q-13 | H | CO$_2$CH$_3$ | — | — | CH$_3$ | CH$_3$ | — | — | — | |
| Q-14 | H | CO$_2$CH$_3$ | — | — | CH$_3$ | CH$_3$ | — | — | — | |

TABLE XXI

General Formula XXI

| R | R$_1$ | R$_2$ | X$_1$ | Y$_2$ | m.p. (°C.) |
|---|---|---|---|---|---|
| H | N(CH$_3$)$_2$ | CO$_2$CH$_3$ | CH$_3$ | CH$_3$ | |
| H | N(CH$_3$)$_2$ | NO$_2$ | CH$_3$ | CH$_3$ | |
| H | N(CH$_3$)$_2$ | CF$_3$ | CH$_3$ | CH$_3$ | |
| H | N(CH$_3$)$_2$ | OCH$_3$ | CH$_3$ | CH$_3$ | |
| H | N(CH$_3$)$_2$ | SCH$_3$ | CH$_3$ | CH$_3$ | |
| H | N(CH$_3$)$_2$ | SO$_2$N(CH$_3$)$_2$ | CH$_3$ | CH$_3$ | |
| H | N(CH$_3$)$_2$ | SO$_2$CH$_3$ | CH$_3$ | CH$_3$ | |
| H | N(CH$_3$)$_2$ | OSO$_2$CH$_3$ | CH$_3$ | CH$_3$ | |
| H | N(CH$_3$)$_2$ | CH$_2$OCH$_3$ | CH$_3$ | CH$_3$ | |
| H | N(CH$_3$)$_2$ | OCH$_2$CH=CH$_2$ | CH$_3$ | CH$_3$ | |
| H | N(CH$_3$)$_2$ | CH$_3$ | CH$_3$ | CH$_3$ | |
| H | N(CH$_3$)$_2$ | Cl | CH$_3$ | CH$_3$ | |
| H | N(CH$_3$)C$_4$H$_9$ | CO$_2$CH$_3$ | CH$_3$ | CH$_3$ | |
| H | N(CH$_3$)CH$_2$CH=CH$_2$ | CO$_2$CH$_3$ | CH$_3$ | CH$_3$ | |
| H | N(OH)CH$_3$ | CO$_2$CH$_3$ | CH$_3$ | CH$_3$ | |
| H | N(CH$_3$)CH$_2$OH | CO$_2$CH$_3$ | CH$_3$ | CH$_3$ | |
| H | NHCN | CO$_2$CH$_3$ | CH$_3$ | CH$_3$ | |
| H | P(O)(OCH$_3$)$_2$ | CO$_2$CH$_3$ | CH$_3$ | CH$_3$ | |
| H | P(O)(CH$_3$)OCH$_3$ | CO$_2$CH$_3$ | CH$_3$ | CH$_3$ | |
| H | P(S)(CH$_3$)OCH$_3$ | CO$_2$CH$_3$ | CH$_3$ | CH$_3$ | |
| H | P$^+$(C$_6$H$_5$)$_3$ | CO$_2$CH$_3$ | CH$_3$ | CH$_3$ | |
| H | SCH$_3$ | CO$_2$CH$_3$ | CH$_3$ | CH$_3$ | |
| H | SO$_2$CH$_3$ | CO$_2$CH$_3$ | CH$_3$ | CH$_3$ | |
| H | CH$_2$NO$_2$ | CO$_2$CH$_3$ | CH$_3$ | CH$_3$ | |
| H | CH(CN)$_2$ | CO$_2$CH$_3$ | CH$_3$ | CH$_3$ | |

TABLE XXII

General Formula XXII

| Q | R | R$_3$ | R$_4$ | R$_5$ | R$_6$ | R$_9$ | R$_{12}$ | R$_{13}$ | R$_{14}$ | m.p. (°C.) |
|---|---|---|---|---|---|---|---|---|---|---|
| Q-1  | H | CO$_2$CH$_3$ | — | — | — | — | OCH$_3$ | — | — | |
| Q-1  | H | CO$_2$CH$_3$ | — | — | — | — | CH$_3$ | — | — | |
| Q-2  | H | CO$_2$CH$_3$ | — | — | — | CH$_3$ | OCH$_3$ | — | — | |
| Q-2  | H | CO$_2$CH$_3$ | — | — | — | CH$_3$ | CH$_3$ | — | — | |
| Q-3  | H | CO$_2$CH$_3$ | — | — | — | — | OCH$_3$ | — | — | |
| Q-3  | H | CO$_2$CH$_3$ | — | — | — | — | CH$_3$ | — | — | |
| Q-4  | H | CO$_2$CH$_3$ | — | — | — | — | OCH$_3$ | — | — | |
| Q-4  | H | CO$_2$CH$_3$ | — | — | — | — | CH$_3$ | — | — | |
| Q-5  | H | CO$_2$CH$_3$ | — | — | — | — | — | — | — | |
| Q-6  | H | CO$_2$CH$_3$ | — | — | — | — | — | — | — | |
| Q-7  | H | CO$_2$CH$_3$ | — | — | — | — | — | — | — | |
| Q-8  | H | CO$_2$CH$_3$ | — | — | — | — | — | H | H | |
| Q-9  | H | CO$_2$CH$_3$ | CH$_3$ | CH$_3$ | — | — | — | H | H | |
| Q-10 | H | CO$_2$CH$_3$ | — | — | — | — | — | H | H | |
| Q-11 | H | CO$_2$CH$_3$ | CH$_3$ | CH$_3$ | — | — | — | CH$_3$ | H | |
| Q-12 | H | CO$_2$CH$_3$ | — | — | — | — | — | CH$_3$ | H | |
| Q-13 | H | CO$_2$CH$_3$ | — | — | CH$_3$ | CH$_3$ | — | — | — | |
| Q-14 | H | CO$_2$CH$_3$ | — | — | CH$_3$ | CH$_3$ | — | — | — | |

TABLE XXIII

General Formula XXIII

| R | R$_1$ | R$_2$ | X$_1$ | Y$_2$ | m.p. (°C.) |
|---|---|---|---|---|---|
| H | N(CH$_3$)$_2$ | CO$_2$CH$_3$ | CH$_3$ | CH$_3$ | |
| H | N(CH$_3$)$_2$ | NO$_2$ | CH$_3$ | CH$_3$ | |
| H | N(CH$_3$)$_2$ | CF$_3$ | CH$_3$ | CH$_3$ | |
| H | N(CH$_3$)$_2$ | OCH$_3$ | CH$_3$ | CH$_3$ | |
| H | N(CH$_3$)$_2$ | SCH$_3$ | CH$_3$ | CH$_3$ | |
| H | N(CH$_3$)$_2$ | SO$_2$N(CH$_3$)$_2$ | CH$_3$ | CH$_3$ | |
| H | N(CH$_3$)$_2$ | SO$_2$CH$_3$ | CH$_3$ | CH$_3$ | |
| H | N(CH$_3$)$_2$ | OSO$_2$CH$_3$ | CH$_3$ | CH$_3$ | |
| H | N(CH$_3$)$_2$ | CH$_2$OCH$_3$ | CH$_3$ | CH$_3$ | |
| H | N(CH$_3$)$_2$ | OCH$_2$CH=CH$_2$ | CH$_3$ | CH$_3$ | |
| H | N(CH$_3$)$_2$ | CH$_3$ | CH$_3$ | CH$_3$ | |
| H | N(CH$_3$)$_2$ | Cl | CH$_3$ | CH$_3$ | |
| H | N(CH$_3$)C$_4$H$_9$ | CO$_2$CH$_3$ | CH$_3$ | CH$_3$ | |
| H | N(CH$_3$)CH$_2$CH=CH$_2$ | CO$_2$CH$_3$ | CH$_3$ | CH$_3$ | |
| H | N(OH)CH$_3$ | CO$_2$CH$_3$ | CH$_3$ | CH$_3$ | |
| H | N(CH$_3$)CH$_2$OH | CO$_2$CH$_3$ | CH$_3$ | CH$_3$ | |
| H | NHCN | CO$_2$CH$_3$ | CH$_3$ | CH$_3$ | |
| H | P(O)(OCH$_3$)$_2$ | CO$_2$CH$_3$ | CH$_3$ | CH$_3$ | |
| H | P(O)(CH$_3$)OCH$_3$ | CO$_2$CH$_3$ | CH$_3$ | CH$_3$ | |
| H | P(S)(CH$_3$)OCH$_3$ | CO$_2$CH$_3$ | CH$_3$ | CH$_3$ | |
| H | P$^+$(C$_6$H$_5$)$_3$ | CO$_2$CH$_3$ | CH$_3$ | CH$_3$ | |
| H | SCH$_3$ | CO$_2$CH$_3$ | CH$_3$ | CH$_3$ | |
| H | SO$_2$CH$_3$ | CO$_2$CH$_3$ | CH$_3$ | CH$_3$ | |
| H | CH$_2$NO$_2$ | CO$_2$CH$_3$ | CH$_3$ | CH$_3$ | |
| H | CH(CN)$_2$ | CO$_2$CH$_3$ | CH$_3$ | CH$_3$ | |

TABLE XXIV

General Formula XXIV

| Q | R | R$_3$ | R$_4$ | R$_5$ | R$_6$ | R$_9$ | R$_{12}$ | R$_{13}$ | R$_{14}$ | m.p. (°C.) |
|---|---|---|---|---|---|---|---|---|---|---|
| Q-1  | H | CO$_2$CH$_3$ | — | — | — | — | OCH$_3$ | — | — | |
| Q-1  | H | CO$_2$CH$_3$ | — | — | — | — | CH$_3$ | — | — | |
| Q-2  | H | CO$_2$CH$_3$ | — | — | — | CH$_3$ | OCH$_3$ | — | — | |
| Q-2  | H | CO$_2$CH$_3$ | — | — | — | CH$_3$ | CH$_3$ | — | — | |
| Q-3  | H | CO$_2$CH$_3$ | — | — | — | — | OCH$_3$ | — | — | |
| Q-3  | H | CO$_2$CH$_3$ | — | — | — | — | CH$_3$ | — | — | |
| Q-4  | H | CO$_2$CH$_3$ | — | — | — | — | OCH$_3$ | — | — | |
| Q-4  | H | CO$_2$CH$_3$ | — | — | — | — | CH$_3$ | — | — | |
| Q-5  | H | CO$_2$CH$_3$ | — | — | — | — | — | — | — | |
| Q-6  | H | CO$_2$CH$_3$ | — | — | — | — | — | — | — | |
| Q-7  | H | CO$_2$CH$_3$ | — | — | — | — | — | — | — | |
| Q-8  | H | CO$_2$CH$_3$ | — | — | — | — | — | H | H | |
| Q-9  | H | CO$_2$CH$_3$ | CH$_3$ | CH$_3$ | — | — | — | H | H | |
| Q-10 | H | CO$_2$CH$_3$ | — | — | — | — | — | H | H | |
| Q-11 | H | CO$_2$CH$_3$ | CH$_3$ | CH$_3$ | — | — | — | CH$_3$ | H | |
| Q-12 | H | CO$_2$CH$_3$ | — | — | — | — | — | CH$_3$ | H | |
| Q-13 | H | CO$_2$CH$_3$ | — | — | CH$_3$ | CH$_3$ | — | — | — | |
| Q-14 | H | CO$_2$CH$_3$ | — | — | CH$_3$ | CH$_3$ | — | — | — | |

TABLE XXV

General Formula XXV

| R | R₁ | R₂ | X₁ | m.p. (°C.) |
|---|---|---|---|---|
| H | N(CH₃)₂ | H | CH₃ | |
| H | N(CH₃)₂ | H | OCH₃ | |
| H | N(CH₃)₂ | H | OC₂H₅ | |
| H | N(CH₃)₂ | H | OCF₂H | |
| CH₃ | N(CH₃)₂ | H | OCH₃ | |
| H | N(CH₃)₂ | 6-Cl | CH₃ | |
| H | N(CH₃)₂ | 5-OCH₃ | CH₃ | |
| H | N(CH₃)₂ | 5-SCH₃ | CH₃ | |
| H | N(CH₃)₂ | 5-N(CH₃)₂ | CH₃ | |
| H | N(CH₃)₂ | 5-NO₂ | CH₃ | |
| H | N(CH₃)₂ | 6-CH₃ | CH₃ | |
| H | N(CH₃)₂ | 6-CF₃ | CH₃ | |
| H | N(CH₃)C₄H₉ | H | CH₃ | |
| H | N(CH₃)CH₂CH=CH₂ | H | CH₃ | |
| H | N(OH)CH₃ | H | CH₃ | |
| H | N(CH₃)CH₂OH | H | CH₃ | |
| H | NHCN | H | CH₃ | |
| H | P(O)(OCH₃)₂ | H | CH₃ | |
| H | P(O)(CH₃)OCH₃ | H | CH₃ | |
| H | P(S)(CH₃)OCH₃ | H | CH₃ | |
| H | P⁺(C₆H₅)₃ | H | CH₃ | |
| H | SCH₃ | H | CH₃ | |
| H | SO₂CH₃ | H | CH₃ | |
| H | CH₂NO₂ | H | CH₃ | |
| H | CH(CN)₂ | H | CH₃ | |

TABLE XXVI

General Formula XXVI

| Q | R | R₂ | R₄ | R₅ | R₆ | R₉ | R₁₂ | R₁₃ | R₁₄ | m.p. (°C.) |
|---|---|---|---|---|---|---|---|---|---|---|
| Q-1 | H | H | — | — | — | — | OCH₃ | — | — | |
| Q-1 | H | H | — | — | — | — | CH₃ | — | — | |
| Q-2 | H | H | — | — | — | CH₃ | OCH₃ | — | — | |
| Q-2 | H | H | — | — | — | CH₃ | CH₃ | — | — | |
| Q-3 | H | H | — | — | — | — | OCH₃ | — | — | |
| Q-3 | H | H | — | — | — | — | CH₃ | — | — | |
| Q-4 | H | H | — | — | — | — | OCH₃ | — | — | |
| Q-4 | H | H | — | — | — | — | CH₃ | — | — | |
| Q-5 | H | H | — | — | — | — | — | — | — | |
| Q-6 | H | H | — | — | — | — | — | — | — | |
| Q-7 | H | H | — | — | — | — | — | — | — | |
| Q-8 | H | H | — | — | — | — | — | H | H | |
| Q-9 | H | H | CH₃ | CH₃ | — | — | — | H | H | |
| Q-10 | H | H | — | — | — | — | — | H | H | |
| Q-11 | H | H | CH₃ | CH₃ | — | — | — | CH₃ | H | |
| Q-12 | H | H | — | — | — | — | — | CH₃ | H | |
| Q-13 | H | H | — | — | CH₃ | CH₃ | — | — | — | |
| Q-14 | H | H | — | — | CH₃ | CH₃ | — | — | — | |

TABLE XXVII

General Formula XXVII

| R | R₁ | R₂ | X₁ | m.p. (°C.) |
|---|---|---|---|---|
| H | N(CH₃)₂ | CO₂CH₃ | CH₃ | |
| H | N(CH₃)₂ | NO₂ | CH₃ | |
| H | N(CH₃)₂ | CF₃ | CH₃ | |
| H | N(CH₃)₂ | OCH₃ | CH₃ | |
| H | N(CH₃)₂ | SCH₃ | CH₃ | |
| H | N(CH₃)₂ | SO₂N(CH₃)₂ | CH₃ | |
| H | N(CH₃)₂ | SO₂CH₃ | CH₃ | |
| H | N(CH₃)₂ | OSO₂CH₃ | CH₃ | |
| H | N(CH₃)₂ | CH₂OCH₃ | CH₃ | |
| H | N(CH₃)₂ | OCH₂CH=CH₂ | CH₃ | |
| H | N(CH₃)₂ | CH₃ | CH₃ | |
| H | N(CH₃)₂ | Cl | CH₃ | |
| H | N(CH₃)C₄H₉ | CO₂CH₃ | CH₃ | |
| H | N(CH₃)CH₂CH=CH₂ | CO₂CH₃ | CH₃ | |
| H | N(OH)CH₃ | CO₂CH₃ | CH₃ | |
| H | N(CH₃)CH₂OH | CO₂CH₃ | CH₃ | |
| H | NHCN | CO₂CH₃ | CH₃ | |
| H | P(O)(OCH₃)₂ | CO₂CH₃ | CH₃ | |
| H | P(O)(CH₃)OCH₃ | CO₂CH₃ | CH₃ | |
| H | P(S)(CH₃)OCH₃ | CO₂CH₃ | CH₃ | |
| H | P⁺(C₆H₅)₃ | CO₂CH₃ | CH₃ | |
| H | SCH₃ | CO₂CH₃ | CH₃ | |
| H | SO₂CH₃ | CO₂CH₃ | CH₃ | |
| H | CH₂NO₂ | CO₂CH₃ | CH₃ | |
| H | CH(CN)₂ | CO₂CH₃ | CH₃ | |

TABLE XXVIII

General Formula XXVIII

| Q | R | R₃ | R₄ | R₅ | R₆ | R₉ | R₁₂ | R₁₃ | R₁₄ | m.p. (°C.) |
|---|---|---|---|---|---|---|---|---|---|---|
| Q-1 | H | CO₂CH₃ | — | — | — | — | OCH₃ | — | — | |
| Q-1 | H | CO₂CH₃ | — | — | — | — | CH₃ | — | — | |
| Q-2 | H | CO₂CH₃ | — | — | — | CH₃ | OCH₃ | — | — | |
| Q-2 | H | CO₂CH₃ | — | — | — | CH₃ | CH₃ | — | — | |
| Q-3 | H | CO₂CH₃ | — | — | — | — | OCH₃ | — | — | |
| Q-3 | H | CO₂CH₃ | — | — | — | — | CH₃ | — | — | |
| Q-4 | H | CO₂CH₃ | — | — | — | — | OCH₃ | — | — | |
| Q-4 | H | CO₂CH₃ | — | — | — | — | CH₃ | — | — | |
| Q-5 | H | CO₂CH₃ | — | — | — | — | — | — | — | |
| Q-6 | H | CO₂CH₃ | — | — | — | — | — | — | — | |
| Q-7 | H | CO₂CH₃ | — | — | — | — | — | — | — | |
| Q-8 | H | CO₂CH₃ | — | — | — | — | — | H | H | |
| Q-9 | H | CO₂CH₃ | CH₃ | CH₃ | — | — | — | H | H | |
| Q-10 | H | CO₂CH₃ | — | — | — | — | — | H | H | |
| Q-11 | H | CO₂CH₃ | CH₃ | CH₃ | — | — | — | CH₃ | H | |
| Q-12 | H | CO₂CH₃ | — | — | — | — | — | CH₃ | H | |
| Q-13 | H | CO₂CH₃ | — | — | CH₃ | CH₃ | — | — | — | |
| Q-14 | H | CO₂CH₃ | — | — | CH₃ | CH₃ | — | — | — | |

TABLE XXIX

General Formula XXIX

| R | R₁ | R₂ | X₁ | m.p. (°C.) |
|---|---|---|---|---|
| H | N(CH₃)₂ | CO₂CH₃ | CH₃ | |
| H | N(CH₃)₂ | NO₂ | CH₃ | |
| H | N(CH₃)₂ | CF₃ | CH₃ | |
| H | N(CH₃)₂ | OCH₃ | CH₃ | |
| H | N(CH₃)₂ | SCH₃ | CH₃ | |
| H | N(CH₃)₂ | SO₂N(CH₃)₂ | CH₃ | |
| H | N(CH₃)₂ | SO₂CH₃ | CH₃ | |
| H | N(CH₃)₂ | OSO₂CH₃ | CH₃ | |
| H | N(CH₃)₂ | CH₂OCH₃ | CH₃ | |
| H | N(CH₃)₂ | OCH₂CH=CH₂ | CH₃ | |
| H | N(CH₃)₂ | CH₃ | CH₃ | |
| H | N(CH₃)₂ | Cl | CH₃ | |
| H | N(CH₃)C₄H₉ | CO₂CH₃ | CH₃ | |
| H | N(CH₃)CH₂CH=CH₂ | CO₂CH₃ | CH₃ | |
| H | N(OH)CH₃ | CO₂CH₃ | CH₃ | |
| H | N(CH₃)CH₂OH | CO₂CH₃ | CH₃ | |
| H | NHCN | CO₂CH₃ | CH₃ | |
| H | P(O)(OCH₃)₂ | CO₂CH₃ | CH₃ | |
| H | P(O)(CH₃)OCH₃ | CO₂CH₃ | CH₃ | |
| H | P(S)(CH₃)OCH₃ | CO₂CH₃ | CH₃ | |
| H | P⁺(C₆H₅)₃ | CO₂CH₃ | CH₃ | |
| H | SCH₃ | CO₂CH₃ | CH₃ | |
| H | SO₂CH₃ | CO₂CH₃ | CH₃ | |
| H | CH₂NO₂ | CO₂CH₃ | CH₃ | |
| H | CH(CN)₂ | CO₂CH₃ | CH₃ | |

TABLE XXX

General Formula XXX

| Q | R | R₃ | R₄ | R₅ | R₆ | R₉ | R₁₂ | R₁₃ | R₁₄ | m.p. (°C.) |
|---|---|---|---|---|---|---|---|---|---|---|
| Q-1 | H | CO₂CH₃ | — | — | — | — | OCH₃ | — | — | |
| Q-1 | H | CO₂CH₃ | — | — | — | — | CH₃ | — | — | |
| Q-2 | H | CO₂CH₃ | — | — | — | CH₃ | OCH₃ | — | — | |
| Q-2 | H | CO₂CH₃ | — | — | — | CH₃ | CH₃ | — | — | |
| Q-3 | H | CO₂CH₃ | — | — | — | — | OCH₃ | — | — | |
| Q-3 | H | CO₂CH₃ | — | — | — | — | CH₃ | — | — | |
| Q-4 | H | CO₂CH₃ | — | — | — | — | OCH₃ | — | — | |
| Q-4 | H | CO₂CH₃ | — | — | — | — | CH₃ | — | — | |
| Q-5 | H | CO₂CH₃ | — | — | — | — | — | — | — | |
| Q-6 | H | CO₂CH₃ | — | — | — | — | — | — | — | |

TABLE XXX-continued

General Formula XXX

| Q | R | $R_3$ | $R_4$ | $R_5$ | $R_6$ | $R_9$ | $R_{12}$ | $R_{13}$ | $R_{14}$ | m.p. (°C.) |
|---|---|---|---|---|---|---|---|---|---|---|
| Q-7 | H | $CO_2CH_3$ | — | — | — | — | — | — | — | |
| Q-8 | H | $CO_2CH_3$ | — | — | — | — | — | H | H | |
| Q-9 | H | $CO_2CH_3$ | $CH_3$ | $CH_3$ | — | — | — | H | H | |
| Q-10 | H | $CO_2CH_3$ | — | — | — | — | — | H | H | |
| Q-11 | H | $CO_2CH_3$ | $CH_3$ | $CH_3$ | — | — | — | $CH_3$ | H | |
| Q-12 | H | $CO_2CH_3$ | — | — | — | — | — | $CH_3$ | H | |
| Q-13 | H | $CO_2CH_3$ | — | — | $CH_3$ | $CH_3$ | — | — | — | |
| Q-14 | H | $CO_2CH_3$ | — | — | $CH_3$ | $CH_3$ | — | — | — | |

TABLE XXXI

General Formula XXXI

| R | $R_1$ | $R_2$ | $X_1$ | m.p. (°C.) |
|---|---|---|---|---|
| H | $N(CH_3)_2$ | $CO_2CH_3$ | $CH_3$ | |
| H | $N(CH_3)_2$ | $NO_2$ | $CH_3$ | |
| H | $N(CH_3)_2$ | $CF_3$ | $CH_3$ | |
| H | $N(CH_3)_2$ | $OCH_3$ | $CH_3$ | |
| H | $N(CH_3)_2$ | $SCH_3$ | $CH_3$ | |
| H | $N(CH_3)_2$ | $SO_2N(CH_3)_2$ | $CH_3$ | |
| H | $N(CH_3)_2$ | $SO_2CH_3$ | $CH_3$ | |
| H | $N(CH_3)_2$ | $OSO_2CH_3$ | $CH_3$ | |
| H | $N(CH_3)_2$ | $CH_2OCH_3$ | $CH_3$ | |
| H | $N(CH_3)_2$ | $OCH_2CH=CH_2$ | $CH_3$ | |
| H | $N(CH_3)_2$ | $CH_3$ | $CH_3$ | |
| H | $N(CH_3)_2$ | Cl | $CH_3$ | |
| H | $N(CH_3)C_4H_9$ | $CO_2CH_3$ | $CH_3$ | |
| H | $N(CH_3)CH_2CH=CH_2$ | $CO_2CH_3$ | $CH_3$ | |
| H | $N(OH)CH_3$ | $CO_2CH_3$ | $CH_3$ | |
| H | $N(CH_3)CH_2OH$ | $CO_2CH_3$ | $CH_3$ | |
| H | NHCN | $CO_2CH_3$ | $CH_3$ | |
| H | $P(O)(OCH_3)_2$ | $CO_2CH_3$ | $CH_3$ | |
| H | $P(O)(CH_3)OCH_3$ | $CO_2CH_3$ | $CH_3$ | |
| H | $P(S)(CH_3)OCH_3$ | $CO_2CH_3$ | $CH_3$ | |
| H | $P^+(C_6H_5)_3$ | $CO_2CH_3$ | $CH_3$ | |
| H | $SCH_3$ | $CO_2CH_3$ | $CH_3$ | |
| H | $SO_2CH_3$ | $CO_2CH_3$ | $CH_3$ | |
| H | $CH_2NO_2$ | $CO_2CH_3$ | $CH_3$ | |
| H | $CH(CN)_2$ | $CO_2CH_3$ | $CH_3$ | |

TABLE XXXII

General Formula XXXII

| Q | R | $R_3$ | $R_4$ | $R_5$ | $R_6$ | $R_9$ | $R_{12}$ | $R_{13}$ | $R_{14}$ | m.p. (°C.) |
|---|---|---|---|---|---|---|---|---|---|---|
| Q-1 | H | $CO_2CH_3$ | — | — | — | — | $OCH_3$ | — | — | |
| Q-1 | H | $CO_2CH_3$ | — | — | — | - | $CH_3$ | — | — | |
| Q-2 | H | $CO_2CH_3$ | — | — | — | $CH_3$ | $OCH_3$ | — | — | |
| Q-2 | H | $CO_2CH_3$ | — | — | — | $CH_3$ | $CH_3$ | — | — | |
| Q-3 | H | $CO_2CH_3$ | — | — | — | — | $OCH_3$ | — | — | |
| Q-3 | H | $CO_2CH_3$ | — | — | — | — | $CH_3$ | — | — | |
| Q-4 | H | $CO_2CH_3$ | — | — | — | — | $OCH_3$ | — | — | |
| Q-4 | H | $CO_2CH_3$ | — | — | — | — | $CH_3$ | — | — | |
| Q-5 | H | $CO_2CH_3$ | — | — | — | — | — | — | — | |
| Q-6 | H | $CO_2CH_3$ | — | — | — | — | — | — | — | |
| Q-7 | H | $CO_2CH_3$ | — | — | — | — | — | — | — | |
| Q-8 | H | $CO_2CH_3$ | — | — | — | — | — | H | H | |
| Q-9 | H | $CO_2CH_3$ | $CH_3$ | $CH_3$ | — | — | — | H | H | |
| Q-10 | H | $CO_2CH_3$ | — | — | — | — | — | H | H | |
| Q-11 | H | $CO_2CH_3$ | $CH_3$ | $CH_3$ | — | — | — | $CH_3$ | H | |
| Q-12 | H | $CO_2CH_3$ | — | — | — | — | — | $CH_3$ | H | |
| Q-13 | H | $CO_2CH_3$ | — | — | $CH_3$ | $CH_3$ | — | — | — | |
| Q-14 | H | $CO_2CH_3$ | — | — | $CH_3$ | $CH_3$ | — | — | — | |

Formulations

Useful formulations of the compounds of Formula I and II can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE XXXIII

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff, and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 4

Wettable Powder

| | |
|---|---|
| 2-[4-(dimethylamino)phenylazo]-N—[(4-methoxy-6-methylpyrimidin-2-yl)aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 5

Wettable Powder

| | |
|---|---|
| [[2-[[(4-methoxy-6-methylpyrimidin-2-yl)aminocarbonyl]aminosulfonyl]phenyl]azo]phosphonic acid, dimethylester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 6

Granule

| | |
|---|---|
| Wettable Powder of Example 5 | 5% |
| attapulgite granules (U.S.S. 20–40 mesh: 0.84–0.42 mm) | 95% |

A slurry of wettable powder containing 25% solids is sprayed on the surface of attapulgite granules in a double-cone blender. The granules are dried and packaged.

EXAMPLE 7

Extruded Pellet

| | |
|---|---|
| 2-(dimethyl-1-triazeno)-N—[(4-methoxy-6-methylpyrimidin-2-yl)aminocarbonyl]benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 8

Oil Suspension

| | |
|---|---|
| [[2-[[(4-methoxy-6-methylpyrimidin-2-yl)aminocarbonyl]aminosulfonyl]phenyl]azo]phosphonic acid, dimethylester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 9

Wettable Powder

| | |
|---|---|
| 2-(dimethyl-1-triazeno)-N—[(4-methoxy-6-methylpyrimidin-2-yl)aminocarbonyl]benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 10

Low Strength Granule

| | |
|---|---|
| 2-(dimethyl-1-triazeno)-N—[(4-methoxy-6-methylpyrimidin-2-yl)aminocarbonyl]benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 11

Aqueous Suspension

| | |
|---|---|
| 2-[4-(dimethylamino)phenylazo]-N—[(4-methoxy-6-methylpyrimidin-2-yl)aminocarbonyl]benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 12

Solution

| | |
|---|---|
| [[2-[[(4-methoxy-6-methylpyrimidin-2-yl)amino-carbonyl]aminosulfonyl]phenyl]azo]phosphonic acid, dimethylester, sodium salt | 5% |
| water | 95% |

The salt is added directly to the water with stirring to produce the solution, which may then be packaged for use.

EXAMPLE 13

Low Strength Granule

| | |
|---|---|
| 2-[4-(dimethylamino)phenylazo]-N—[(4-methoxy-6-methylpyrimidin-2-yl)aminocarbonyl]benzenesulfonamide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

Granule

| | |
|---|---|
| [[2-[[(4-methoxy-6-methylpyrimidin-2-yl)amino-carbonyl]aminosulfonyl]phenyl]azo]phosphonic acid, dimethylester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 15

High Strength Concentrate

| | |
|---|---|
| 2-(dimethyl-1-triazeno)-N—[(4-methoxy-6-methyl-pyrimidin-2-yl)aminocarbonyl]benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 16

Wettable Powder

| | |
|---|---|
| 2-[4-(dimethylamino)phenylazo]-N—[(4-methoxy-6-methylpyrimidin-2-yl)aminocarbonyl]benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 17

Wettable Powder

| | |
|---|---|
| [[2-[[(4-methoxy-6-methylpyrimidin-2-yl)amino-carbonyl]aminosulfonyl]phenyl]azo]phosphonic acid, dimethylester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Oil Suspension

| | |
|---|---|
| 2-(dimethyl-1-triazeno)-N—[(4-methoxy-6-methyl-pyrimidin-2-yl)aminocarbonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 19

Dust

| | |
|---|---|
| 2-[4-(dimethylamino)phenylazo]-N—[(4-methoxy-6-methylpyrimidin-2-yl)aminocarbonyl]benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulants. Many of them have utility for broad-spectrum pre- and or postemergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat and cotton. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg of active ingredient per hectare, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (Echinochloa crusgalli), wild oats (Avena fatua), velvetleaf (Abutilon theophrasti), morningglory (Ipomoea spp.), cocklebur (Xanthium pensylvanicum), sicklepod (Cassia obtusifolia), cheatgrass (Bromus secalinus), bushbean, sorghum, corn, soybean, sugarbeet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;

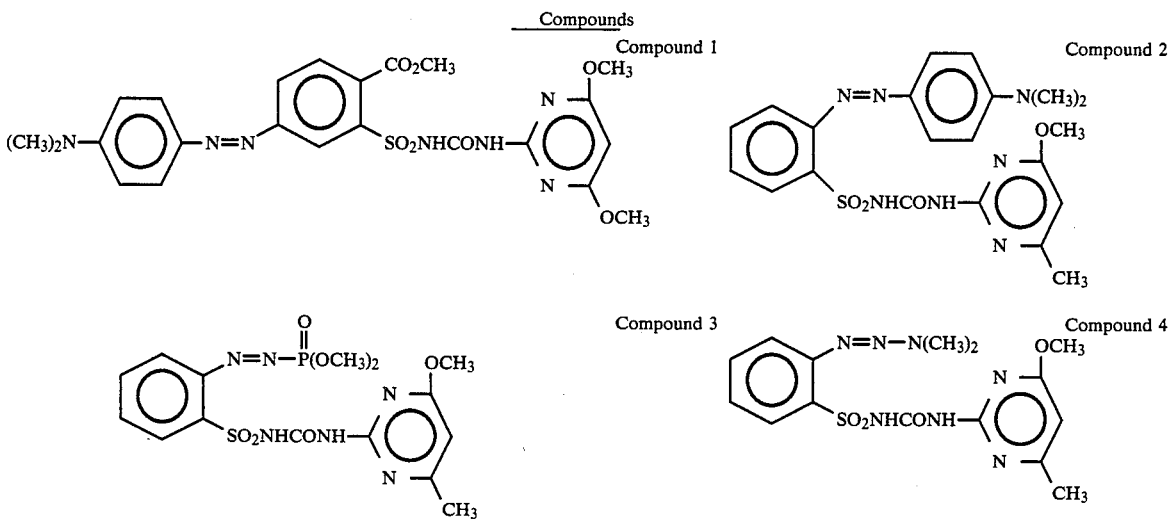
Compounds

X=axillary stimulation;
S=albinism; and
6Y=abscised buds or flowers.

TABLE A

| | | | | | Compound 1 | | | | | |
|---|---|---|---|---|---|---|---|---|---|---|
| TYPE TEST | RATE G/HA | BUSH-BEAN | COT-TON | SOR-GHUM | CORN | SOY-BEAN | WHEAT | WILD-OATS | RICE | BARN-YARD-GRASS |
| Post | 100 | 9C | 8C 9G | 5U 9G | 5U 9G | 4C 9G | 7G 5H | 3C 5G | 4C 9G | 5C 9H |
| Pre | 100 | — | — | 1C 9G | 1C 6G | 5H | 1C 5G | 1C 5G | 10E | 1C 9H |

| TYPE TEST | RATE G/HA | CRAB-GRASS | MORN-ING-GLORY | COCK-LE-BUR | SICK-LE-POD | NUT-SEDGE | SUGAR-BEETS | VELVET-LEAF | CHEAT-GRASS |
|---|---|---|---|---|---|---|---|---|---|
| Post | 100 | 2C 6G | 10C | 9C | 6C 9G | 1C 8G | — | — | — |
| Pre | 100 | 3C | 8G | 9H | 9G | 10E | — | — | — |

TABLE A-continued

8G

Compound 2

| TYPE TEST | RATE G/HA | BUSH-BEAN | COT-TON | SOR-GHUM | CORN | SOY-BEAN | WHEAT | WILD-OATS | RICE | BARN-YARD-GRASS |
|---|---|---|---|---|---|---|---|---|---|---|
| Post | 400 | 6C | 3C | 3C | 5C | 6C | 0 | 0 | — | 2C |
|  |  | 9G | 3H | 9G | 9H | 9G |  |  |  | 9H |
|  |  | 6Y | 8G |  |  |  |  |  |  |  |
| Pre | 400 | — | −1C | 1C | 5H | 5H | 1C | 1C | 10E | 2C |
|  |  |  | 9G | 9H |  |  | 6G | 5G |  | 8H |

| TYPE TEST | RATE G/HA | CRAB-GRASS | MORN-ING-GLORY | COCK-LE-BUR | SICK-LE-POD | NUT-SEDGE | SUGAR-BEETS | VELVET-LEAF | CHEAT-GRASS |
|---|---|---|---|---|---|---|---|---|---|
| Post | 400 | 2C | 8C | 2C | 2C | 2C | — | — | — |
|  |  |  |  | 7G | 6G | 8G |  |  |  |
| Pre | 400 | 2C | 9G | 9H | 9G | 10E | — | — | — |
|  |  | 8G |  |  |  |  |  |  |  |

Compound 3

| TYPE TEST | RATE G/HA | BUSH-BEAN | COT-TON | SOR-GHUM | CORN | SOY-BEAN | WHEAT | WILD-OATS | RICE | BARN-YARD-GRASS |
|---|---|---|---|---|---|---|---|---|---|---|
| Post | 400 | — | 4C | 3C | 3C | 3C | 5C | 3C | 5C | 3C |
|  |  |  | 9G | 9G | 9H | 9G | 9G | 9G | 9G | 9H |
| Post | 50 | — | 2C | 3C | 3C | 4C | 0 | 0 | 5C | 3C |
|  |  |  | 9G | 9H | 9G | 9G |  |  | 9G | 9H |
| Pre | 400 | — | 9G | 3C | 3C | 8G |  | 2C | 10E | 2C |
|  |  |  |  | 9H | 9G |  |  | 9G | 9G | 9H |
| Pre | 50 | — | 2C | 3C | 2C | 3C | 8G | 2C | 3C | 2C |
|  |  |  | 8G | 8H | 9G | 7G |  | 8G | 8G | 7G |

| TYPE TEST | RATE G/HA | CRAB-GRASS | MORN-ING-GLORY | COCK-LE-BUR | SICK-LE-POD | NUT-SEDGE | SUGAR-BEETS | VELVET-LEAF | CHEAT-GRASS |
|---|---|---|---|---|---|---|---|---|---|
| Post | 400 | 4G | 3C | 3C | 5C | 2C | 4C | — | — |
|  |  |  | 9G | 9G | 9G | 9G | 9G |  |  |
| Post | 50 | 2G | 0 | 1C | 3C | 2C | 5C | — | — |
|  |  |  |  | 2G | 8G | 8G | 9G |  |  |
| Pre | 400 | 5G | 9G | 9H | 9G | 9G | 5C | — | — |
|  |  |  |  |  |  |  | 9G |  |  |
| Pre | 50 | 0 | 8G | 9H | 8G | 7G | 4C | — | — |
|  |  |  |  |  |  |  | 9G |  |  |

Compound 4

| TYPE TEST | RATE G/HA | BUSH-BEAN | COT-TON | SOR-GHUM | CORN | SOY-BEAN | WHEAT | WILD-OATS | RICE | BARN-YARD-GRASS |
|---|---|---|---|---|---|---|---|---|---|---|
| Post | 50 | — | 10C | 3C | 3C | 5C | 3C | 3C | 6C | 9H |
|  |  |  |  | 9H | 9H | 9H | 6G | 7G | 9G |  |
| Pre | 50 | — | 9G | 5C | 3C | 3C | 8G | 3C | 4C | 3C |
|  |  |  |  | 9H | 9H | 8H |  | 8G | 8G | 9H |

| TYPE TEST | RATE G/HA | CRAB-GRASS | MORN-ING-GLORY | COCK-LE-BUR | SICK-LE-POD | NUT-SEDGE | SUGAR-BEETS | VELVET-LEAF | CHEAT-GRASS |
|---|---|---|---|---|---|---|---|---|---|
| Post | 50 | 6G | 3C | 4C | — | 6G | 0C | 9C | 3C |
|  |  |  | 7G | 8H |  |  |  |  | 7G |
| Pre | 50 | 4G | 7G | 8H | — | 3C | 10C | 10C | 9H |
|  |  |  |  |  |  | 5G |  |  |  |

Test B

Two 25 cm diameter plastic containers were lined with plastic bags and filled with Woodstown sandy loam. A 25 cm diameter Lucite® planting template was used to slightly compress the soil within each container and to provide indentations for the planting of nine crop or weed species. Seeds of the following species were placed in one container: mustard (*Brassica nigra*), cocklebur (*Xantium pensylvanicum*), velvetleaf (*Abutilon theophrasti*), sugar beets (*Beta vulgaris*), sicklepod (*Cassia obtusifolia*), morningglory (*Ipomoea* spp.), purle nutsedge (*Cyperus rotundus*), pigweed (*Amaranthus retroflexus*), teaweed (*Sida spinosa*), cotton (*Gossypium hirsutum*), jimsonweed (*Datura stramonium*) and soybean (*Glycine max.*). The second pot was planted with seeds of the following species: sorghum, (*Sorghum bicolor*), rice (*Oryza sativa*), giant foxtail (*Setaria faberii*), Dallisgrass (*Paspalum diltatum*), crabgrass (*Digitaria sanguinalis*), bluegrass (*Poa pratensis*), johnsongrass (*Sorghum halepense*), wild oats (*Avena fatua*), wheat (*Triticum aestivum*), cheatgrass (*Bromus secalinus*), barnyardgrass (*Echinochloa crusgalli*), and corn (*Zea mays*). Both containers were then topped with an approximately 1 cm layer of soil to cover the seeds. These two containers were then sprayed preemergence with the test compounds indicated in Table B. Following treatment, the plants were placed under an automatic overhead water device, where they received approximately 1 cm of simulated rainfall in a period of 150 minutes.

Approximately twenty-eight days after treatment, the plants were visually rated for response to the chemical treatments utilizing the rating system as described for Test A. The resuls are presented in Table B.

The ratings for the compound tested by this procedure are presented in Table C.

TABLE C

| | | | | | | | | | | |
|---|---|---|---|---|---|---|---|---|---|---|
| | Compound 2 | | | | | | | | | |
| RATE G/HA | SOY-BEAN | CORN | COT-TON | RICE | WHEAT | VEL-VET-LEAF | SESBANIA | SICK-LE-POD | MORN-ING-GLORY | |
| 62 | 7G 3C | 3G 4H | 7G 3C | 0 | 0 | 7G 4C | 7G 3C | 8G 3C | 9G 4C | |
| 250 | 10G 4C | 6G 3H | 8G 5C | 4G 3C | 0 | 10G 8C | 10G 5C | 10G 6C | 9G 4C | |
| RATE G/HA | JIM-SON-WEED | COCKLE-BUR | CRAB-GRASS | BARN-YARD-GRASS | GIANT-FOX-TAIL | WILD-OATS | SOR-GHUM | NUT-SEDGE | | |
| 62 | 6G 3C | 2C | 2G | 3G | 3G | 2G | 4G | 1G | | |
| 250 | 6G | 6G 3C | 5G | 7G | 5G | 6G | 7G | 1G | | |

TABLE B

| | | | | | Compound 1 | | | | | | |
|---|---|---|---|---|---|---|---|---|---|---|---|
| RATE G/HA | RICE | BARN-YARD GRASS | WHEAT | WILD-OATS | CRAB-GRASS | SOR-GHUM | JOHN-SON-GRASS | DAL-LIS-GRASS | GIANT-FOX-TAIL | BLUE-GRASS | CHEAT-GRASS | CORN |
| 120 | 8E 9G | 7G 4C | 0 | 7G 3C | 0 | 8G 5H | 3H 6G | 7G | 6G 3C | 7G 5C | 7G 3C | 2C |
| 31.2 | 7G | 4G | 0 | 6G | 0 | 5G 3H | 0 | 5G | 0 | 7G 3C | 5G | 0 |
| RATE G/HA | MUS-TARD | COCK-LE-BUR | PIG-WEED | NUT-SEDGE | COT-TON | MORN-ING-GLORY | SICKLE-POD | TEA-WEED | VEL-VET-LEAF | JIM-SON-WEED | SOY-BEAN | SUGAR-BEETS |
| 120 | 9G 9C | 5G | 8G 9C | 6G 3C | 3H 7G | 7G | 8G 9C | 5G | 8G 7C | 5G 3H | 6G 3H | 8G 8C |
| 31.2 | 8G 3C | 6G | 8G 8C | 3G | 2G | 0 | 5G | 0 | 6G 5H | 0 | 0 | 4G |
| | | | | | Compound 2 | | | | | | |
| RATE G/HA | RICE | BARN-YARD GRASS | WHEAT | WILD-OATS | CRAB-GRASS | SOR-GHUM | JOHN-SON-GRASS | DAL-LIS-GRASS | GIANT-FOX-TAIL | BLUE-GRASS | CHEAT-GRASS | CORN |
| 250 | 8G 3H | 4G | 3G | 5G | 0 | 7G 5H | 4G | 0 | 0 | 3G | 5G | 2G 2H |
| 62.5 | — | 0 | — | 0 | 0 | 0 | 3G | 0 | 0 | 0 | 0 | 0 |
| RATE G/HA | MUS-TARD | COCK-LE-BUR | PIG-WEED | NUT-SEDGE | COT-TON | MORN-ING-GLORY | SICKLE-POD | TEA-WEED | VEL-VET-LEAF | JIM-SON-WEED | SOY-BEAN | SUGAR-BEETS |
| 250 | 8G 5C | 0 | 8G 9C | 0 | 0 | 3G | 7G | 5G | 5G 5H | 0 | 3G | 6G 4C |
| 62.5 | 8G | 0 | 7G | 0 | 0 | 3G | 0 | 0 | 3G | 0 | 4G | 4G |

Test C

In Test C, plastic pots filled with Fallsington sandy loam were planted to soybeans, cotton, corn, rice, wheat, sorghum, velvetleaf (*Abutilon theophrasti*), sesbania (*Sesbania exaltata*), Sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). Eighteen days after planting, the young plants and the soil around them were sprayed overall with the test chemicals dissolved in a non-phytotoxic solvent. Fourteen days after treatment, all species were compared to untreated controls and visually rated for response to treatment utilizing the rating system previously described for Test A.

Test D

Postemergence

Two round pans (25 cm diameter by 12.5 cm deep) were filled with Sassafras sandy loam soil. One pan was planted with blackgrass (*Alopecurus myosuroides*), sugarbeets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, sugarbeet, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Sassafras sandy loam soil. One pan was planted with blackgrass, sugarbeets, nutsedge, crabgrass, sicklepod, teaweed, jimsonweed, velvetleaf, and giant foxtail. The other pan was planted with wheat, cotton, rice, corn, sugarbeet, soybean, wild oats, cocklebur, morningglory, johnsongrass and barnyardgrass. The two pans were sprayed pre-emergence with the chemicals dissolved in a non-phytoxic solvent.

Treated plants and controls were maintained in the greenhouse for 28 days, then all treated plants were compared to controls and visually rated for plant response utilizing the rating system previously described for Test A.

TABLE D

Compound 2

| TYPE TEST | RATE G/HA | CORN | WHEAT | RICE | SOY-BEAN | COTTON | SUGAR-BEET | CRAB-GRASS | JOHN-SON-GRASS | BLACK-GRASS | BARN-YARD-GRASS |
|---|---|---|---|---|---|---|---|---|---|---|---|
| POST | 250 | 10G | 0 | 10G | 10G | 10G | 10C | 3G | 4G | 8G | 9G |
|  | 62 | 10G | 0 | 10G | 9G | 9G | 10C | 0 | 0 | 5G | 7G |
|  | 16 | 6G | 0 | 6G | 8G | 4G | 7G | 0 | 0 | 0 | 3G |
|  | 4 | 2G | 0 | 0 | 4G | 0 | 3G | 0 | 0 | 0 | 0 |
| PRE | 250 | 9G | 0 | 10E | 8G | 8G | 10G | 4G | 6G | 6G | 9G |
|  | 62 | 9G | 0 | 9G | 6G | 6G | 7G | 3G | 0 | 3G | 4G |
|  | 16 | 3G | 0 | 8G | 3G | 3G | 4G | 0 | 0 | 0 | 2G |
|  | 4 | 0 | 0 | 3G | 0 | 0 | 0 | 0 | 0 | 0 | 0 |

| TYPE TEST | RATE G/HA | NUT-SEDGE | GIANT-FOX-TAIL | WILD-OATS | COCKLE-BUR | MORN-ING-GLORY | TEA-WEED | SICKLE-POD | JIM-SON-WEED | VELVET-LEAF |
|---|---|---|---|---|---|---|---|---|---|---|
| POST | 250 | 10C | 5G | 3G | 10G | 7G | 8G | 10G | 8G | 10C |
|  | 62 | 4G | 3G | 0 | 5G | 5G | 5G | 3G | 5G | 10G |
|  | 16 | 0 | 0 | 0 | 0 | 0 | 3G | 0 | 0 | 7G |
|  | 4 | 0 | 0 | 0 | 0 | 0 | 0 | 0 | 0 | 2G |
| PRE | 250 | 0 | 3G | 3G | 9G | 0 | 8G | 10E | 9G | 10G |
|  | 62 | 0 | 0 | 0 | 9G | 0 | 4G | 10E | 4G | 6G |
|  | 16 | 0 | 0 | 0 | 3G | 0 | 2G | 4G | 2G | 4G |
|  | 4 | 0 | 0 | 0 | 0 | 0 | 0 | 0 | 0 | 3G |

What is claimed is:

1. A compound of Formulae I or II

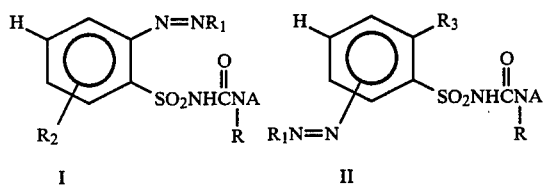

or an agriculturally suitable salt thereof, wherein:

R is H or $CH_3$;

$R_1$ is $NR_4R_5$, $N(CH_3)OR_6$, NHCN, NRA, $P(W)R_4(W_1R_5)$, $P(W)(W_1R_4)(W_2R_5)$, $P^+(C_6H_5)_3$, $P^+R_6R_7R_8$, $SR_9$, $SO_2R_9$, $C(R_{10})(R_{11})NO_2$, $CH(CN)_2$ or Q;

Q is

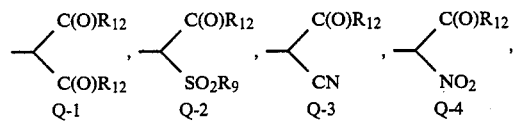

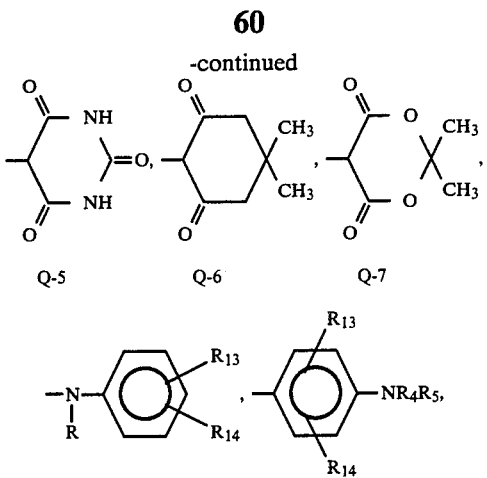

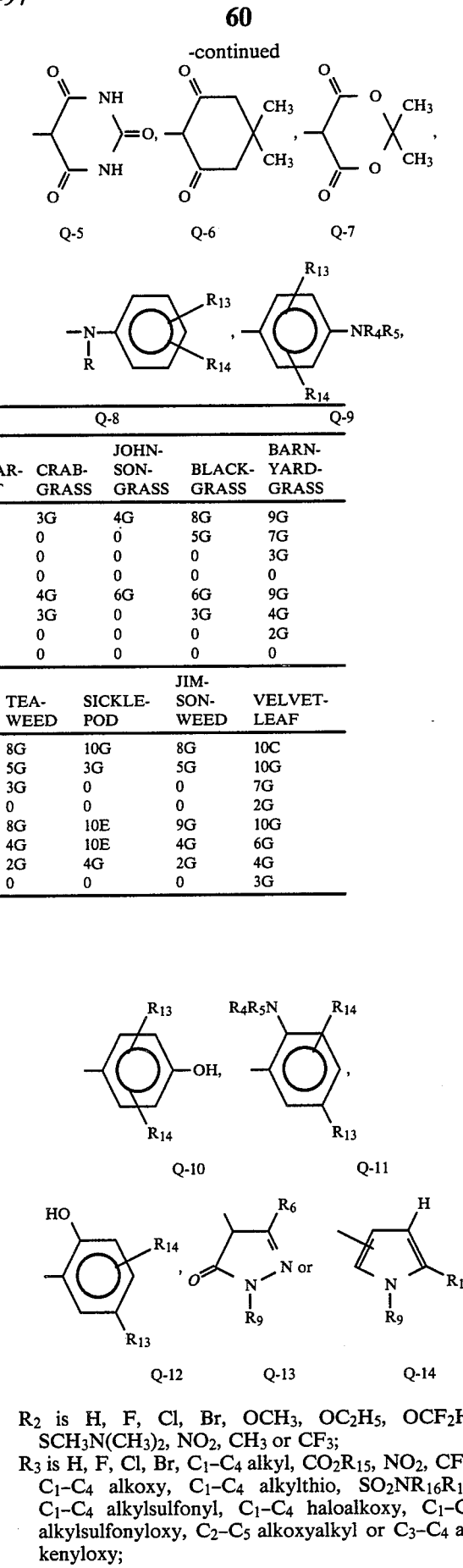

$R_2$ is H, F, Cl, Br, $OCH_3$, $OC_2H_5$, $OCF_2H$, $SCH_3 N(CH_3)_2$, $NO_2$, $CH_3$ or $CF_3$;

$R_3$ is H, F, Cl, Br, $C_1-C_4$ alkyl, $CO_2R_{15}$, $NO_2$, $CF_3$, $C_1-C_4$ alkoxy, $C_1-C_4$ alkylthio, $SO_2NR_{16}R_{17}$, $C_1-C_4$ alkylsulfonyl, $C_1-C_4$ haloalkoxy, $C_1-C_4$ alkylsulfonyloxy, $C_2-C_5$ alkoxyalkyl or $C_3-C_4$ alkenyloxy;

$R_4$ and $R_5$ are independently $C_1-C_4$ alkyl, $C_2-C_4$ alkyl substituted by 1 atom of Br or 1-3 atoms of F or Cl, $C_3-C_5$ alkenyl, $C_3-C_5$ cycloalkyl, OH, $OCH_3$, $CH_2OH$, $CH_2OR_6$, or $CH_2CH_2OR_6$; or $R_4$ and $R_5$ when taken together are $-(CH_2)_4-$, $-(CH_2)_5-$ or $-(CH_2)_2O(CH_2)_2-$;

$R_6$ is $C_1-C_4$ alkyl;

$R_7$ and $R_8$ are independently $C_1-C_4$ alkyl;

$R_9$ is $C_1-C_4$ alkyl, phenyl or phenyl substituted with 1-3 atoms of F, Cl or 1 Br;

$R_{10}$ and $R_{11}$ are independently H, $C_1-C_4$ alkyl, phenyl or phenyl substituted with 1 atom of Br or 1-3 atoms of F or Cl;

$R_{12}$ is $C_1-C_4$ alkyl, $C_1-C_4$ alkoxy or $NHR_9$;

$R_{13}$ and $R_{14}$ are independently H, $C_1-C_3$ alkyl, $OR_6$, $SR_6$, $NHC(O)R_6$, F, Cl, Br or $CO_2R_6$;

$R_{15}$ is $C_1-C_4$ alkyl, $C_3-C_4$ alkenyl, $CH_2CH_2Cl$ or $CH_2CH_2OCH_3$;

$R_{16}$ and $R_{17}$ are independently $C_1-C_2$ alkyl;

W is O or S;

$W_1$ and $W_2$ are independently O, S or NH;

A is

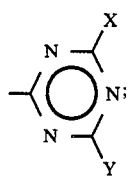

X is $CH_3$, $OCH_3$, $OCH_2CH_3$, $CH_2F$, $OCH_2CH_2F$, $OCH_2CHF_2$, $OCH_2CF_3$ or $CF_3$;

Y is H, $C_1-C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$,

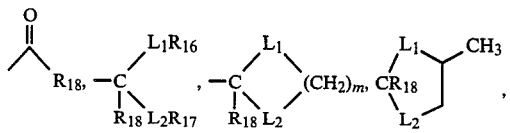

$SCF_2H$ or cyclopropyl;

m is 2 or 3;

$L_1$ and $L_2$ are independently O or S;

$R_{18}$ is H or $CH_3$;

provided that when Q is Q-11 or Q-12, then $R_{13}$ is other than H.

2. A compound of claim 1 wherein R is H.

3. A compound of claim 2 wherein X is $CH_3$ or $OCH_3$ and Y is $CH_3$, $OCH_3$, $OC_2H_5$, or $CH_2OCH_3$.

4. A compound of claim 3 wherein $R_2$ is H, Cl, $CH_3$ or $OCH_3$ and $R_3$ is Cl, $C_1-C_3$ alkyl, $C_1-C_3$ alkoxy, $NO_2$, $CO_2(C_1-C_3$ alkyl), $SO_2N(CH_3)_2$, $OSO_2CH_3$, $OSO_2C_2H_5$, $SO_2CH_3$, $SO_2C_2H_5$ or allyloxy.

5. A composition for the control of undesirable vegetation consisting essentially of a compound of claim 1 and at least one of (a) a surface active agent, and (b) a solid or liquid diluent.

6. A composition for the control of undesirable vegetation consisting essentially of a compound of claim 1 and at least one of (a) a surface active agent, and (b) a solid or liquid diluent.

7. A composition for the control of undesirable vegetation consisting essentially of a compound of claim 3 and at least one of (a) a surface active agent, and (b) a solid or liquid diluent.

8. A composition for the control of undesirable vegetation consisting essentially of a compound of claim 4 and at least one of (a) a surface active agent, and (b) a solid or liquid diluent.

9. A method for the control of undesirable vegetation comprising applying to the locus of such vegetation an herbicidally effective amount of a compound of claim 1.

10. A method for the control of undesirable vegetation comprising applying to the locus of such vegetation an herbicidally effective amount of a compound of claim 2.

11. A method for the control of undesirable vegetation comprising applying to the locus of such vegetation an herbicidally effective amount of a compound of claim 3.

12. A method for the control of undesirable vegetation comprising applying to the locus of such vegetation an herbicidally effective amount of a compound of claim 4.

* * * * *